United States Patent
Buchman et al.

(10) Patent No.: US 6,511,824 B1
(45) Date of Patent: Jan. 28, 2003

(54) NUCLEIC ACIDS AND POLYPEPTIDES OF INVERTEBRATE TWIK CHANNELS AND METHODS OF USE

(75) Inventors: Andrew Roy Buchman, Berkeley, CA (US); Christian Burks, Berkeley, CA (US); Helen Louise Francis-Lang, San Francisco, CA (US); Lucile A. Gillett, San Mateo, CA (US); Jonathan Cagampang Heller, San Francisco, CA (US); Casey Casimir Kopczynski, Belmont, CA (US); Jonathan Scott Margolis, San Carlos, CA (US); Darren Mark Platt, San Francisco, CA (US); Bindu Priya Reddy, Foster City, CA (US); Candace Swimmer, San Francisco, CA (US); John W. Winslow, El Granada, CA (US); Yuling Luo, Castro Valley, CA (US)

(73) Assignee: Exelixis, Inc., S. San Francisco, CA (US)

( * ) Notice: Subject to any disclaimer, the term of this patent is extended or adjusted under 35 U.S.C. 154(b) by 0 days.

(21) Appl. No.: 09/362,842

(22) Filed: Jul. 28, 1999

Related U.S. Application Data

(63) Continuation-in-part of application No. 09/270,767, filed on Mar. 17, 1999.

(51) Int. Cl.⁷ .......................... C12N 15/00; C12N 15/63; C12N 5/00; C07H 21/04

(52) U.S. Cl. ................... 435/69.1; 435/320.1; 435/325; 536/23.5

(58) Field of Search ............................... 514/23.1, 23.5; 435/320.1, 325, 69.1; 800/8, 13, 2

(56) References Cited

U.S. PATENT DOCUMENTS 5,559,026 A  9/1996  Price et al.
5,650,550 A  * 7/1997  Korach et al. ................ 800/2

FOREIGN PATENT DOCUMENTS

WO  WO 96/13520  5/1996

OTHER PUBLICATIONS

J Rudinger, Peptide Hormones, "Characteristics of the amino acids as componenets of a peptide hormone sequence," Jun. 1976, pp. 1–7 in Peptide Hormones, Ed. J.A. Parsons, University Park Press, Baltimore, USA.*
DA O'Brochta et al., "Recent Developments in Transgenic Insect Technology," Parasitology Today, 1997, vol. 13, No. 3, pp. 99–104.*
CA Villee et al., General Zoology 6th Ed., 1984 Saunders College Publishing, Chap. 24, pp. 509–515, Chap. 27, pp. 602–613.*

M Adams et al., Database Gen Embl. Accession No. AC017756, Dec. 1999.*

SE Celniker,Database Gen Embl. Accession No. AC 007646, Mar. 2000.*

Celniker et al., "*Drosophila melanogaster* chromosome 3 clone BACR03J04 (D687) RPCI–9803.J.4 map 87F–87F strain y; cn bw sp", Genbank GI No. 4895159 [online], Jun. 4, 1999 [retrieved on Dec. 27, 1999]. Retrieved from the Internet: <URL: http://ww.ncbi.nlm.nih.gov/entrez/query-.fcgl?cmd=Retrieve&db=nucleotide&list_uids=4895159&dopt=GenBank>.

Duprat, et al., "*Homo sapiens* TWIK–related acid–sensitive K+ channel (TASK) mRNA," Genbank GI No. 2465541 [online], Oct. 6, 1997 [retrieved on Dec. 27, 1999]. Retrieved from the Internet: <URL: http://ww.ncbi.nlm.nih.gov/entrez/query.fcgl?cmd=Retrieve&db=nucleotide&list_uids=2465541&dopt=GenBank>.

Kim, et al., "*Mus musculus* mRNA for cTBAK", Genbank GI No. 3043543 [online], Feb. 13, 1999 [retrieved on Dec. 27, 1999]. Retrieved from the Internet: <URL: http://ww.ncbi.nlm.nih.gov/entrez/query.fcgl?cmd=Retrieve&db=nucleotide&list_uids=3043543&dopt=GenBank>.

Fujita, et al., "*Mus musculus* mRNA for cTBAK" Genbank GI No. 3149958 [online], May 21, 1998 [retrieved on Dec. 27, 1999]. Retrieved from the Internet: <URL: http://ww.ncbi.nlm.nih.gov/entrez/query.fcgl?cmd=Retrieve&db=nucleotide&list_uids=3149958&dopt=GenBank>.

Duprat et al., "*Mus musculus* TWIK–related acid–sensitive K+ channel (TASK) mRNA" GenBankGI No. 2465543 [online],Oct. 6, 1997 [retrieved on Dec. 27, 1999]. Retrieved from the Internet: <URL: http://ww.ncbi.nlm.nih.gov/entrez/query.fcgl?cmd=Retrieve&db=nucleotide&list_uids=2465543&dopt=GenBank.

(List continued on next page.)

*Primary Examiner*—Ram R. Shukla
(74) *Attorney, Agent, or Firm*—Jan P. Brunelle; Laleh Shayesteh

(57) ABSTRACT

Tandem pore domain weak inward rectifying K⁺ (TWIK) channel nucleic acids and proteins that have been isolated from *Drosophila melanogaster* and Leptinotarsa are described. The TWIK channel nucleic acids and proteins can be used to genetically modify metazoan invertebrate organisms, such as insects, coelomates, and pseudocoelomates, or cultured cells, resulting in TWIK channel expression or mis-expression. The genetically modified organisms or cells can be used in screening assays to identify candidate compounds which are potential pesticidal agents or therapeutics that interact with TWIK channel proteins. They can also be used in methods for studying TWIK channel activity and identifying other genes that modulate the function of, or interact with, the TWIK channel gene.

5 Claims, 34 Drawing Sheets

OTHER PUBLICATIONS

Wilson, et al., "contains similarity to outward–rectifier potassium channels [*Caenorhabditis elegans*]." GenBank GI No. 2429407 [online], Nov. 5, 1998 [retrieved on Dec. 27, 1999]. Retrieved from the Internet: <URL: http://ww.ncbi.nlm.nih.gov/entrez/query.fcgl?cmd=Retrieve&db=protein&list_uids=2429407&dopt=GenPep>t.

Wang, et al., "putative potassium channel subunit n2P38 [*Caenorhabditis elegans*]." GenBank GI No. 3452417 [online], Aug. 26, 1998 [retrieved on Dec. 27, 1999]. Retrieved from the Internet: <URL: http://ww.ncbi.nlm.nih.gov/entrez/query.fcgl?cmd=Retrieve&db=protein&list_uids=3452417&dopt=GenPept.

Duprat et al., "TWIK–related acid–sensitive K+ channel [*Homo sapiens*]." GenBankGI No. 2465542 [online], Oct. 6, 1997 [retrieved on Dec. 27, 1999]. Retrieved from the Internet: <URL: http://ww.ncbi.nlm.nih.gov/entrez/query.fcgl?cmd=Retrieve&db=protein&list_uids=2465542&dopt=GenPept>.

Leonoudakis, et. al., "TWIK–related acid–sensitive K+ channel [*Rattus norvegicus*]," GenBank GI No. 2809391 [online], Jan. 26, 1998 [retrieved on Dec. 27, 1999]. Retrieved from the Internet: <URL: http://ww.ncbi.nlm.nih.gov/entrez/query.fcgl?cmd=Retrieve&db=protein&list_uids=2809391&dopt=GenPept>.

Kim et al., "cTBAK [*Mus musculus*]." GenBank GI No. 3043544 [online], Feb. 13, 1999 [retrieved on Dec. 27, 1999]. Retrieved from the Internet: <URL: http://ww.ncbi.nlm.nih.gov/entrez/query.fcgl?cmd=Retrieve&db=protein&list_uids=3043544&dopt=GenPept>.

Salkoff et al., 1995, "Surfing the DNA Databases for $K^+$ Channels Nets Yet More Diversity", Neuron 15:489–492.

* cited by examiner

```
ATGACGAGCACGAGCACAAAGATAGATCGCGAAAGTAGCACACGACTGCG  50
TACTGCTCGTGCTCGTGTTTCTATCTAGCGCTTTCATCGTGTGCTGACGC

GCTGGACAAGATGGAGCAGCCGATGGACGCCAGGCAGCAGCAGCGCCATC  100
CGACCTGTTCTACCTCGTCGGCTACCTGCGGTCCGTCGTCGTCGCGGTAG

GAAGGCGCCTGGGTCGCAGCCACCGGGAACCGACGCCCGTCACTGGAGAC  150
CTTCCGCGGACCCAGCGTCGGTGGCCCTTGGCTGCGGGCAGTGACCTCTG

GCCCTGCCCCAGGACGATGCCAGTCCGGATGCCCTCCCTGATCCATCACC  200
CGGGACGGGGTCCTGCTACGGTCAGGCCTACGGGAGGGACTAGGTAGTGG

TCAGATGGTGCGCATGCAGATCAGGCCACCCGGCTCGATGTCCGCCCACG  250
AGTCTACCACGCGTACGTCTAGTCCGGTGGGCCGAGCTACAGGCGGGTGC

AGAGCAAGATCCTGCGAAAGCGGGACAAGTCCTTCGCCAGCTCCTCGGCG  300
TCTCGTTCTAGGACGCTTTCGCCCTGTTCAGGAAGCGGTCGAGGAGCCGC

CGTAGTCAATCGCAGCCACGGGAGGCTGAGAAGCTGAGTAGTCCGGATGC  350
GCATCAGTTAGCGTCGGTGCCCTCCGACTCTTCGACTCATCAGGCCTACG

CAATCATCTGATCAAGCATCGCAGCCTCTCCTCGCCGCGGCACAAGGAGG  400
GTTAGTAGACTAGTTCGTAGCGTCGGAGAGGAGCGGCGCCGTGTTCCTCC

AGTCCAGCGAGAGTGAGCTGACCACCGGCAGCAGTAGTCAGCAGCAAAGG  450
TCAGGTCGCTCTCACTCGACTGGTGGCCGTCGTCATCAGTCGTCGTTTCC

CCCATTCCTAATCTTGGCCAGACACAGGATACGCTAAGCAGATTGGAGCA  500
GGGTAAGGATTAGAACCGGTCTGTGTCCTATGCGATTCGTCTAACCTCGT

GAATCTGCAGCGCTTCGAGGACGAACGACGGCGTTTCGAGGCCGAGAAGA  550
CTTAGACGTCGCGAAGCTCCTGCTTGCTGCCGCAAAGCTCCGGCTCTTCT

GGCTCTTTGAGCGCGAGAAGCGGGAGCACAAGATGCGCCATCGCCAGCAG  600
CCGAGAAACTCGCGCTCTTCGCCCTCGTGTTCTACGCGGTAGCGGTCGTC

CTGGACAACGAGGAGCGCAAGCGCCTCCTGCAGAGCTACCGCAAGCTCAG  650
GACCTGTTGCTCCTCGCGTTCGCGGAGGACGTCTCGATGGCGTTCGAGTC

CGATCGCATCCAGCTGCCGCAGGACGAGGAGGAACGGCGCCGCCTCATCC  700
GCTAGCGTAGGTCGACGGCGTCCTGCTCCTCCTTGCCGCGGCGGAGTAGG

ACAGCCTGCGTCTGCAGCGACACGAGGCGCCCAAGACTCGGGGTCGCAAT  750
TGTCGGACGCAGACGTCGCTGTGCTCCGCGGGTTCTGAGCCCCAGCGTTA
```

FIG. 2A

```
CGAAGTAGCGGCTACGATGAGTCCTCCACCCAGTTCAGCTCCTCCGATGC  800
GCTTCATCGCCGATGCTACTCAGGAGGTGGGTCAAGTCGAGGAGGCTACG

CGATGCGACGGAGGAGACTCACCCGCGGCCCCGAGCACCTAAGATTCCCC  850
GCTACGCTGCCTCCTCTGAGTGGGCGCCGGGGCTCGTGGATTCTAAGGGG

AGGGCTTTGTGGCAGCCCCAATCCGCGGCGCACCTCCACCGCCGCCATCG  900
TCCCGAAACACCGTCGGGGTTAGGCGCCGCGTGGAGGTGGCGGCGGTAGC

GCGTCGACAGCTCCAAAACCACCGGAAAGGCTGTCTGTGAGTCGCAACAA  950
CGCAGCTGTCGAGGTTTTGGTGGCCTTTCCGACAGACACTCAGCGTTGTT

CTCCCTGTCGCCCGTGAGACCACAGCGACGATCCAAGACTCCGGAGCAAC 1000
GAGGGACAGCGGGCACTCTGGTGTCGCTGCTAGGTTCTGAGGCCTCGTTG

GGGAGGAGATCCTCCGGAAGCACGAGTACTTGGAGGTGGGCGAGTCCAGA 1050
CCCTCCTCTAGGAGGCCTTCGTGCTCATGAACCTCCACCCGCTCAGGTCT

GACGAGGTGATAAAGCCCCGCATCTCGGAGGCAGAACAGCAGTCGGAGCT 1100
CTGCTCCACTATTTCGGGGCGTAGAGCCTCCGTCTTGTCGTCAGCCTCGA

GATGCAAAAGTACATGGAGGCCGCTGAGCGGGCGGCAAAAGCGGAGGCCG 1150
CTACGTTTTCATGTACCTCCGGCGACTCGCCCGCCGTTTTCGCCTCCGGC

CCCTGGCGGAGCAAATCCTGACGGCGGAGGGAGTGCGTCGCAGTCACAGC 1200
GGGACCGCCTCGTTTAGGACTGCCGCCTCCCTCACGCAGCGTCAGTGTCG

TTGAGATTAGCGGATAAGGAAGAGAAGCCTCAAAAGCGCAGCTCCAGTTT 1250
AACTCTAATCGCCTATTCCTTCTCTTCGGAGTTTTCGCGTCGAGGTCAAA

GGAGCGTCCACTAAGACCCAAGCGATCGGGCAGTTTGGAAAGAAAGGAAC 1300
CCTCGCAGGTGATTCTGGGTTCGCTAGCCCGTCAAACCTTTCTTTCCTTG

AGGTAACTCAAGAGCTCCTTGAGGGAACTACTACAAATGAAGCTGATACG 1350
TCCATTGAGTTCTCGAGGAACTCCCTTGATGATGTTTACTTCGACTATGC

GAACCAAAATCTCTTGGGGATCAACCCTTGTTGCCAGAGGAATCCATCTC 1400
CTTGGTTTTAGAGAACCCCTAGTTGGGAACAACGGTCTCCTTAGGTAGAG

AGAGGCGAAACCCAAAGTTACCTTATGGCAGCGGCTGAAAAATCTGTTTA 1450
TCTCCGCTTTGGGTTTCAATGGAATACCGTCGCCGACTTTTTAGACAAAT

GGCGAAAGAAGAAGATTCAGGCAAAGGGCGAAGATGTCACAGATCTGTCC 1500
CCGCTTTCTTCTTCTAAGTCCGTTTCCCGCTTCTACAGTGTCTAGACAGG
```

FIG. 2B

```
ACAGAATTGCCACTGGAGAAGTTGGCCTCCAGGGGTCTGCTGTACAGTTT   1550
TGTCTTAACGGTGACCTCTTCAACCGGAGGTCCCCAGACGACATGTCAAA

CAGCCTAGAAGCCCGGCATGAATGGAAACGCCTCAAGCTGGACTATCCCC   1600
GTCGGATCTTCGGGCCGTACTTACCTTTGCGGAGTTCGACCTGATAGGGG

AAAAGGTGAAGGAACTGCGTCAGCTACGCAACAGGTGCATTGCCTATCTC   1650
TTTTCCACTTCCTTGACGCAGTCGATGCGTTGTCCACGTAACGGATAGAG

ATCTGCATGGCTATGCTTCTGGGATTCGGAGGACTCCTGTTCCGGTACAC   1700
TAGACGTACCGATACGAAGACCCTAAGCCTCCTGAGGACAAGGCCATGTG

GGAAGGAGCAGCGGAGAATATATACAAGTGCGAGGTGCGCAAGGTGAAGC   1750
CCTTCCTCGTCGCCTCTTATATATGTTCACGCTCCACGCGTTCCACTTCG

GGGATTTCATAGACCGACTGTGGGACGTCAGCCACAACATGAGAGAGGAG   1800
CCCTAAAGTATCTGGCTGACACCCTGCAGTCGGTGTTGTACTCTCTCCTC

GACTGGAAGTCTCTTGCCCGCCAGAAGCTGCGCAGCTTCGAGGATGAACT   1850
CTGACCTTCAGAGAACGGGCGGTCTTCGACGCGTCGAAGCTCCTACTTGA

AAATAATTTAGCCGAGTTGGGACTACGCCGCTATCCGGGCCAAAAGTCCT   1900
TTTATTAAATCGGCTCAACCCTGATGCGGCGATAGGCCCGGTTTTCAGGA

GGAACTTTGTCAATTGCTTCATCTTCTGTTGGACCGTGATCACAACTATA   1950
CCTTGAAACAGTTAACGAAGTAGAAGACAACCTGGCACTAGTGTTGATAT

GGTTACGGCCACATCACTCCAAAGACGGGCATGGGTCGATCCCTGACCAT   2000
CCAATGCCGGTGTAGTGAGGTTTCTGCCCGTACCCAGCTAGGGACTGGTA

CGTCTATGCCATCATCGGCATCCCCATGTTCCTGATCGTGCTGGCCGATC   2050
GCAGATACGGTAGTAGCCGTAGGGGTACAAGGACTAGCACGACCGGCTAG

TGGGCAAGTTATTCACGCGCTGCGTCAAGTTCCTGTGGGTGTATGTGCGA   2100
ACCCGTTCAATAAGTGCGCGACGCAGTTCAAGGACACCCACATACACGCT

CGGATGTACTACACGCGCTCCTGCCGCCGGATACGAAAGCAGCAGCAGAT   2150
GCCTACATGATGTGCGCGAGGACGGCGGCCTATGCTTTCGTCGTCGTCTA

CCGGAGCGCCATGACAGGCTTCAATACGATGTACGACATGGCCATCCGCA   2200
GGCCTCGCGGTACTGTCCGAAGTTATGCTACATGCTGTACCGGTAGGCGT

GGCCGAGCATGTTCTTCAGCAACTCTGCGCCAGAGAACGATGAGGAGTCG   2250
CCGGCTCGTACAAGAAGTCGTTGAGACGCGGTCTCTTGCTACTCCTCAGC
```

FIG. 2C

```
CAGGCGGATGCCGAGGCCGCAAGATCGGTGGGCACCTCGCACCCGGAGAC  2300
GTCCGCCTACGGCTCCGGCGTTCTAGCCACCCGTGGAGCGTGGGCCTCTG

ACCCACATCACCCTATCCAGAGACCTTCGAGGTGGACGACGAGTTCAATT  2350
TGGGTGTAGTGGGATAGGTCTCTGGAAGCTCCACCTGCTGCTCAAGTTAA

TGCCAGTGTCGGTGGCCTCGCTGCTGCTCATTACGTACATCCTCCTAGGA  2400
ACGGTCACAGCCACCGGAGCGACGACGAGTAATGCATGTAGGAGGATCCT

TCCTTCGGCTTTCTAATGATGGAGCCCAGCTGGACTCCACTGGATGCCTT  2450
AGGAAGCCGAAAGATTACTACCTCGGGTCGACCTGAGGTGACCTACGGAA

CTACTACGTGTTCATCTCGATGTCCACAATTGGGTTCGGCGACCTGGTGC  2500
GATGATGCACAAGTAGAGCTACAGGTGTTAACCCAAGCCGCTGGACCACG

CCAGTAATCCCTTCTACGTAATGGTCAGCATGATCTATCTGATGTTCGGC  2550
GGTCATTAGGGAAGATGCATTACCAGTCGTACTAGATAGACTACAAGCCG

TTGGCCCTGACCTCCATGTTCATCAATGTGGTGCAGATCAAGCTGAGCGA  2600
AACCGGGACTGGAGGTACAAGTAGTTACACCACGTCTAGTTCGACTCGCT

TCACTTCAAAATGGCCAGCGCCAAAGTGGGCGCCACCATTGGCATGAACA  2650
AGTGAAGTTTTACCGGTCGCGGTTTCACCCGCGGTGGTAACCGTACTTGT

TGACCAGCGAGCTTGGTGATGAGGGCGGCTCCCAGGTGAAGACTCCCTCC  2700
ACTGGTCGCTCGAACCACTACTCCCGCCGAGGGTCCACTTCTGAGGGAGG

GAGCTTGCCTCGGTGCACGGTTCGCGACTGGACAGGATCGAGGAGGATGG  2750
CTCGAACGGAGCCACGTGCCAAGCGCTGACCTGTCCTAGCTCCTCCTACC

CCAGGAGGCGAATGGCAATGGCCACTCCCCGGTGCCACCACTCACCTCGA  2800
GGTCCTCCGCTTACCGTTACCGGTGAGGGGCCACGGTGGTGAGTGGAGCT

TCCTGCGCGCACCGCGTCCTCTATCGCCGGCGTCCAATGGAGTGGATGCT  2850
AGGACGCGCGTGGCGCAGGAGATAGCGGCCGCAGGTTACCTCACCTACGA

AATGGAGTTGGAGCCGATGCTGTTGGAGCTGGGGATGTTACTCCGCCACC  2900
TTACCTCAACCTCGGCTACGACAACCTCGACCCCTACAATGAGGCGGTGG

TCTGCTGCCCAGGCGTCAGGTTTCCGTGGATCCCCAGCCGCCGGCGGAGG  2950
AGACGACGGGTCCGCAGTCCAAAGGCACCTAGGGGTCGGCGGCCGCCTCC

GGGAGAACAAGAAGAAGAAAAAGCACAGGTTTTTCTAG
CCCTCTTGTTCTTCTTCTTTTTCGTGTCCAAAAAGATC
```

FIG. 2D

```
MTSTSTKIDRESSTRLRLDKMEQPMDARQQQRHRRRLGRSHREPTPVTGD   50

ALPQDDASPDALPDPSPQMVRMQIRPPGSMSAHESKILRKRDKSFASSSA  100

RSQSQPREAEKLSSPDANHLIKHRSLSSPRHKEESSESELTTGSSSQQQR  150

PIPNLGQTQDTLSRLEQNLQRFEDERRRFEAEKRLFEREKREHKMRHRQQ  200

LDNEERKRLLQSYRKLSDRIQLPQDEEERRRLIHSLRLQRHEAPKTRGRN  250

RSSGYDESSTQFSSSDADATEETHPRPRAPKIPQGFVAAPIRGAPPPPS   300

ASTAPKPPERLSVSRNNSLSPVRPQRRSKTPEQREEILRKHEYLEVGESR  350

DEVIKPRISEAEQQSELMQKYMEAAERAAKAEAALAEQILTAEGVRRSHS  400

LRLADKEEKPQKRSSSLERPLRPKRSGSLERKEQVTQELLEGTTTNEADT  450

EPKSLGDQPLLPEESISEAKPKVTLWQRLKNLFRRKKKIQAKGEDVTDLS  500

TELPLEKLASRGLLYSFSLEARHEWKRLKLDYPQKVKELRQLRNRCIAYL  550

ICMAMLLGFGGLLFRYTEGAAENIYKCEVRKVKRDFIDRLWDVSHNMREE  600

DWKSLARQKLRSFEDELNNLAELGLRRYPGQKSWNFVNCFIFCWTVITTI  650

GYGHITPKTGMGRSLTIVYAIIGIPMFLIVLADLGKLFTRCVKFLWVYVR  700

RMYYTRSCRRIRKQQQIRSAMTGFNTMYDMAIRRPSMFFSNSAPENDEES  750

QADAEAARSVGTSHPETPTSPYPETFEVDDEFNLPVSVASLLLITYILLG  800

SFGFLMMEPSWTPLDAFYYVFISMSTIGFGDLVPSNPFYVMVSMIYLMFG  850

LALTSMFINVVQIKLSDHFKMASAKVGATIGMNMTSELGDEGGSQVKTPS  900

ELASVHGSRLDRIEEDGQEANGNHSPVPPLTSILRAPRPLSPASNGVDA   950

NGVGADAVGAGDVTPPPLLPRRQVSVDPQPPAEGENKKKKKHRFF*
```

FIG. 3

```
ATGTCGGGTAGGCGGGCCCAATCTCTGCCGGCGCACATGTTGGAGCCAGC  50
TACAGCCCATCCGCCCGGGTTAGAGACGGCCGCGTGTACAACCTCGGTCG

GAAGCCGCAACGCGGACGCTGTGTAGCTGCCATCTGCTTCTCGTGGAAGG  100
CTTCGGCGTTGCGCCTGCGACACATCGACGGTAGACGAAGAGCACCTTCC

TGCTCACCTGCATTGTGTCCCATGTGCTGCTCGTGCTTCTCGTGGTTTCC  150
ACGAGTGGACGTAACACAGGGTACACGACGAGCACGAAGAGCACCAAAGG

TATTGCGTGGGCGGTGCCTACCTCTTCCAGCATCTCGAACGACCCCACGA  200
ATAACGCACCCGCCACGGATGGAGAAGGTCGTAGAGCTTGCTGGGGTGCT

ACTAGAGGTGAAGCGAGACATACAGAATCTTCGCGTTAATCTCACGGAGA  250
TGATCTCCACTTCGCTCTGTATGTCTTAGAAGCGCAATTAGAGTGCCTCT

ATATCTGGCTACTGTCCGACGACGCAGTGGTCCTAAGGGAAAGCGATTGG  300
TATAGACCGATGACAGGCTGCTGCGTCACCAGGATTCCCTTTCGCTAACC

ATGGCCAATGTCAGCAAGCACCTGGCCAATTTTGAAAAGCAAATCCTTAC  350
TACCGGTTACAGTCGTTCGTGGACCGGTTAAAACTTTTCGTTTAGGAATG

GGCCATCAAGGCCGACGGCTGGGATGGCGACGAGGATCTGCGCAAGTCCC  400
CCGGTAGTTCCGGCTGCCGACCCTACCGCTGCTCCTAGACGCGTTCAGGG

AGTGGACCTTTGCCGGATCCCTGTTCTACTCGATTATTGTGATAACGACC  450
TCACCTGGAAACGGCCTAGGGACAAGATGAGCTAATAACACTATTGCTGG

ATAGGCTATGGTCACATATCGCCGCGTACGGATTGGGGCAAGGTGACAAC  500
TATCCGATACCAGTGTATAGCGGCGCATGCCTAACCCCGTTCCACTGTTG

GATTTTCTACGCCATTGTGGGCATTCCGCTGATGCTCATCTGCTTGTCCA  550
CTAAAAGATGCGGTAACACCCGTAAGGCGACTACGAGTAGACGAACAGGT

ACATTGGCGATGTCATGGCCACATCATTTCGGTTTCTGTACTGGAGAATA  600
TGTAACCGCTACAGTACCGGTGTAGTAAAGCCAAAGACATGACCTCTTAT

TGCTGCTATGTGTGCACCCGCACGGCCAAACGTCCGAGGAATGCCCGATC  650
ACGACGATACACACGTGGGCGTGCCGGTTTGCAGGCTCCTTACGGGCTAG

CCGGCAGAGATCGATGCGCTCTCAGCGCCATGCCCGATCCCAGCCGCCGC  700
GGCCGTCTCTAGCTACGCGAGAGTCGCGGTACGGGCTAGGGTCGGCGGCG

CCTCGTTCCGGCGCTCCATGAAGATGACCCAACGGTCTGGGAATGACTCG  750
GGAGCAAGGCCGCGAGGTACTTCTACTGGGTTGCCAGACCCTTACTGAGC

GGTCTGGGTCCTTCCATGGGTCATGCCTATTCAGATCCCGACCTGCGCAC  800
CCAGACCCAGGAAGGTACCCAGTACGGATAAGTCTAGGGCTGGACGCGTG

CATGGGCCGGGGCTACGATGACCGCGAGTTCGGACATCGGAGCAGTGGAG  850
GTACCCGGCCCCGATGCTACTGGCGCTCAAGCCTGTAGCCTCGTCACCTC
```

FIG. 4A

```
GCGGACGGAATCGTCGTCAGCAGCAGCAGCAGCAGCATTTGCATCACGAT   900
CGCCTGCCTTAGCAGCAGTCGTCGTCGTCGTCGTAAACGTAGTGCTA

CCTCGCCAGCGTCACACCATTTACGGAGATGGGTACGAAACTCAGACCCT   950
GGAGCGGTCGCAGTGTGGTAAATGCCTCTACCCATGCTTTGAGTCTGGGA

GAACAGATCCAACCGCTACAGTAGCCGGCAAAGACAACGGGATCGGATGA  1000
CTTGTCTAGGTTGGCGATGTCATCGGCCGTTTCTGTTGCCCTAGCCTACT

GGGACAGACACACGGTAGAAAGGGAGCGCTACTCCCGATCCCACTTGGAT  1050
CCCTGTCTGTGTGCCATCTTTCCCTCGCGATGAGGGCTAGGGTGAACCTA

GCTGGATCCATTGAGGACTTCGGTGACATGCAACCTCCTGCGAAAAGAGC  1100
CGACCTAGGTAACTCCTGAAGCCACTGTACGTTGGAGGACGCTTTTCTCG

TGCCAGTGTGCGATCGGTTCGATCGCCACACAATCAGGAATCTTCCAAAG  1150
ACGGTCACACGCTAGCCAAGCTAGCGGTGTGTTAGTCCTTAGAAGGTTTC

CGTCCAGAGAACTGCATCGTCTTCACTCGGCACCTGGGAGAAGTAGGGCC  1200
GCAGGTCTCTTGACGTAGCAGAAGTGAGCCGTGGACCCTCTTCATCCCGG

AAGTCCGTGGATCCCAGGCACGTTTCTTCACATTACGAAGACGTCGACGA  1250
TTCAGGCACCTAGGGTCCGTGCAAAGAAGTGTAATGCTTCTGCAGCTGCT

GGACGTGGTGAGGAAAACACCAATTATACCAAATAGGTATGCTTTAGATG  1300
CCTGCACCACTCCTTTTGTGGTTAATATGGTTTATCCATACGAAATCTAC

ACTTCGGGGGCAACAGAAGACAAGCAGCTCCAAGGAGTCAATCCATGCCC  1350
TGAAGCCCCGTTGTCTTCTGTTCGTCGAGGTTCCTCAGTTAGGTACGGG

AGATCTGCTCACCAAAGGCAACGCCAGAAGGACAGAGAACGGGAACGATC  1400
TCTAGACGAGTGGTTTCCGTTGCGGTCTTCCTGTCTCTTGCCCTTGCTAG

TCCACAGCCGCCACCGCAGAGCTCCTATCGCCAACAGCATGATAGACGAG  1450
AGGTGTCGGCGGTGGCGTCTCGAGGATAGCGGTTGTCGTACTATCTGCTC

CTGGAAGTCTGGGCAGGCAATCATCTCGCTATGGCAACCATCTCGAACTT  1500
GACCTTCAGACCCGTCCGTTAGTAGAGCGATACCGTTGGTAGAGCTTGAA

CCCGACTATGATGCTCCACCGCCGGGACGGGACCATCGACGGGATAGGCG  1550
GGGCTGATACTACGAGGTGGCGGCCCTGCCCTGGTAGCTGCCCTATCCGC

TGGTCACTCCCAGGGTCGCTACGAGGACTACGTGGAAGAGAGCTTCGATG  1600
ACCAGTGAGGGTCCCAGCGATGCTCCTGATGCACCTTCTCTCGAAGCTAC

AGGGATCCCTTTACGGAGACAATAACTACGAGGATTATCCGCCTGAGCGC  1650
TCCCTAGGGAAATGCCTCTGTTATTGATGCTCCTAATAGGCGGACTCGCG

CACCACTCAAGGAGTCGAGAACCAAAAGAAATCGCCGAAGAGAGCGGGC   1700
GTGGTGAGTTCCTCAGCTCTTGGTTTTCTTTAGCGGCTTCTCTCGCCCG
```

FIG. 4B

```
TGAACGTTTGCCCCCTTCCCCGAGAATCATGTCACCAATGGGATTTCCGG  1750
ACTTGCAAACGGGGGAAGGGGCTCTTAGTACAGTGGTTACCCTAAAGGCC

TCCAGCGGCAAATCCGTCGGCGACCCAGCTACGATTACGACGACGATGAC  1800
AGGTCGCCGTTTAGGCAGCCGCTGGGTCGATGCTAATGCTGCTGCTACTG

TCTATGTACGGGGATGAGTATGGGGACTATGGAGATCTGCTGCCCAAGGA  1850
AGATACATGCCCTACTCATACCCCTGATACCTCTAGACGACGGGTTCCT

TCGACCTGTCCCCATTTGGTTATGCGTCTTTCTGGTAGTGAGCTACATCC  1900
AGCTGGACAGGGGTAAACCAATACGCAGAAAGACCATCACTCGATGTAGG

TTGGCGGAGCTGTTCTTTTTGCGTACTGGGAGAACTGGTCCTTCTTGGAT  1950
AACCGCCTCGACAAGAAAACGCATGACCCTCTTGACCAGGAAGAACCTA

TCCGCCTACTTTTGCTTCATTACACTGACAACAATCGGATTTGGTGACTT  2000
AGGCGGATGAAAACGAAGTAATGTGACTGTTGTTAGCCTAAACCACTGAA

TGTCCCCGCGAAAGGAGTCAAGGACGAGTCGGAGCAGTCCATCGCCTATT  2050
ACAGGGGCGCTTTCCTCAGTTCCTGCTCAGCCTCGTCAGGTAGCGGATAA

GCTCGCTGTACCTTCTTTTCGGCATTGCCTTGTTGGCCATGAGTTTTAAC  2100
CGAGCGACATGGAAGAAAGCCGTAACGGAACAACCGGTACTCAAAATTG

CTGGTCCAGGAGGAGTTCATTGCCAATGTGAAGGAGGTAGCCCGCCGTCT  2150
GACCAGGTCCTCCTCAAGTAACGGTTACACTTCCTCCATCGGGCGGCAGA

GGGCATTCTTAAGGATGATGACGACGAGCAGGATGAGGATTAG
CCCGTAAGAATTCCTACTACTGCTGCTCGTCCTACTCCTAATC
```

FIG. 4C

```
MSGRRAQSLPAHMLEPAKPQRGRCVAAICFSWKVLTCIVSHVLLVLLVVS   50

YCVGGAYLFQHLERPHELEVKRDIQNLRVNLTENIWLLSDDAVVLRESDW  100

MANVSKHLANFEKQILTAIKADGWDGDEDLRKSQWTFAGSLFYSIIVITT  150

IGYGHISPRTDWGKVTTIFYAIVGIPLMLICLSNIGDVMATSFRFLYWRI  200

CCYVCTRTAKRPRNARSRQRSMRSQRHARSQPPPSFRRSMKMTQRSGNDS  250

GLGPSMGHAYSDPDLRTMGRGYDDREFGHRSSGGGRNRRQQQQQQHLHHD  300

PRQRHTIYGDGYETQTLNRSNRYSSRQRQRDMRDRHTVERERYSRSHLD   350

AGSIEDFGDMQPPAKRAASVRSVRSPHNQESSKASRELHRLHSAPGRSRA  400

KSVDPRHVSSHYEDVDEDVVRKTPIIPNRYALDDFGGNRRQAAPRSQSMP  450

RSAHQRQRQKDRERERSPQPPPQSSYRQQHDRRAGSLGRQSSRYGNHLEL  500

PDYDAPPPGRDHRRDRRGHSQGRYEDYVEESFDEGSLYGDNNYEDYPPER  550

HHSRSREPKRNRRRERAERLPPSPRIMSPMGFPVQRQIRRRPSYDYDDDD  600

SMYGDEYGDYGDLLPKDRPVPIWLCVFLVVSYILGGAVLFAYWENWSFLD  650

SAYFCFITLTTIGFGDFVPAKGVKDESEQSIAYCSLYLLFGIALLAMSFN  700

LVQEEFIANVKEVARRLGILKDDDDEQDED*
```

FIG. 5

```
ATGTCCTCCCGACGCAGCTCCTTCAGGCGGAGGGAGAAGCCGGCCTTCGA  50
TACAGGAGGGCTGCGTCGAGGAAGTCCGCCTCCCTCTTCGGCCGGAAGCT

GCGCTTTAAGGACCACTGCCGCCACTTCACGGCGTTCATGTTCAGCAACG  100
CGCGAAATTCCTGGTGACGGCGGTGAAGTGCCGCAAGTACAAGTCGTTGC

TGGGCATCATTCTACTGGTCACATTTTATATTATCGGCGGAGCGTTCATA  150
ACCCGTAGTAAGATGACCAGTGTAAAATATAATAGCCGCCTCGCAAGTAT

TTCCAGAGCATCGAGATTTTCGAGTACGAGCGGCTCAAGTCGGAGAAGCC  200
AAGGTCTCGTAGCTCTAAAAGCTCATGCTCGCCGAGTTCAGCCTCTTCGG

GCACCGGTTTATAGCACGGAACTTCAGTGGCGAGTGCCTCAGCCGCATAT  250
CGTGGCCAAATATCGTGCCTTGAAGTCACCGCTCACGGAGTCGGCGTATA

GGGAGTTGACGGCGGAGAACATCAGCTTCTTCGACCACCACGCCTACAGG  300
CCCTCAACTGCCGCCTCTTGTAGTCGAAGAAGCTGGTGGTGCGGATGTCC

AGACGGGTGAACGATGTGCTTCTGGATTATCAGAGGGCCATAGTGAAAAA  350
TCTGCCCACTTGCTACACGAAGACCTAATAGTCTCCCGGTATCACTTTTT

GCAGCTGAAGGGACCCGACGTGGAGCAGTGGAGCTTCTCCGGAGCTTTTC  400
CGTCGACTTCCCTGGGCTGCACCTCGTCACCTCGAAGAGGCCTCGAAAAG

TCTACTCACTGACGGTGATCACGACCATCGGGTACGGGAACATTACGCCG  450
AGATGAGTGACTGCCACTAGTGCTGGTAGCCCATGCCCTTGTAATGCGGC

CACTCCGAGTGCGGAAAGCTGGTGACCATTCTATATGCGATAATTGGCAT  500
GTGAGGCTCACGCCTTTCGACCACTGGTAAGATATACGCTATTAACCGTA

GCCGCTGTTCTTGCTCTACCTGTCCAACATTGGAGACGTCCTGGCCAAGT  550
CGGCGACAAGAACGAGATGGACAGGTTGTAACCTCTGCAGGACCGGTTCA

CCTTCAAGTGGATATACTCGAAGGTGTGCCTATGTCGCATCTGCCCCGGC  600
GGAAGTTCACCTATATGAGCTTCCACACGGATACAGCGTAGACGGGGCCG

GTGGCCAAGCGCCGGATAATCCGCGAGAGACGAAAAATGCGACAGTTGGC  650
CACCGGTTCGCGGCCTATTAGGCGCTCTCTGCTTTTTACGCTGTCAACCG

CAGAGCGCTCCAGATGCACGACATGGAGAATGCCCGGGGAAGCAGCAGCT  700
GTCTCGCGAGGTCTACGTGCTGTACCTCTTACGGGCCCCTTCGTCGTCGA

ACACTAGCACCAGCAGTACCACCTCCTCCAACAGCAGCAGTAGCGAATAC  750
TGTGATCGTGGTCGTCATGGTGGAGGAGGTTGTCGTCGTCATCGCTTATG
```

FIG. 6A

```
ACCAGAAGTTCCCGCCAGAGTTCCAGCCTCGTGGATATTCAGTACACCGA  800
TGGTCTTCAAGGGCGGTCTCAAGGTCGGAGCACCTATAAGTCATGTGGCT

GTCTGATTCGGATATCGAGCGGGAAATACGCGGCAGCACGGATGAAATTA  850
CAGACTAAGCCTATAGCTCGCCCTTTATGCGCCGTCGTGCCTACTTTAAT

CAGTGCCAGTCACTGTGTGCGTCTTCGTTATGGTCGGGTATATCCTGTGG  900
GTCACGGTCAGTGACACACGCAGAAGCAATACCAGCCCATATAGGACACC

GGTGCGCTGCTCTTCGGTCGTTGGGAGGACTGGAACTATCTGGATGGGAG  950
CCACGCGACGAGAAGCCAGCAACCCTCCTGACCTTGATAGACCTACCCTC

CTACTTCTGCCTTATATCGCTCAGCAGCATTGGATTTGGCGATCTGGTGC  1000
GATGAAGACGGAATATAGCGAGTCGTCGTAACCTAAACCGCTAGACCACG

CAGGCGATCGTGTGATAACTGCCGACAGGGATAAGGTGGAGGTTAGCTTC  1050
GTCCGCTAGCACACTATTGACGGCTGTCCCTATTCCACCTCCAATCGAAG

ATTCTCTGCGCCATATATCTGCTGCTCGGCATGGCCGTGATTGCCATGTG  1100
TAAGAGACGCGGTATATAGACGACGAGCCGTACCGGCACTAACGGTACAC

CTTCAATTTGATGCAGGAGCAGGTCGTTCACAACATTCGGGCGATCAAGC  1150
GAAGTTAAACTACGTCCTCGTCCAGCAAGTGTTGTAAGCCCGCTAGTTCG

GGGGATTCAAGGCCTGCTTTCGGTGCCGCACCTCCTAG
CCCCTAAGTTCCGGACGAAAGCCACGGCGTGGAGGATC
```

FIG. 6B

MSSRRSSFRRREKPAFERFKDHCRHFTAFMFSNVGIILLVTFYIIGGAFI 50

FQSIEIFEYERLKSEKPHRFIARNFSGECLSRIWELTAENISFFDHHAYR 100

RRVNDVLLDYQRAIVKKQLKGPDVEQWSFSGAFLYSLTVITTIGYGNITP 150

HSECGKLVTILYAIIGMPLFLLYLSNIGDVLAKSFKWIYSKVCLCRICPG 200

VAKRRIIRERRKMRQLARALQMHDMENARGSSSYTSTSSTTSSNSSSSEY 250

TRSSRQSSSLVDIQYTESDSDIEREIRGSTDEITVPVTVCVFVMVGYILW 300

GALLFGRWEDWNYLDGSYFCLISLSSIGFGDLVPGDRVITADRDKVEVSF 350

ILCAIYLLLGMAVIAMCFNLMQEQVVHNIRAIKRGFKACFRCRTS*

FIG. 7

```
ATGTCCGACGTTGAGCAGGCGATTAAGGCCAAGCAACCGCAGCCGTCTCA  50
TACAGGCTGCAACTCGTCCGCTAATTCCGGTTCGTTGGCGTCGGCAGAGT

GTTGGACTGCTCCATTGACGATGAGACGGATGCCACCGAATTCGGAGGCC  100
CAACCTGACGAGGTAACTGCTACTCTGCCTACGGTGGCTTAAGCCTCCGG

TGGGCGGAGTGGGTGGTGCGGGTTGTGGATCGGAGATGGGTGCCAAGACC  150
ACCCGCCTCACCCACCACGCCCAACACCTAGCCTCTACCCACGGTTCTGG

ACCGCTTCGCTGACCGCCAAGCCGCGCAGCAGTCTCCGGCGCTGCTGCGG  200
TGGCGAAGCGACTGGCGGTTCGGCGCGTCGTCAGAGGCCGCGACGACGCC

TCACTTGCTCAAGCTGCTCTTCTCCACGCCCGGCCTGGTGCTCCTGGTCA  250
AGTGAACGAGTTCGACGAGAAGAGGTGCGGGCCGGACCACGAGGACCAGT

TCGGCTACTCCGTGCTGGGCGGGCTCCTCTTCCCGCTGCTGGAGGCGCCG  300
AGCCGATGAGGCACGACCCGCCCGAGGAGAAGGGCGACGACCTCCGCGGC

CAGGACATCAGCAAGTCGGCTGCCATTGCCAAGAGCCGGGAGGACTGCTT  350
GTCCTGTAGTCGTTCAGCCGACGGTAACGGTTCTCGGCCCTCCTGACGAA

GCGCGAACTCTGGATCATTACAGAGAAACTCAACGTTCTGTACGAACGCA  400
CGCGCTTGAGACCTAGTAATGTCTCTTTGAGTTGCAAGACATGCTTGCGT

ACTGGACGATGTTGGTCCACGAGCAGCTGCGTCGCTTCGAGGGCTCCATT  450
TGACCTGCTACAACCAGGTGCTCGTCGACGCAGCGAAGCTCCCGAGGTAA

GTGGCGGCCACGCGCCAAGGATCTGCTGGCTCCTCCGGCGGAGGAGGAGC  500
CACCGCCGGTGCGCGGTTCCTAGACGACCGAGGAGGCCGCCTCCTCCTCG

AGGACTCTTCCACGAGGGCAGTGCGAGTGCCCTGGGCCACTTTGGCTACG  550
TCCTGAGAAGGTGCTCCCGTCACGCTCACGGGACCCGGTGAAACCGATGC

ATGCCGGCGACTCGCAGAGCTGGTCATTCAGCGAAGCTCTGCTCTACTCG  600
TACGGCCGCTGAGCGTCTCGACCAGTAAGTCGCTTCGAGACGAGATGAGC

GTCACTGTGATAACGACAATTGGTCACGGCAGCCTGACGCCGCGCACCGC  650
CAGTGACACTATTGCTGTTAACCAGTGCCGTCGGACTGCGGCGCGTGGCG

CGCCGGGAAGCTGGCGACCATCTTCTACGCCCTGGTGGGCGTGCCCCTCA  700
GCGGCCCTTCGACCGCTGGTAGAAGATGCGGGACCACCCGCACGGGGAGT

TGCTGATGTGCCTGTCCAGCTTGGGAGCCCTGCTCGCCGATGGCCTGCAG  750
ACGACTACACGGACAGGTCGAACCCTCGGGACGAGCGGCTACCGGACGTC
```

FIG. 8A

```
TGCACCTACGTGCGACTGTGCTGCCAGCTGCAGAGGCACCAGGAGCACAG 800
ACGTGGATGCACGCTGACACGACGGTCGACGTCTCCGTGGTCCTCGTGTC

AAGAAAGTCCACACCAGGCACATCGACGCCATCTGCCAGCAGTGCGGCCA 850
TTCTTTCAGGTGTGGTCCGTGTAGCTGCGGTAGACGGTCGTCACGCCGGT

ACTCGAGGGAAAAGGACACGGACAAGAGGTCCAAGCGGCGAATGTTTTTC 900
TGAGCTCCCTTTTCCTGTGCCTGTTCTCCAGGTTCGCCGCTTACAAAAAG

CCACCCCATCACGAAAGTTTTTCCCCGGCAACTAAGACAGTTTCGTTTTT 950
GGTGGGGTAGTGCTTTCAAAAGGGGCCGTTGATTCTGTCAAAGCAAAAA

GGCCAGCGGAAAACCTGAATCCCTGGTCGCTTATGTATGGAAATGGAAGG 1000
CCGGTCGCCTTTTGGACTTAGGGACCAGCGAATACATACCTTTACCTTCC

CTGGCAAGTCAGGATGTGATGGGAATCTTCGATTGTCCGGCGATTTGCTT 1050
GACCGTTCAGTCCTACACTACCCTTAGAAGCTAACAGGCCGCTAAACGAA

TCCTCAATGGAATTCAACCCATTTTTCGCAGATCAGACTGCACTGGGGTC 1100
AGGAGTTACCTTAAGTTGGGTAAAAGCGTCTAGTCTGACGTGACCCCAG

TCAAATTACGGCTTTTAATTACGACAGCAGAAGCCTTTTAAGTGGATCTC 1150
AGTTTAATGCCGAAAATTAATGCTGTCGTCTTCGGAAAATTCACCTAGAG

CAAGCCGCACAAGGATGCGTCTGGCAATTGATAAGACTGCCAGCAGATTG 1200
GTTCGGCGTGTTCCTACGCAGACCGTTAACTATTCTGACGGTCGTCTAAC

CGGTTGGCTCTGGGGATGTGCAGTCATCGGTTGAATTATTATCGCCATCG 1250
GCCAACCGAGACCCCTACACGTCAGTAGCCAACTTAATAATAGCGGTAGC

TGTTGACTGCTGCCATTTCGGCTTTTGGTCTTTTGCTCTTTTGGCCTTTG 1300
ACAACTGACGACGGTAAAGCCGAAAACCAGAAAACGAGAAAACCGGAAAC

CCATCGTTCTTGCAATTATCATGACGCATGCTGCCGTAACGGTTTTTCGC 1350
GGTAGCAAGAACGTTAATAGTACTGCGTACGACGGCATTGCCAAAAGCG

CGCAGTGTGGACACAGGACATCCCCGGAACCAGGGAGATAATTATTCGGC 1400
GCGTCACACCTGTGTCCTGTAGGGGCCTTGGTCCCTCTATTAATAAGCCG

ATTATCTTTTAAGTGCACAGCCAATTGCAAGGGCTGCCAGTACGATGCGG 1450
TAATAGAAAATTCACGTGTCGGTTAACGTTCCCGACGGTCATGCTACGCC

CTAACAGTGAGACGAGCTTAAATGACTGCTTGGAGTATGGCCAAAAGGGA 1500
GATTGTCACTCTGCTCGAATTTACTGACGAACCTCATACCGGTTTTCCCT
```

FIG. 8B

```
AAGCTGCCGCCAGACAAAAAGGAAGGAGATGCCTGTCAATTGTTGCGCAA 1550
TTCGACGGCGGTCTGTTTTTCCTTCCTCTACGGACAGTTAACAACGCGTT

CTTGAATCCGCAGCAGCACTTCTACCAGCAGCAGCAGCAGCAGCCGCAGC 1600
GAACTTAGGCGTCGTCGTGAAGATGGTCGTCGTCGTCGTCGTCGGCGTCG

AGCCGGATGTCATGCTAATGACAACGACATCGGGCAGTGCGCTGCTGAAA 1650
TCGGCCTACAGTACGATTACTGTTGCTGTAGCCCGTCACGCGACGACTTT

TACGCACCGCAACAGCAACAACTGCAGCAGCAGCAGCAATTATCGACAGC 1700
ATGCGTGGCGTTGTCGTTGTTGACGTCGTCGTCGTCGTTAATAGCTGTCG

AACACTCCCGCGACAACATCATCAGATGCAGCTGCAGCAGCAGCAGCAGC 1750
TTGTGAGGGCGCTGTTGTAGTAGTCTACGTCGACGTCGTCGTCGTCGTCG

AACTGCAACAGAACTTCGTGGCTGTGCCCAGCAGCATGCTGCGAATGCCG 1800
TTGACGTTGTCTTGAAGCACCGACACGGGTCGTCGTACGACGCTTACGGC

CTCACAGTGCCGCCAAATTGTTATGCGCCCGCGACAGCAACGATCTACTT 1850
GAGTGTCACGGCGGTTTAACAATACGCGGGCGCTGTCGTTGCTAGATGAA

TCCGTTCGGCCACGCCCCCTCCGCCCCGGGCAGTCCCGCCCACAACCAAG 1900
AGGCAAGCCGGTGCGGGGAGGCGGGGCCCGTCAGGGCGGGTGTTGGTTC

CCCACCCAACCCAGAATCCGAATGGCAATGCACTGGGAAACACTACCCTC 1950
GGGTGGGTTGGGTCTTAGGCTTACCGTTACGTGACCCTTTGTGATGGGAG

GGTTCCCAGCCGCTGGTCAAGTACCACACGATACACTTGCAACCCGCATC 2000
CCAAGGGTCGGCGACCAGTTCATGGTGTGCTATGTGAACGTTGGGCGTAG

CGGGAAGCATCGAGTGTTGGCTTCTGGACTTCAGGATGCAACAGCCGTGA 2050
GCCCTTCGTAGCTCACAACCGAAGACCTGAAGTCCTACGTTGTCGGCACT

ATCTCGTGACAGCATCCGAGGCATCCACTTCCACCCTGGAGGCCATCACT 2100
TAGAGCACTGTCGTAGGCTCCGTAGGTGAAGGTGGGACCTCCGGTAGTGA

TTGCCACCGCCTCCGGCCTACCAAACAGCCAGCGTGCACGGACGAAGCCC 2150
AACGGTGGCGGAGGCCGGATGGTTTGTCGGTCGCACGTGCCTGCTTCGGG

CCCTCGGATGTCCCCCTTCAACGCCACAGTGCTCATTTACGCTTTCAATT 2200
GGGAGCCTACAGGGGAAGTTGCGGTGTCACGAGTAAATGCGAAAGTTAA

ATATAACAATTTTCATCATCATCATCATCATCAGCAGCTTGCAGCAGCGT 2250
TATATTGTTAAAAGTAGTAGTAGTAGTAGTAGTCGTCGAACGTCGTCGCA
```

FIG. 8C

```
GTTAAAATGACAGATTTTCAACTTGTGCTGCTCGACATGCCAGGACATCA 2300
CAATTTTACTGTCTAAAAGTTGAACACGACGAGCTGTACGGTCCTGTAGT

ACAGCAACAGCAACAAGGACCTGTGCGGCGGGCCAAGTTCGTGGCGAAGC 2350
TGTCGTTGTCGTTGTTCCTGGACACGCCGCCCGGTTCAAGCACCGCTTCG

CATTGCCACAAGAGATCAACGCACTGATGGACTGCGGAACGGGATCGCCA 2400
GTAACGGTGTTCTCTAGTTGCGTGACTACCTGACGCCTTGCCCTAGCGGT

GACTTATCCGGCAGACATGATTTATTGCCGCCACCCCATTCGGGGTCACC 2450
CTGAATAGGCCGTCTGTACTAAATAACGGCGGTGGGGTAAGCCCCAGTGG

AGCAACAGGCACCGCCGCAAGTCCTTTGTTGACCTACACAGCCGCAGCAA 2500
TCGTTGTCCGTGGCGGCGTTCAGGAAACAACTGGATGTGTCGGCGTCGTT

CAAGCCCACAGCTGTCAGCTGGAATTAAAGGCGGATCAGGACCAGCACCC 2550
GTTCGGGTGTCGACAGTCGACCTTAATTTCCGCCTAGTCCTGGTCGTGGG

ACGGCTGGAGCACCAATGCTTGTCAGCGGAGCCGGCAGAGGGGCAGCCGC 2600
TGCCGACCTCGTGGTTACGAACAGTCGCCTCGGCCGTCTCCCCGTCGGCG

TCTGACCGATAACGGTTTTATGGCCGCAGGTGTCTGTGGCATGGGTGCTG 2650
AGACTGGCTATTGCCAAAATACCGGCGTCCACAGACACCGTACCCACGAC

CTGCTGCACCCCTTCCAGTAACATCAATGGGTGCAGCCACTACAACAGCC 2700
GACGACGTGGGGAAGGTCATTGTAGTTACCCACGTCGGTGATGTTGTCGG

TCCTCGGCAGCATCCACATTGTCGGCTCTTCTAAGCGCCAACTCCACGGG 2750
AGGAGCCGTCGTAGGTGTAACAGCCGAGAAGATTCGCGGTTGAGGTGCCC

CAACGTGGACATCATGGAGGACGAGGATGAGCAGGAACGGGAGCGTTTGA 2800
GTTGCACCTGTAGTACCTCCTGCTCCTACTCGTCCTTGCCCTCGCAAACT

GCAACTGTCCGCACGGAACGCCGTCCCGAGTGCCGCTGATAGCGAGTCCT 2850
CGTTGACAGGCGTGCCTTGCGGCAGGGCTCACGGCGACTATCGCTCAGGA

TTGAGTGTGCCGCAGGACTCGGGCGAGAATACCACCCGCAACACCGCCTT 2900
AACTCACACGGCGTCCTGAGCCCGCTCTTATGGTGGGCGTTGTGGCGGAA

CAACCGCCACACACTGCAGCCGCTGAGCCGCAAGACGCTGCTGCTGACTC 2950
GTTGGCGGTGTGTGACGTCGGCGACTCGGCGTTCTGCGACGACGACTGAG

GCCGTTGCCACAGACACGCCTCTGGAACGCTGTACGACAGTACGGCGAAC 3000
CGGCAACGGTGTCTGTGCGGAGACCTTGCGACATGCTGTCATGCCGCTTG
```

FIG. 8D

```
AACACGGAGACCTCCGACGACGAGGAGTACATGCAACACGGCAGCGAGCA  3050
TTGTGCCTCTGGAGGCTGCTGCTCCTCATGTACGTTGTGCCGTCGCTCGT

GTTTGTGCTGAAGAAGTTGCGCTACCACTGCGACGGCAAGGACTGCCGCG  3100
CAAACACGACTTCTTCAACGCGATGGTGACGCTGCCGTTCCTGACGGCGC

AGGCGGAGGACTCCGAGGAGGAGGACGAGAAGGCGGACGGTCGGCAGGTG  3150
TCCGCCTCCTGAGGCTCCTCCTCCTGCTCTTCCGCCTGCCAGCCGTCCAC

CCCATCAGCCTGGTGCTGCTCATCCTGGCCAGCTACATCTGCGTGGGCAC  3200
GGGTAGTCGGACCACGACGAGTAGGACCGGTCGATGTAGACGCACCCGTG

CGTGATCTTCGCTCTGTGGGAGAACTGGTCGCTGGTGGACGGAGCGTACT  3250
GCACTAGAAGCGAGACACCCTCTTGACCAGCGACCACCTGCCTCGCATGA

TCTGTTTTGTTACCCTGTCGACCATTGGATACGGTGATTTTGTGCCCGCG  3300
AGACAAAACAATGGGACAGCTGGTAACCTATGCCACTAAAACACGGGCGC

CGGAGCTTTAACGGGCCTGAGTTGCAGCTATACGCCTGCTGCGCTTACTT  3350
GCCTCGAAATTGCCCGGACTCAACGTCGATATGCGGACGACGCGAATGAA

GCTTCTGGGACTCGTCCTGGTTGCGATGTCCTTCAGCATCCTGGAAACGC  3400
CGAAGACCCTGAGCAGGACCAACGCTACAGGAAGTCGTAGGACCTTTGCG

AGCTCATGTGGAAGTGCAAACGCATTGCCGTGCGACTGAAGCTGGCCCGC  3450
TCGAGTACACCTTCACGTTTGCGTAACGGCACGCTGACTTCGACCGGGCG

GCGGATGGATAA
CGCCTACCTATT
```

FIG. 8E

```
MSDVEQAIKAKQPQPSQLDCSIDDETDATEFGGLGGVGGAGCGSEMGAKT    50
TASLTAKPRSSLRRCCGHLLKLLFSTPGLVLLVIGYSVLGGLLFPLLEAP   100
QDISKSAAIAKSREDCLRELWIITEKLNVLYERNWTMLVHEQLRRFEGSI   150
VAATRQGSAGSSGGGGAGLFHEGSASALGHFGYDAGDSQSWSFSEALLYS   200
VTVITTIGHGSLTPRTAAGKLATIFYALVGVPLMLCLSSLGALLADGLQ    250
CTYVRLCCQLQRHQEHRRKSTPGTSTPSASSAANSREKDTDKRSKRRMFF   300
PPHHESFSPATKTVSFLASGKPESLVAYVWKWKAGKSGCDGNLRLSGDLL   350
SSMEFNPFFADQTALGSQITAFNYDSRSLLSGSPSRTRMRLAIDKTASRL   400
RLALGMCSHRLNYYRHRVDCCHFGFWSFALLAFAIVLAIIMTHAAVTVFR   450
RSVDTGHPRNQGDNYSALSFKCTANCKGCQYDAANSETSLNDCLEYGQKG   500
KLPPDKKEGDACQLLRNLNPQQHFYQQQQQQPQQPDVMLMTTTSGSALLK   550
YAPQQQQLQQQQQLSTATLPRQHHQMQLQQQQQQLQQNFVAVPSSMLRMP   600
LTVPPNCYAPATATIYFPFGHAPSAPGSPAHNQAHPTQNPNGNALGNTTL   650
GSQPLVKYHTIHLQPASGKHRVLASGLQDATAVNLVTASEASTSTLEAIT   700
LPPPPAYQTASVHGRSPPRMSPFNATVLIYAFNYITIFIIIIISSLQQR    750
VKMTDFQLVLLDMPGHQQQQQQGPVRRAKFVAKPLPQEINALMDCGTGSP   800
DLSGRHDLLPPPHSGSPATGTAASPLLTYTAAATSPQLSAGIKGGSGPAP   850
TAGAPMLVSGAGRGAAALTDNGFMAAGVCGMGAAAAPLPVTSMGAATTTA   900
SSAASTLSALLSANSTGNVDIMEDEDEQERERLSNCPHGTPSRVPLIASP   950
LSVPQDSGENTTRNTAFNRHTLQPLSRKTLLLTRRCHRHASGTLYDSTAN  1000
NTETSDDEEYMQHGSEQFVLKKLRYHCDGKDCREAEDSEEEDEKADGRQV  1050
PISLVLLILASYICVGTVIFALWENWSLVDGAYFCFVTLSTIGYGDFVPA  1100
RSFNGPELQLYACCAYLLLGLVLVAMSFSILETQLMWKCKRIAVRLKLAR  1150
ADG*
```

FIG. 9

```
TATCATCGCCACTGTGCTGGGAATTCGGCACGAGGGACATTCTTCGATGG  50
ATAGTAGCGGTGACACGACCCTTAAGCCGTGCTCCCTGTAAGAAGCTACC

CTTCTACTTTTGTTTCATCACCATGACAACCATCGGATTCGGTGATTTGG 100
GAAGATGAAACAAAGTAGTGGTACTGTTGGTAGCCTAAGCCACTAAACC

TGCCAAAGAAACCCAACTACATGCTACTGTGCACATTGTATATTCTTATT 150
ACGGTTTCTTTGGGTTGATGTACGATGACACGTGTAACATATAAGAATAA

GGCCTGGCCCTGACATCGACCATCATTGAGCTGGTGCGAAGGCAATATGC 200
CCGGACCGGGACTGTAGCTGGTAGTAACTCGACCACGCTTCCGTTATACG

CACCAGTTGGGCCAAGCTGCAGGAGCTATCTGGTCCCATGGCGGAGACTC 250
GTGGTCAACCCGGTTCGACGTCCTCGATAGACCAGGGTACCGCCTCTGAG

TGCGTCGCTTGGGCGAAACAGCCGGCACGGGCCTCGATTATACAGCCCTG 300
ACGCAGCGAACCCGCTTTGTCGGCCGTGCCCGGAGCTAATATGTCGGGAC

CAGAAGGTGCTTACGGTGTCCATGCCCAAATGGAATAGTAAGAAGAATAG 350
GTCTTCCACGAATGCCACAGGTACGGGTTTACCTTATCATTCTTCTTATC

CACAGTCCCGATATTGCGGCCCTGGAAGCCATCACGAATGCCATTTTGAA 400
GTGTCAGGGCTATAACGCCGGGACCTTCGGTAGTGCTTACGGTAAAACTT

GGAGGTGAAGGAGGCGCAGAACAACAAGCCGAAGGTCCTGCAGATCGTCA 450
CCTCCACTTCCTCCGCGTCTTGTTGTTCGGCTTCCAGGACGTCTAGCAGT

TATACGAGTCGTCCGTTTAGACGGAAAGGAGGGATAGAAACCAGACAGCG 500
ATATGCTCAGCAGGCAAATCTGCCTTTCCTCCCTATCTTTGGTCTGTCGC

AGATTGAGCTTCCATCGATGAAAAAGTGCTGCATAGTTTTGGGCGAGCA 550
TCTAACTCGAAGGTAGCTACTTTTTTCACGACGTATCAAAACCCGCTCGT

GGCAGAAAAGCAAAAAAAAATATATATATACATATATCAAGCGAAATAT  600
CCGTCTTTTCGTTTTTTTTTATATATATATGTATATAGTTCGCTTTATA

CAAT
GTTA
```

FIG. 10

```
YHRHCAGNSARGTFFDGFYFCFITMTTIGFGDLVPKKPNYMLLCTLYILI  50

GLALTSTIIELVRRQYATSWAKLQELSGPMAETLRRLGETAGTGLDYTAL 100

QKVLTVSMPKWNSKKNSTVPILRPWKPSRMPF
```

FIG. 11

```
ATGAAGAAACAAAATGTGCGCACGATATCCTTGATCGTGTGTACATTTAC  50
TACTTCTTTGTTTTACACGCGTGCTATAGGAACTAGCACACATGTAAATG

CTATCTGCTTGTCGGCGCCGCCGTCTTTGACGCCCTCGAATCGGAAACGG  100
GATAGACGAACAGCCGCGGCGGCAGAAACTGCGGGAGCTTAGCCTTTGCC

AAAAGCGTCGTTGGGAGGCGCTGCAAGATGCCGAGGATATGATAATACGC  150
TTTTCGCAGCAACCCTCCGCACGTTCTACGGCTCCTATACTATTATGCG

AAATACAATATCTCACAGGAGGACTTCAAAGTCATGGAGACTGTGGTGCT  200
TTTATGTTATAGAGTGTCCTCCTGAAGTTTCAGTACCTCTGACACCACGA

CAAATCGGAATCGCACAAGGCCGGCCAGCAATGGAAATTCACCGGTGCAT  250
GTTTAGCCTTAGCGTGTTCCGGCCGGTCGTTACCTTTAAGTGGCCACGTA

TCTATTATGCAACCACGGTGCTAACCACCATTGGCTACGGACACTCGACG  300
AGATAATACGTTGGTGCCACGATTGGTGGTAACCGATGCCTGTGAGCTGC

CCCAGCACGGTGGGCGGGAAGCTCTTCACCATGTGCTATGCCATCGTGGG  350
GGGTCGTGCCACCCGCCCTTCGAGAAGTGGTACACGATACGGTAGCACCC

GATTCCCCTGGGTCTCGTTATGTTCCAGAGCATCGGAGAAGAGTGAATA  400
CTAAGGGGACCCAGAGCAATACAAGGTCTCGTAGCCTCTTTCTCACTTAT

GACTGAGCAGCTATGTTATCAAGGCGGTCCGCTCCTCGCTGCGCTGCAAG  450
CTGACTCGTCGATACAATAGTTCCGCCAGGCGAGGAGCGACGCGACGTTC

AGGACCGTCGCCTCGGAGGTGGACCTCATCTGTGTTGTGACCACACTCAG  500
TCCTGGCAGCGGAGCCTCCACCTGGAGTAGACACAACACTGGTGTGAGTC

TTCGCTGACGATAGCTGGCGGTGCTGCGGCCTTTTCCAAATTTGAGGGCT  550
AAGCGACTGCTATCGACCGCCACGACGCCGGAAAAGGTTTAAACTCCCGA

GGAGCTACTTCGATTCAGTATATTACTGTTTTATTACTTTAACCACTATA  600
CCTCGATGAAGCTAAGTCATATAATGACAAATAATGAAATTGGTGATAT

GGCTTTGGCGACATGGTAGCCCTGCAGCGGGACAATGCACTGAACAGGAA  650
CCGAAACCGCTGTACCATCGGGACGTCGCCCTGTTACGTGACTTGTCCTT

GCCCGAATACGTGATGTTCGCACTGATATTTATACTATTTGGCCTGGCCA  700
CGGGCTTATGCACTACAAGCGTGACTATAAATATGATAAACCGGACCGGT

TTGTGGCCGCCTCGCTGAACTTGTTAGTACTTAGGTTTGTTACGATGAAT  750
AACACCGGCGGAGCGACTTGAACAATCATGAATCCAAACAATGCTACTTA
```

FIG. 12A

ACCGAGGATGAGCGACGCGACGAGGCCCAGGCCATGCAGGCGCTGCAAGT 800
TGGCTCCTACTCGCTGCGCTGCTCCGGGTCCGGTACGTCCGCGACGTTCA

GGCTGTGAAGCTGGAGGGCGATGTGATAACATCCAACGGATCCATTCTGA 850
CCGACACTTCGACCTCCCGCTACACTATTGTAGGTTGCCTAGGTAAGACT

GCGGCTACGAGGGACACGATGGCCAATCTCTGAACGGAAGCAACATCTCG 900
CGCCGATGCTCCCTGTGCTACCGGTTAGAGACTTGCCTTCGTTGTAGAGC

TCCATGTGCTCGTGCCACTGCATCTGCCTCAATGGCAACCGGCACAAAAA 950
AGGTACACGAGCACGGTGACGTAGACGGAGTTACCGTTGGCCGTGTTTTT

AAGTAGCAACTTGGAAAAGAACAACGATGCAGAAAATCAATACAAGCTGA 1000
TTCATCGTTGAACCTTTTCTTGTTGCTACGTCTTTTAGTTATGTTCGACT

GGCAATCGCCGACGCACATACGACACCTTCTGCCGGAGGTGGTGCCCATG 1050
CCGTTAGCGGCTGCGTGTATGCTGTGGAAGACGGCCTCCACCACGGGTAC

CAGGATTTGAACTACGACTACGATACGCAGAGCCTGCACACCCTTGCCGA 1100
GTCCTAAACTTGATGCTGATGCTATGCGTCTCGGACGTGTGGGAACGGCT

TCGTGGAACCATGGACAGCAGCTACATGGGCGTGGACATGGCGGACATGG 1150
AGCACCTTGGTACCTGTCGTCGATGTACCCGCACCTGTACCGCCTGTACC

GGGATACGGGCAGCATGGAGCTGCGGCCACACACGTTGCTCAAGCGCAAT 1200
CCCTATGCCCGTCGTACCTCGACGCCGGTGTGTGCAACGAGTTCGCGTTA

GTCTCACTGCTGTCCATACGCATCTAG
CAGAGTGACGACAGGTATGCGTAGATC

FIG. 12B

MKKQNVRTISLIVCTFTYLLVGAAVFDALESETEKRRWEALQDAEDMIIR 50

KYNISQEDFKVMETVVLKSESHKAGQQWKFTGAFYYATTVLTTIGYGHST 100

PSTVGGKLFTMCYAIVGIPLGLVMFQSIGERVNRLSSYVIKAVRSSLRCK 150

RTVASEVDLICVVTTLSSLTIAGGAAAFSKFEGWSYFDSVYYCFITLTTI 200

GFGDMVALQRDNALNRKPEYVMFALIFILFGLAIVAASLNLLVLRFVTMN 250

TEDERRDEAQAMQALQVAVKLEGDVITSNGSILSGYEGHDGQSLNGSNIS 300

SMCSCHCICLNGNRHKKSSNLEKNNDAENQYKLRQSPTHIRHLLPEVVPM 350

QDLNYDYDTQSLHTLADRGTMDSSYMGVDMADMGDTGSMELRPHTLLKRN 400

VSLLSIRI*

FIG. 13

```
ATGGACTTCTGCAACTACGGCACAGTTAATAATAACTCTTCATCCATTGG  50
TACCTGAAGACGTTGATGCCGTGTCAATTATTATTGAGAAGTAGGTAACC

GGATGACGAGGAAATCGGTTTACTTCCCAAAATTGTCGAAGGAAATCGCA  100
CCTACTGCTCCTTTAGCCAAATGAAGGGTTTTAACAGCTTCCTTTAGCGT

ACAAAATTATTGGCATGGAGAAAACTTCCTTTCGGTTTTCACTGTATTTA  150
TGTTTTAATAACCGTACCTCTTTTGAAGGAAAGCCAAAAGTGACATAAAT

TTTGCTTATTTCATGTTTTTGTGTAGCGGAGCAGCGGTTTTCAGTTACTT  200
AAACGAATAAAGTACAAAAACACATCGCCTCGTCGCCAAAAGTCAATGAA

TGAGGCACCTGAGGAACGGGCACTGAGAGTTAAACTTGGAACAGCAGTAC  250
ACTCCGTGGACTCCTTGCCCGTGACTCTCAATTTGAACCTTGTCGTCATG

AAAAATTTTTGGTGTCTAATCCTAACGTTACAGATGCAGATTTGGAAGAA  300
TTTTTAAAAACCACAGATTAGGATTGCAATGTCTACGTCTAAACCTTCTT

TTGATAGTAGAAATAGTGAGAGCAAATAATCGTGGAGTTTCAGCTATCGA  350
AACTATCATCTTTATCACTCTCGTTTATTAGCACCTCAAAGTCGATAGCT

AAATGCCACTTCAGAGCCTAATTGGAGTTTTGGTCAATCATTTTTCTTTG  400
TTTACGGTGAAGTCTCGGATTAACCTCAAAACCAGTTAGTAAAAAGAAAC

CCAGCACAGTCATCACAACTATAGGATATGGTCATGTTACTCCACTCAGC  450
GGTCGTGTCAGTAGTGTTGATATCCTATACCAGTACAATGAGGTGAGTCG

AGAAATGGTAAATTATTTTGCATGTTTTATGCCGTGGTTGGAATTCCTTT  500
TCTTTACCATTTAATAAAACGTACAAAATACGGCACCAACCTTAAGGAAA

GACTCTGGTACTGCTTTCTGCTCTCGTGGAACGATTACTGATTCCGACAG  550
CTGAGACCATGACGAAAGACGAGAGCACCTTGCTAATGACTAAGGCTGTC

TTTGGCTCTTGCAATGGCTTAATTCAAAATTAGGACACCTTTATCAGCCT  600
AAACCGAGAACGTTACCGAATTAAGTTTTAATCCTGTGGAAATAGTCGGA

CTTCGAATACGAATCGTCCATTTGGCAATTATAGTTTTAGTACTACTTGT  650
GAAGCTTATGCTTAGCAGGTAAACCGTTAATATCAAAATCATGATGAACA

ATTCTTCCTGCTACTCCCAGCTGCAATTTTTGCGTCTTTGGAACCAGAAT  700
TAAGAAGGACGATGAGGGTCGACGTTAAAAACGCAGAAACCTTGGTCTTA

GGGACTATTTGGATTCTCTTTACTATTGCTTTATATCCCTCACAACAATA  750
CCCTGATAAACCTAAGAGAAATGATAACGAAATATAGGGAGTGTTGTTAT

GGATTGGGAGACTACATTCCTGGAGATTCCGCCCACCAGCCTTACCGTCC  800
CCTAACCCTCTGATGTAAGGACCTCTAAGGCGGGTGGTCGGAATGGCAGG

TTTATACAAAATAATGACTACATGTTACCTTTTCCTGGGTATAACAATAA  850
AAATATGTTTTATTACTGATGTACAATGGAAAAGGACCCATATTGTTATT
```

FIG. 14A

```
TGATGTTGACGCTAACAGTATTTTACGATATACCCCAACTCAATTTGGGC  900
ACTACAACTGCGATTGTCATAAAATGCTATATGGGGTTGAGTTAAACCCG

CTACTCTTCACAACTAGCGAAGACTCTGAAAAAGTGAGGTTAGCCAGTTC  950
GATGAGAAGTGTTGATCGCTTCTGAGACTTTTTCACTCCAATCGGTCAAG

CGGGCCAGGTTTACAGTACGGAGCAGGTTTTAGCCCTCATAATGAAGATA 1000
GCCCGGTCCAAATGTCATGCCTCGTCCAAAATCGGGAGTATTACTTCTAT

ATATCCACCGACAAGTAGTGAGGGTTAGATCGAGACACAACGATAGTCCC 1050
TATAGGTGGCTGTTCATCACTCCCAATCTAGCTCTGTGTTGCTATCAGGG

AGTCCTGAAGAACCACCACATAAAGGATTTCCCTAA
TCAGGACTTCTTGGTGGTGTATTTCCTAAAGGGATT
```

FIG. 14B

MDFCNYGTVNNNSSSIGDDEEIGLLPKIVEGNRNKIIGMEKTSFRFSLYL 50

FAYFMFLCSGAAVFSYFEAPEERALRVKLGTAVQKFLVSNPNVTDADLEE 100

LIVEIVRANNRGVSAIENATSEPNWSFGQSFFFASTVITTIGYGHVTPLS 150

RNGKLFCMFYAVVGIPLTLVLLSALVERLLIPTVWLLQWLNSKLGHLYQP 200

LRIRIVHLAIIVLVLLVFFLLLPAAIFASLEPEWDYLDSLYYCFISLTTI 250

GLGDYIPGDSAHQPYRPLYKIMTTCYLFLGITIMMLTLTVFYDIPQLNLG 300

LLFTTSEDSEKVRLASSGPGLQYGAGFSPHNEDNIHRQVVRVRSRHNDSP 350

SPEEPPHKGFP*

FIG. 15

```
TTTTTTTTTT TTTTTTTTTT TTTTTTTTTT AAATTATCAT TGCTTTTATT TTCAATATTT 60
TTAGCACAAC AAAGAAAACG TAGCCTGATT GCATTCGATG ACAGTAGTAG TCTCCCCTTC 120
CCAGTAACCC GTTTATGTTA GTGGATTTCG GACGCTGTGT TTGTTTGGCT CTTCTGGATA 180
TTCATTTTAT CTGTATATCA ATCTTTGGAA TTTCGTACAT TTATTATTTA AATAAACTCA 240
GTATGCTATG TAAAGTTAAG GAAATCTTTA GTTCAAGTGC AGGTTTAAGA TATATCAGAA 300
GGTATTCTTA AACTTCGATA CTATTTTTTA GGGAAGAAGT GAATTTGGTT TTTTAATGAT 360
GTCATGCCTT CCAAGGAAGC GCTTTATAAT TAATATAATC TTAACTATTT TACTTATCAT 420
ATTCTCGTTT GTGAATTTAA ATTTGTTGAA GTTTTTTTCA TAAAACATTT AAACATATTA 480
AATATCCATC TTTCAAAGTG TGTTCCTTAT AATTAGAGCA TCCAACATAT TTAGGAAAAA 540
ACAGATGTCA TAACTATCTA TCTATCTATT ACTAATCCTC ATCCTGCTCG TCGTCATCAT 600
CCTTAAGAAT GCCCAGACGG CGGGCTACCT CCTTCACATT GGCAATGAAC TCCTCCTGGA 660
CCAGGTTAAA ACTCATGGCC AACAAGGCAA TGCCGAAAAG AAGGTACAGC GAGCAATAGG 720
CGATGGACTG CTCCGACTCG TCCTTGACTC CTTTCGCGGG GACAAAGTCA CCAAATCCGA 780
TTGTTGTCAG TGTAATGAAG CAAAAGTAGG CGGAATCCAA GAAGGACCAG TTCTCCCAGT 840
ACGCAAAAAG AACAGCTCCG CCAAGGATGT AGCTCACTAC CAGAAAGACG CATAACCAAA 900
TGGGGACAGG TCGATCCTTG GGCAGCAGAT CTCCATAGTC CCCATACTCA TCCCCGTACA 960
TAGAGTCATC GTCGTCGTAA TCGTAGCTGG GTCGCCGACG GATTTGCCGC TGGACCGGAA 1020
ATCCCATTGG TGACATGATT CTCGGGGAAG GGGGCAAACG TTCAGTCCGC TCCCTTCGGC 1080
GATTTCTTTT TGGTTCTCGA CTCCTTGAGT GGTGGCGCTC AGGCGGATAA TCCTCGTAGT 1140
TATTGTCTCC GTAAAGGGAT CCCTCATCGA AGCTCTCTTC CACGTAGTCC TCGTAGCGAC 1200
CCTGGGAGTG GCCACGCCTA TCCCGTCGAT GGTCCCGTCC CGGCGGTGGA GCATCATAGT 1260
CGGGAAGTTC GAGATGGTTG CCATAGCGAG ATGATTGCCT GCCCAGACTT CCAGCTCGTC 1320
TGTCATGCTG TTGGCGATAG GAGCTCTGCG GTGGCGGCTG TGGAGATCGT TCCCGTTCTC 1380
TGTCCTTCTG GCGTTGCCTT TGGTGAGCAG ACCTGGGCAT GGATTGACTC CTTGGAGCTG 1440
CTTGTCTTCT GTTGCCCCCG AAGTCATCTA AAGCATACCT ATTTGGTATA ATGGGTGTTT 1500
TCCTCACCAC GTCCTCGTCG ACGTCTTCGT AATGTGAAGA AACGTGCCTG GATCCACGG 1560
ACTTGGCCCT ACTTCTCCCA GGTGCCGAGT GAAGGCGATG CAGTTCTCTG GACGCTTTGG 1620
AAGATTCCTG ATTGTGTGGC GATCGAACCG ATCGCACACT GGCAGCTCTT TTCGCAGGAG 1680
GTTGCATGTC ACCGAAGTCC TCAATGGATC CAGCATCCAA GTGGGATCGG GAGTAGCGCT 1740
CCCTTTCTAC CGTGTGTCTG TCCCTCATCC GATCCCGTTG TCTTTGCCGG CTACTGTAGC 1800
GGTTGGATCT GTTCAGGGTC TGAGTTTCGT ACCCATCTCC GTAAATGGTG TGACGCTGGC 1860
GAGGATCGTG ATGCAAATGC TGCTGCTGCT GCTGCTGACG ACGATTCCGT CCGCCTCCAC 1920
TGCTCCGATG TCCGAACTCG CGGTCATCGT AGCCCCGGCC CATGGTGCGC AGGTCGGGAT 1980
CTGAATAGGC ATGACCCATG GAAGGACCCA GACCCGAGTC ATTCCCAGAC CGTTGGGTCC 2040
TCTTCATGGA GCGCCGGAAC GAGGGCGGCG GCTGGGATCG GGCATGGCGC TGAGAGCGCA 2100
TCGATCTCTG CCGGGATCGG GCATTCCTCG GACGTTTGGC CGTGCGGGTG CACACGTAGC 2160
AGCATATTCT CCAGTACAGA AACCGAAATG ATGTGGCCAT GACATCGCCA ATGTTGGACA 2220
AGCAGATGAG CATCAGCGGA ATGCCCACAA TGGCGTAGAA AATCGTTGTC ACCTTGCCCC 2280
AATCCGTACG CGGCGATATG TGACCATAGC CTATGGTCGT TATCACAATA ATCGAGTAGA 2340
ACAGGGATCC GGCAAAAGGT CCACTGGGAC TTGCGCAGAT CCTCGTCGCC ATCCCAGCCG 2400
TCGGCCTTGA TGGCCGTAAG GATTTGCTTT TCAAAATTGG CCAGGTGCTT GCTGACATTG 2460
GCCATCCAAT CGCTTTCCCT TAGGACCACT GCGTCGTCGG ACAGTAGCCA GATATTCTCC 2520
```

FIG. 16A

```
GTGAGATTAA CGCGAAGATT CTGTATGTCT CGCTTCACCT CCAGTTCGTG GGGTCGTTCG 2580
AGGTGCTGGA AGAGGTAGGC ACCGCCCACG CAATAGGAAA CCACGAGGAG CACGAGCAGC 2640
ACATGGGACA CAATGCAGGT GAGCACCTTC CACGAGAAGC AGATGGCAGC CACACAGCGT 2700
CCGCGTTGCG GCTTCGCTGG CTCCAACATG TGCGCCGGCA GAGATTGGGC CCGCCTACCC 2760
GACATGGTCA CCCTCCTCTG GCCTCCTCCT TCCTTTGGCT AATTTGCCGC TCGGTTGGCG 2820
ATCGCTGATC GCCTTCTGAT TCGCACTGAG GAAAAATTTT CAGTTTTCCA CATTAAGTTC 2880
CATGCTGTAT ACTTTGCCCG CACTCTCCCG TCTTCCGTCT AACAATCCGT TTCCGATTCT 2940
ATATCCGATG GGATCCGTAC AGAGAAAAGA AGCACCGATC CGTAACCTGC CCGGGCGGCC 3000
GCTCGAGCCC TATAGTGAGT CGTATTAGGA TGG 3033
```

FIG. 16B

```
Pro Lys Glu Gly Gly Gly Gln Arg Arg Val Thr Met Ser Gly Arg Arg
Ala Gln Ser Leu Pro Ala His Met Leu Glu Pro Ala Lys Pro Gln Arg
Gly Arg Cys Val Ala Ala Ile Cys Phe Ser Trp Lys Val Leu Thr Cys
Ile Val Ser His Val Leu Leu Val Leu Leu Val Val Ser Tyr Cys Val
Gly Gly Ala Tyr Leu Phe Gln His Leu Glu Arg Pro His Glu Leu Glu
Val Lys Arg Asp Ile Gln Asn Leu Arg Val Asn Leu Thr Glu Asn Ile
Trp Leu Leu Ser Asp Asp Ala Val Leu Arg Glu Ser Asp Trp Met
Ala Asn Val Ser Lys His Leu Ala Asn Phe Glu Lys Gln Ile Leu Thr
Ala Ile Lys Ala Asp Gly Trp Asp Gly Asp Glu Asp Leu Arg Lys Ser
Gln Trp Thr Phe Ala Gly Ser Leu Phe Tyr Ser Ile Ile Val Ile Thr
Thr Ile Gly Tyr Gly His Ile Ser Pro Arg Thr Asp Trp Gly Lys Val
Thr Thr Ile Phe Tyr Ala Ile Val Gly Ile Pro Leu Met Leu Ile Cys
Leu Ser Asn Ile Gly Asp Val Met Ala Thr Ser Phe Arg Phe Leu Tyr
Trp Arg Ile Cys Cys Tyr Val Cys Thr Arg Thr Ala Lys Arg Pro Arg
Asn Ala Arg Ser Arg Gln Arg Ser Met Arg Ser Gln Arg His Ala Arg
Ser Gln Pro Pro Pro Ser Phe Arg Arg Ser Met Lys Arg Thr Gln Arg
Ser Gly Asn Asp Ser Gly Leu Gly Pro Ser Met Gly His Ala Tyr Ser
Asp Pro Asp Leu Arg Thr Met Gly Arg Gly Tyr Asp Asp Arg Glu Phe
Gly His Arg Ser Ser Gly Gly Gly Arg Asn Arg Arg Gln Gln Gln Gln
Gln Gln His Leu His His Asp Pro Arg Gln Arg His Thr Ile Tyr Gly
Asp Gly Tyr Glu Thr Gln Thr Leu Asn Arg Ser Asn Arg Tyr Ser Ser
Arg Gln Arg Gln Arg Asp Arg Met Arg Asp Arg His Thr Val Glu Arg
Glu Arg Tyr Ser Arg Ser His Leu Asp Ala Gly Ser Ile Glu Asp Phe
Gly Asp Met Gln Pro Pro Ala Lys Arg Ala Ala Ser Val Arg Ser Val
Arg Ser Pro His Asn Gln Glu Ser Ser Lys Ala Ser Arg Glu Leu His
Arg Leu His Ser Ala Pro Gly Arg Ser Arg Ala Lys Ser Val Asp Pro
Arg His Val Ser Ser His Tyr Glu Asp Val Asp Glu Asp Val Val Arg
Lys Thr Pro Ile Ile Pro Asn Arg Tyr Ala Leu Asp Asp Phe Gly Gly
Asn Arg Arg Gln Ala Ala Pro Arg Ser Gln Ser Met Pro Arg Ser Ala
His Gln Arg Gln Arg Gln Lys Asp Arg Glu Arg Glu Arg Ser Pro Gln
Pro Pro Pro Gln Ser Ser Tyr Arg Gln Gln His Asp Arg Arg Ala Gly
Ser Leu Gly Arg Gln Ser Ser Arg Tyr Gly Asn His Leu Glu Leu Pro
Asp Tyr Asp Ala Pro Pro Pro Gly Arg Asp His Arg Arg Asp Arg Arg
Gly His Ser Gln Gly Arg Tyr Glu Asp Tyr Val Glu Glu Ser Phe Asp
Glu Gly Ser Leu Tyr Gly Asp Asn Asn Tyr Glu Asp Tyr Pro Pro Glu
Arg His His Ser Arg Ser Arg Glu Pro Lys Arg Asn Arg Arg Arg Glu
Arg Thr Glu Arg Leu Pro Pro Ser Pro Arg Ile Met Ser Pro Met Gly
Phe Pro Val Gln Arg Gln Ile Arg Arg Arg Pro Ser Tyr Asp Tyr Asp
Asp Asp Asp Ser Met Tyr Gly Asp Glu Tyr Gly Asp Tyr Gly Asp Leu
Leu Pro Lys Asp Arg Pro Val Pro Ile Trp Leu Cys Val Phe Leu Val
Val Ser Tyr Ile Leu Gly Gly Ala Val Leu Phe Ala Tyr Trp Glu Asn
Trp Ser Phe Leu Asp Ser Ala Tyr Phe Cys Phe Ile Thr Leu Thr Thr
```

FIG. 17A

```
Ile Gly Phe Gly Asp Phe Val Pro Ala Lys Gly Val Lys Asp Glu Ser
Glu Gln Ser Ile Ala Tyr Cys Ser Leu Tyr Leu Leu Phe Gly Ile Ala
Leu Leu Ala Met Ser Phe Asn Leu Val Gln Glu Glu Phe Ile Ala Asn
Val Lys Glu Val Ala Arg Arg Leu Gly Ile Leu Lys Asp Asp Asp Asp
Glu Gln Asp Glu Asp
```

FIG. 17B

```
GCACATGGAC GAGATGTTGC TTCCGTTCAG AGATTGGCCA TCGTGTCCCT CGTAGCCGCT   60
CAGAATGGAT CCGTTGGATG TTATCACATC GCCCTCCAGC TTCACAGCCA CTTGCAGCGC  120
CTGCATGGCC TGGGCCTCGT CGCGTCGCTC ATCCTCGGTA TTCATCGTAA CAAACCTAAG  180
TACTAACAAG TTCAGCGAGG CGGCCACAAT GGCCAGGCCA AATAGTATAA ATATCAGTGC  240
GAACATCACG TATTCGGGCT TCCTGTTCAG TGCATTGTCC CGCTGCAGGG CTACCATGTC  300
GCCAAAGCCT ATAGTGGTTA AAGTAATAAA ACAGTAATAT ACTGAATCGA AGTAGCTCCA  360
GCCCTCAAAT TTGGAAAAGG CCGCAGCACC GCCAGCTATC GTCAGCGAAC TGAGTGTGGT  420
CACAACACAG ATGAGGTC
```

FIG. 18

```
Asp Leu Ile Cys Val Val Thr Thr Leu Ser Ser Leu Thr Ile Ala Gly
Gly Ala Ala Ala Phe Ser Lys Phe Glu Gly Trp Ser Tyr Phe Asp Ser
Val Tyr Tyr Cys Phe Ile Thr Leu Thr Thr Ile Gly Phe Gly Asp Met
Val Ala Leu Gln Arg Asp Asn Ala Leu Asn Arg Lys Pro Glu Tyr Val
Met Phe Ala Leu Ile Phe Ile Leu Phe Gly Leu Ala Ile Val Ala Ala
Ser Leu Asn Leu Leu Val Leu Arg Phe Val Thr Met Asn Thr Glu Asp
Glu Arg Arg Asp Glu Ala Gln Ala Met Gln Ala Leu Gln Val Ala Val
Lys Leu Glu Gly Asp Val Ile Thr Ser Asn Gly Ser Ile Leu Ser Gly
Tyr Glu Gly His Asp Gly Gln Ser Leu Asn Gly Ser Asn Ile Ser Ser
Met Cys
```

FIG. 19

```
GACGCACATA CGACACCTTC TGCCGGAGGT GGTGCCCATG CAGGATTTGA ACTACGACTA  60
CGATACGCAG AGCCTGCACA CCCTGGCCGA TCGTGGAACC ATGGACAGCA GCTACATGGG 120
CGTGGACATG GCGGACATGG GGGATACGGG CAGCATGGAG CTGCGGCCAC ACACGTTGCT 180
CAAGCGCAAT GTCTCACTGC TGTCCATACG CATCTAGGCG GCGATGTCGT CATCTGCGGA 240
CGGCGGTGGA GGATTGGCGG GTACCGGGAA CAACGAAGTG GCCCACGACC TTGCCAAAAA 300
CGACTTACAA ATCGAAAGTG ATAACAAGGC TCTAATAGTA CTTAAATACT TATGGTAGAT 360
TCGCAACTGA CGATTAATTG ATCGTTGGAT TGATTGACCT GTGCGATAGT TTGTGTAGGC 420
TCCACCCGCG ACTTGGACAC GCCATGTGTG TGCATTTACA A
```

FIG. 20

NUCLEIC ACIDS AND POLYPEPTIDES OF INVERTEBRATE TWIK CHANNELS AND METHODS OF USE

RELATED APPLICATIONS

This application is a continuation-in-part of pending U.S. application Ser. No. 09/270,767 filed Mar. 17, 1999. The contents of the prior application are incorporated herein by reference in their entirety.

1. FIELD OF THE INVENTION

The invention relates to novel invertebrate TWIK channel nucleic acid and polypeptide sequences and their uses in genetic screens and compound screening.

2. BACKGROUND OF THE INVENTION

Potassium channels are present in virtually all living cells, and are the most diverse class of ion channels. They conduct the flux of potassium ions through the membrane, and in doing so, are involved in the control of numerous cellular functions, such as neuronal firing, muscle contraction, volume regulation, cellular proliferation, and hormone secretion (Rudy, Neuroscience (1988) 25:729–749; Hille in: ionic Channels in Excitable Membranes, $2^{nd}$ Ed. (1992) Sinauer Associates, Inc., Sunderland, Mass.). Two characteristic features of this class of channels are pore-forming (P) domains that have a conserved sequence motif, and at least two transmembrane (TM) domains. It is believed that four P domains contribute to the formation of a functional potassium-conducting pore (MacKinnon, Nature (1991) 350:232–235; Yang et al., Neuron (1995) 15:1441–1447; Doyle et al., Science (1998) 280:69–77).

There are three structural classes of potassium channels, based on their protein encoding subunits, and defined by the number of TM and P domains: 1) voltage-gated, Shaker-like outward rectifier $K^+$ channels are characterized by the presence of six TM domains and one P domain; 2) inward rectifier, G-protein-coupled $K^+$ channels are characterized by 2 TM domains and one P domain; and 3) tandem pore domain weak inward rectifying $K^+$ (TWIK) channels, depicted in FIG. 1, are characterized by the presence of four TM domains and two P domains. The P domains of the TWIK channels are separated by the second and third TM domains. Although all members of this family have a conserved core region between the first and fourth TM domains, the—and C-terminal domains are quite diverse. The TWIK-related channels, TREK-1, TASK (also called cTBAK-1), and TRAAK exhibit the same overall structure, despite their low similarity at the amino acid level (Fink et al., EMBO J (1996) 15:6854–6862; Duprat et al., EMBO J. (1997) 16:5464–5471; Fink et al., EMBO J.(1998) 17:3297–3308; Leonoudakis et al., J. Neurosci. (1998) 18:868–877; Kim et al., Circ. Res. (1998) 82:513–518). Some TWIK family members are known to dimerize through the presence of a disulfide bridge (Lesage et al., EMBO J. (1996) 15:6400–6407), and seem to be involved in the generation and modulation of the resting potential of many cell types (Lesage and Lazdunski in: Potassium Ion Channels: Molecular Structure, Function, and Diseases (1998), Kurachi et al., eds., Academic Press, San Diego, Calif.). TWIK channels are widespread in mammals (Lesage et al., EMBO J. (1996) 15:1004–1011; Chavez et al., J. Biol. Chem. (1999) 274:7887–7892) and in *Caenorhabditis elegans* (hereinafter "*C. elegans*"; Wei et al., Neuropharmacology (1996) 35:805–829). To date, however, only one TWIK channel from *Drosophila melanogaster* has been reported (Goldstein et al., PNAS (1996) 93:13256–13261; U.S. Pat. No. 5,559,026); and there have been no further reports of TWIK channels in other insect species.

Pesticide development has traditionally focused on the chemical and physical properties of the pesticide itself, a relatively time-consuming and expensive process. As a consequence, efforts have been concentrated on the modification of pre-existing, well-validated compounds, rather than on the development of new pesticides. A promising alternative is to identify and validate biological targets against which potential ligands can be screened (Margolis and Duyk, Nature Biotech. (1998) 16:311). Production of new compounds that are safer, selective, and more efficient can be implemented using target-based discovery approaches. Further, identifying molecular diversity addressing such targets may be exploited via combinatorial chemistry and high-throughput screening. High-throughput assays can be run rapidly and inexpensively and, due to their scale, allow access to the structural variety granted by combinatorial chemistry. In addition, potential lead compounds can be directly counter-screened on the same target cloned from human or beneficial insect sources to exclude broad spectrum toxins. The essential functions of target genes in insects and nematodes may be tested directly using powerful genetic methods, eliminating the costly uncertainty of whether or not a specific gene or biochemical activity might be a pesticide target. The phenotypic consequence of genetically modulating target gene activity serves as a surrogate for chemical inhibition or activation of a protein target. Thus, genes that kill the organism when overexpressed or knocked out represent first-stage validated targets. To identify compounds that have the same effect on the organism, high-throughput screening assays are established to test compounds for their ability to interfere in vitro with the normal activity of the target. Biological definition of targets provides the opportunity to optimize chemistry around validated targets. Ion channels are validated targets of insecticide action. A significant portion of commercial insecticides are targeted towards GABA-gated chloride channels and voltage-gated sodium channels. Potassium channels, as a diverse group, have yet to be fully exploited as targets for insecticidal agents.

Potassium ion channels are involved in numerous cellular functions in a variety of cell types, and recent advances in genomics and physiology have identified several potassium channels that are involved in human diseases (Doyle et al., Trends. Genet. (1998) 14:92–98). In particular, members of the TWIK family show strong expression in the brain and the heart, followed by expression in the kidney and the muscle (Lesage et al., supra), and thus, could be implicated in epilepsy, cardiac pathologies (arrhythmias), vascular defects, neurodegenerative disorders, endocrinopathies, hormone secretion and muscular defects, and genetic diseases. The growing body of information regarding the modular subunits and the high-resolution structural of these channels features (Doyle et al., Science (1998) 280:69–77) provide critical information for validation of potassium channels as drug targets. The identification of novel TWIK orthologues in model organisms such as *Drosophila melanogaster* and other insect species would provide tools for genetic and molecular study and validation of these molecules as potential pesticide or pharmaceutical targets.

3. SUMMARY OF THE INVENTION

The present invention relates to the identification and characterization of novel TWIK channels in *Drosophila melanogaster* and *Leptinotarsa decemlineata*. Isolated nucleic acid molecules are provided that encode TWIK channel proteins or novel fragments or derivatives thereof. Vectors and host cells comprising the TWIK channel nucleic acid molecules are also described, as well as metazoan invertebrate organisms (e.g. insects, coelomates and pseudocoelomates) that are genetically modified to express or mis-express a TWIK channel protein.

An important utility of the novel TWIK channel nucleic acids and proteins of the present invention is that they can be used in screening assays to identify candidate compounds which are potential pesticidal agents or therapeutics that interact with TWIK channel proteins. Such assays typically comprise contacting a TWIK channel protein or fragment with one or more candidate molecules, and detecting any interaction between the candidate compound and the TWIK channel protein. The assays may comprise administering the candidate molecules to cultured host cells that have been genetically engineered to express the TWIK channel proteins, or alternatively, administering the candidate compound to a metazoan invertebrate organism that has been genetically engineered to express a TWIK channel protein.

The genetically engineered metazoan invertebrate animals of the invention can also be used in methods for studying TWIK channel activity. These methods typically involve detecting the phenotype caused by the expression or mis-expression of the TWIK channel protein. The methods may additionally comprise observing a second animal that has the same genetic modification as the first but additionally comprises a mutation in a gene of interest. Differences, if any, between the phenotypes of the two animals identifies the gene of interest as capable of modifying the function of the gene encoding the TWIK channel protein.

4. BRIEF DESCRIPTION OF FIGURES

FIGS. 2A–2D show a cDNA sequence (SEQ ID NO: 1) encoding Drosophila TWIK2.

FIG. 3 shows the predicted amino acid sequence (SEQ ID NO:2) of Drosophila TWIK2.

FIGS. 4A–4C show a cDNA sequence (SEQ ID NO:3) encoding Drosophila TWIK3.

FIG. 5 shows the predicted amino acid sequence (SEQ ID NO:4) of Drosophila TWIK3.

FIGS. 6A–6B show a cDNA sequence (SEQ ID NO:5) encoding Drosophila TWIK4.

FIG. 7 shows the predicted amino acid sequence (SEQ ID NO:6) of Drosophila TWIK4.

FIGS. 8A–8E show a cDNA sequence (SEQ ID NO:7) encoding Drosophila TWIK5.

FIG. 9 shows the predicted amino acid sequence (SEQ ID NO:8) of Drosophila TWIK5.

FIG. 10 shows a cDNA sequence encoding a fragment of Drosophila TWIK6 (SEQ ID NO:9).

FIG. 11 shows the predicted amino acid sequence (SEQ ID NO:10) of a polypeptide fragment of Drosophila TWIK6.

FIGS. 12A–12B show a cDNA sequence (SEQ ID NO:11) encoding Drosophila TWIK7.

FIG. 13 shows the predicted amino acid sequence (SEQ ID NO:12) of Drosophila TWIK7.

FIGS. 14A–14B show a cDNA sequence (SEQ ID NO:13) encoding *Leptinotarsa decemlineata* TWIK1.

FIG. 15 shows the predicted amino acid sequence (SEQ ID NO:14) of *Leptinotarsa decemlineata* TWIK1.

FIGS. 16A–16B show a cDNA sequence (SEQ ID NO:66) that is greater than 99% identical to the cDNA sequence encoding Drosophila TWIK3 (SEQ ID NO:3).

FIGS. 17A–17B show the predicted amino acid sequence (SEQ ID NO:67) of the cDNA sequence of FIGS. 16A–16B (SEQ ID NO:66), which is greater than 99% identical to the predicted amino acid sequence for Drosophila TWIK3 (SEQ ID NO:4).

FIG. 18 shows a cDNA sequence (SEQ ID NO:68) that is 100% identical to nucleotides 909 to 472 of the cDNA sequence encoding Drosophila TWIK7 (SEQ ED NO:11).

FIG. 19 shows the predicted amino acid sequence (SEQ ID NO:69) of the cDNA sequence of FIG. 18 (SEQ ID NO:68), which is 100% identical to amino acid residues 158 to 303 of the predicted amino acid sequence for Drosophila TWIK7 (SEQ ID NO: 12).

FIG. 20 shows a cDNA sequence (SEQ ID NO:70) of which nucleotides 1 to 217 share greater than 99% sequence identity with nucleotides 1011 to 1227 of the cDNA sequence encoding Drosophila TWIK7 (SEQ ID NO:11).

5. DETAILED DESCRIPTION OF THE INVENTION

Figure 1:
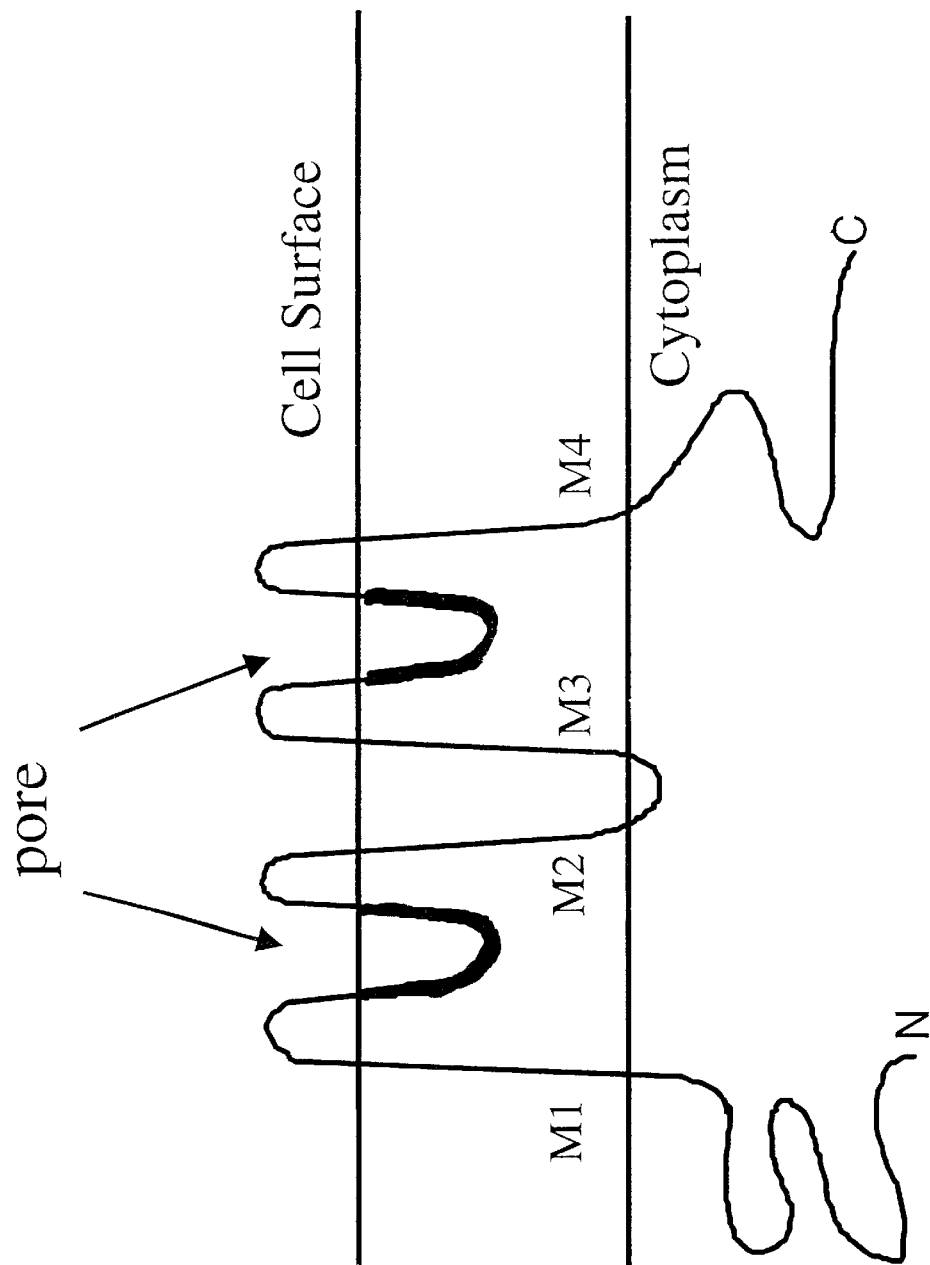
FIG. 1 depicts a representative TWIK channel.

The use of invertebrate model organism genetics and related technologies can greatly facilitate the elucidation of biological pathways (Scangos, Nat. Biotechnol. (1997) 15:1220–1221; Margolis and Duyk, supra). Of particular use is the insect model organism, *Drosophila melanogaster* (hereinafter referred to generally as "Drosophila"). An extensive search for TWIK channel nucleic acids and their encoded proteins in Drosophila and *Leptinotarsa decemlineata* (Colorado Potato Beetle, hereinafter referred to as "Leptinotarsa") was conducted in an attempt to identify new and useful tools for probing the function and regulation of the TWIK channel genes, and for use as targets in pesticide and drug discovery. Novel TWIK channel nucleic acids and their encoded proteins are identified herein. These newly identified TWIK channel nucleic acids can be used for the generation of mutant phenotypes in animal models or in living cells that can be used to study the ion channels, their regulation, and their use as pesticide or drug targets. The use of invertebrate model organisms such as Drosophila for analyzing the expression and mis-expression of TWIK channel proteins has great utility toward the identification of drug targets or mechanism of drug action, due to the ability to rapidly carry out large-scale, systematic genetic screens as well as the ability to screen small molecule libraries directly on whole organisms. Thus, the invention provides a superior approach for identifying other components involved in the synthesis, activity, and regulation of TWIK channel proteins. Systematic genetic analysis of TWIK channels using invertebrate model organisms can lead to the identification and validation of pesticide targets directed to components of the TWIK channel pathway. Additionally, these invertebrate model organisms can be used for the screening and identification of new drug targets, therapeutic agents, diagnostics and prognostics useful in the treatment of disorders associated with ion channels.

The details of the conditions used for the identification and/or isolation of each novel TWIK channel nucleic acid and protein are described in the Examples section below. Various non-limiting embodiments of the invention, applications and uses of these novel TWIK channel genes and proteins are discussed in the following sections. The entire contents of all references, including patent applications, cited herein are incorporated by reference in their entireties for all purposes. Additionally, the citation of a reference in the preceding background section is not an admission of prior art against the claims appended hereto.

5.1. TWIK Channel Nucleic Acids

The invention relates generally to TWIK channel nucleic acid, and more particularly TWIK channel nucleic acid sequences of Drosophila and Leptinotarsa, and methods of using these sequences. As described in the Examples below, the present invention provides nucleic acid sequences (SEQ ID NO:1, 3, 5, 7, 9, and 11) that were isolated from Drosophila and encode TWIK channel homologues referred to herein as TWIK2, TWIK3, TWIK4, TWIK5, TWIK6, and TWIK7, respectively. The invention also provides a nucleic acid sequence (SEQ ID NO:13) isolated from Leptinotarsa that encodes a TWIK channel referred to herein as "cpbTWIK1". In addition to the fragments and derivatives of SEQ ID NOs 1, 3, 5, 7, 9, 11, and 13 as described in detail below, the invention includes the reverse complements thereof. Also, the subject nucleic acid sequences, derivatives and fragments thereof may be RNA molecules comprising the nucleotide sequence of any one of SEQ ID NOs 1, 3, 5, 7, 9, 11, and 13 (or derivative or fragment thereof) wherein the base U (uracil) is substituted for the base T (thymine). The DNA and RNA sequences of the invention can be single- or double-stranded. Thus, the term "isolated nucleic acid sequence", as used herein, includes the reverse complement, RNA equivalent, DNA or RNA single- or double-stranded sequences, and DNA/RNA hybrids of the sequence being described, unless otherwise indicated.

Fragments of these TWIK channel nucleic acid sequences can be used for a variety of purposes, for example, as nucleic acid hybridization probes and replication/amplification primers. Certain "antisense" fragments, i.e. that are reverse complements of portions of the coding sequences set forth in any one of SEQ ID NOs: 1, 3, 5, 7, 9, 11, and 13, have utility in inhibiting the function of TWIK channel genes and proteins. The fragments are of length sufficient to specifically hybridize with the corresponding SEQ ID NO 1, 3, 5, 7, 9, 11, or 13. In particular, the invention provides fragments of at least 12, preferably at least 24, more preferably at least 36, and more preferably at least 96 contiguous nucleotides of any one of SEQ ID NOs: 1, 3, 5, 7, 9, 11, and 13. When the fragments are flanked by other nucleic acid sequences, the total length of the combined nucleic acid sequence is usually less than 15 kb, preferably less than 10 kb or less than 5 kb, more preferably less than 2 kb, and in some embodiments, preferably less than 500 bases.

Preferred fragments of TWIK2 (SEQ ID NO:1) include those having at least 1791 contiguous nucleotides of SEQ ID NO:1, and more preferably at least 1796 nucleotides. Another preferred fragment comprises or consists of a sequence that encodes one of the P domains which are located at approximately nucleotides 1902–1971 and 2433–2499 of SEQ ID NO:1. Other possible fragments include those that encode TM domains which are located at approximately nucleotides 1668–1716, 2028–2076, 2412–2460, and 2568–2616 of SEQ ID NO:1. Other preferred fragments comprise any one of the following contiguous sequences of SEQ ID NO:1: nucleotides 1–1796, 1791–1803, 1786–1954, 1949–1961, and 1944–2988.

Preferred fragments of TWIK3 (SEQ ID NO:3) include those having at least 1403 contiguous nucleotides of SEQ ID NO:3, and more preferably at least 1408 nucleotides. In another embodiment of the invention, a fragment containing approximately nucleotides 405–477, or 1938–2007 of SEQ ID NO:3, which encode the P domains. In a further embodiment of the invention, a fragment containing approximately any of nucleotides 102–150, 507–555, 1902–1950, or 2076–2124 of SEQ ID NO:3, which encode the TM domains. Other preferred fragments comprise any one of the following contiguous sequences of SEQ ID NO:3: nucleotides 1–216, 207–457, 448–588, 579–1992, and 1983–2193.

Preferred fragments of TWIK4 (SEQ ID NO:5) include those having at least 350 contiguous nucleotides of SEQ ID NO:5, and more preferably at least 355 nucleotides. In another embodiment of the invention, a fragment containing approximately nucleotides 381–453, or 933–1002 of SEQ ID NO:5, which encode the P domains. In a further embodiment of the invention, a fragment containing approximately any of nucleotides 102–150, 477–525, 861–909, or 1065–1113 of SEQ ID NO:5, which encode the TM domains. Other preferred fragments comprise any one of the following contiguous sequences of SEQ ID NO:5: nucleotides 1–311, 306–318, 302–661, 656–668, 652–896, 891–903, 887–1018, 1013–1025, 1009–1122, 1117–1129, and 1112–1188.

Preferred fragments of TWIK5 (SEQ ID NO:7) include those having at least 660 contiguous nucleotides of SEQ ID NO:7, and more preferably at least 665 nucleotides. In another embodiment of the invention, a fragment containing approximately nucleotides 573–642, or 3228–3297 of SEQ ID NO:7, which encode the P domains. In a further embodiment of the invention, a fragment containing approximately any of nucleotides 222–282, 663–723, 3147–3210, or 3339–3411 of SEQ ID NO:7, which encode the TM domains.

Other preferred fragments comprise any one of the following contiguous sequences of SEQ ID NO:7: nucleotides 1–372, 368–629, 620–898, 889–1161, 1152–1354, 1345–1425, 1416–1532, 1523–2146, 2137–2269, 2260–2325, 2316–2806, 2797–3462.

Preferred fragments of TWIK6 (SEQ ID NO:9) include those that comprise or consist of approximately nucleotides 45–105, encoding a P domain, and approximately nucleotides 124–191, encoding a TM domain.

Preferred fragments of TWIK7 (SEQ ID NO:11) include those having at least 440 contiguous nucleotides of SEQ ID NO:11, and more preferably at least 445 nucleotides. In another embodiment of the invention, a fragment containing approximately nucleotides 234–303, or 552–621 of SEQ ID NO:11, which encode the P domains. In a further embodiment of the invention, a fragment containing approximately any of nucleotides 27–75, 327–375, 483–531, or 672–720 of SEQ ID NO:11, which encode the TM domains. Other preferred fragments comprise any one of the following contiguous sequences of SEQ ID NO:11: nucleotides 1–131, 126–138, 122–288, 283–295, 279–412, 407–419, 403–606, 601–613, 597–792, 787–799, 783–954, 949–961, 945–987, 982–994, and 978–1231. Other preferred fragments of TWIK7 comprise at least 14, preferably at least 39, and more preferably at least 64 contiguous nucleotides of nucleotides 472 to 909 of SEQ ID NO:11, which correspond to SEQ ID NO:68.

Preferred fragments of cpbTWIK1 (SEQ ID NO:13) include those containing approximately residues 561–633, or 891–963 of SEQ ID NO:13, which encode the P domains. In another preferred embodiment of the invention, a fragment containing approximately any of nucleotides 324–366, 654–714, 798–879, or 1008–1074 of SEQ ID NO:13, which encode the TM domains.

The subject nucleic acid sequences may consist solely of any one of SEQ ID NOs:1, 3, 5, 7, 9, 11, or 13, or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide (s) other than that which it is joined to on a natural chromosome.

The invention also provides derivative nucleic acid sequences which hybridize to the nucleic acid sequence of any one of SEQ ID NOs:1, 3, 5, 7, 9, 11, and 13 under stringency conditions such that each hybridizing derivative nucleic acid is related to the subject nucleic acid by a certain degree of sequence identity. The temperature and salt concentrations at which hybridizations are performed have a direct effect on the results that are obtained. With "stringent" or "high stringency" conditions, a denaturing agent, such as formamide, is used during hybridization. The formamide is typically used at 25% to 50% (v/v) in a buffered diluent comprising 1× to 6×SSC (1×SSC is 150 mM NaCl and 15 mM sodium citrate; SSPE may be substituted for SSC, 1×SSPE is 150 mM NaCl, 10 mM Na H2PO4, and 1.25 mM EDTA, pH7.4). The hybridization temperature is typically about 42° C. High stringency conditions also employ a wash buffer with low ionic strength, such as 0.1× to about 0.5× SSC, at relatively high temperature, typically greater than about 55° C. up to about 70° C. Moderately stringent conditions typically use 0% to 25% formamide in 1× to 6× SSC, and use reduced hybridization temperatures, usually in the range of about 27° C. to about 40° C. The wash buffer can have increased ionic strength, e.g. about 0.6× to about 2×SSC, and is used at reduced temperatures, usually from about 45° C. to about 55° C. With "non-stringent" or "low stringency" hybridization conditions, the hybridization buffer is the same as that used for moderately stringent or high stringency, but does not contain a denaturing agent. A reduced hybridization temperature is used, typically in the range of about 25° C. to about 30° C. The wash buffer has increased ionic strength, usually around 2× to about 6×SSC, and the wash temperature is in the range of about 35° C. to about 47° C. Procedures for nucleic acid hybridizations are well-known in the art (Ausubel et al., Current Protocols in Molecular Biology (1995) Wiley Interscience Publishers; Sambrook et al., Molecular Cloning: A Laboratory Manual (1989) Cold Spring Harbor Press, New York; Shilo and Weinberg, PNAS (1981) 78:6789–6792).

In a specific embodiment of the invention, nucleic acids are provided that are capable of hybridizing to any one of SEQ ID NOs:1, 3, 5, 7, 9, 11, and 13, or the above-specified fragments thereof, under any one of the hybridization conditions listed in Table 1. Hybridization conditions 8–10, as listed in Table 1, are generally considered "high stringency" conditions; conditions 4–7 are generally considered "moderately stringent", and conditions 1–3 are considered "non-stringent".

TABLE I

| Condition # | Hybridization Buffer | Hybridization Temperature | Wash Buffer | Wash Temperature |
|---|---|---|---|---|
| 1 | 6X SSC/0% formamide | 25° C. | 4X SSC | 35° C. |
| 2 | 6X SSC/0% formamide | 25° C. | 4X SSC | 40° C. |
| 3 | 6X SSC/0% formamide | 27° C. | 4X SSC | 47° C. |
| 4 | 6X SSC/0% formamide | 34° C. | 2X SSC | 45° C. |
| 5 | 6X SSC/0% formamide | 40° C. | 0.8X SSC | 45° C. |
| 6 | 3X SSC/0% formamide | 40° C. | 0.6X SSC | 50° C. |
| 7 | 1X SSC/0% formamide | 40° C. | 0.6X SSC | 55° C. |
| 8 | 6X SSC/25% formamide | 42° C. | 0.5X SSC | 60° C. |
| 9 | 2X SSC/25% formamide | 42° C. | 0.4X SSC | 65° C. |
| 10 | 1X SSC/25% formamide | 42° C. | 0.3X SSC | 70° C. |

Condition #1 shown in Table 1 is designed to isolate nucleic acids having at least about 50% sequence identity with the target nucleic acid (with % identity calculated as described below). With each subsequent condition, the stringency is such that the isolated nucleic acid has a sequence identity of at least 5% greater than what would be isolated by using the next lower condition number. Thus, for example, condition #2 is designed to isolate nucleic acids having at least about 55% sequence identity with the target nucleic acid, and conditions #9 and #10 are designed to isolate nucleic acids having at least about 90% and 95% sequence identity, respectively, to the target nucleic acid. Preferably, each hybridizing derivative nucleic acid has a length that is at least 30% of the length of the subject nucleic acid sequence described herein to which it hybridizes. More preferably, the hybridizing nucleic acid has a length that is at least 50%, still more preferably at least 70%, and most preferably at least 90% of the length of the subject nucleic acid sequence to which it hybridizes.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410, hereinafter referred to generally as "BLAST") with all the search parameters set to default values. The HSP S and HSP S2 parameters are dynamic values and are established by the program itself depending upon the composition of the particular sequence and composition of the particular database against which the sequence of interest is being searched.

A percent (%) nucleic acid sequence identity value is determined by the number of matching identical nucleotides divided by the sequence length for which the percent identity is being reported. Preferably, derivative nucleic acid sequences of the present invention have at least 70%, preferably at least 80%, more preferably at least 85%, still more preferably at least 90%, and most preferably at least 95% sequence identity with any one of SEQ ID NOs:1, 3, 5, 7, 9, 11, and 13. A preferred derivative of TWIK7 comprises at least 13, preferably at least 38, and more preferably at least 63 contiguous nucleotides 1–217 of SEQ ID NO:70, which is greater than 99% identical to nucleotides 1011 to 1227 of SEQ ID NO:11. Another preferred derivative of TWIK7 has at least 63.2%, preferably at least 66.2%, and more preferably at least 73.2% sequence identity with any contiguous 125 bases of nucleotides 1011 to 1227 of SEQ ID NO:11. Another preferred derivative has at least 64.8%, preferably at least 67.8%, and more preferably at least 74.8% sequence identity with any contiguous 125 bases of nucleotides 472 to 909 of SEQ ID NO:11, which corresponds to SEQ ID NO:68. Another preferred derivative has at least 57.5%, preferably at least 60.5%, and more preferably at least 67.5% sequence identity with any contiguous 275 bases of nucleotides 472 to 909 of SEQ ID NO:11. In some preferred embodiments, the derivative nucleic acid encodes a polypeptide comprising a TWIK channel amino acid sequence of any one of SEQ ID NOs:2, 4, 6, 8, 10, 12, and 14, or a fragment thereof. If a fragment of a TWIK channel amino acid sequence is encoded, preferably it is a functionally active fragment (e.g. a P domain, TM domain, antigenic determinant, etc.). Various domains, signals, and other functional subunits of TWIK channels can be predicted using the PSORT programs (Nakai and Horton, Trends Biochem. Sci. (1999) 24:34–36; http://psort.nibb.ac.jp:8800/) and/or PFAM (Bateman et al., Nucleic Acids Res. (1999) 27:260–262).

In one embodiment, the TWIK channel protein fragments encoded by the TWIK channel nucleic acids, or derivative nucleic acids, preferably comprise at least 10 contiguous amino acids, more preferably at least 12 contiguous amino acids, still more preferably at least 15 contiguous amino acids, and most preferably at least 20 contiguous amino acids of any one of SEQ ID NOs:2, 4, 6, 8, 10, and 14. Alternatively, the encoded TWIK channel protein fragments comprise at least 20 contiguous amino acids, more preferably at least 25, and most preferably at least 30 contiguous amino acids that share 100% sequence similarity with a contiguous stretch of amino acids of the same length of any one of SEQ ID NOs:2, 4, 6, 8, 10 and 14. In another embodiment, the TWIK channel protein fragments encoded by the TWIK channel nucleic acids, or derivative nucleic acids, comprise at least 25 contiguous amino acids, preferably at least 30, more preferably at least 40 and most preferably at least 50 contiguous amino acids of any one of SEQ ID NOs:2, 4, 6, 8, 10, 12, and 14. Alternatively, the encoded TWIK channel protein fragments comprise at least 35 contiguous amino acids, more preferably at least 40, and most preferably at least 45 contiguous amino acids that share 100% sequence similarity with a contiguous stretch of amino acids of the same length of any one of SEQ ID NOs:2, 4, 6, 8, 10, 12, and 14. More specific embodiments of preferred TWIK channel protein fragments and derivatives are discussed further below in connection with specific TWIK channel proteins.

A derivative of the subject nucleic acid sequence, or fragment thereof, may comprise 100% sequence identity with the subject nucleic acid sequence, but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

Another type of derivative of the subject nucleic acid sequences includes corresponding humanized sequences. A humanized nucleic acid sequence is one in which one or more codons has been substituted with a codon that is more commonly used in human genes. Preferably, a sufficient number of codons have been substituted such that a higher level expression is achieved in mammalian cells than what would otherwise be achieved without the substitutions. The following list shows, for each amino acid, the calculated codon frequency (number in parentheses) in humans genes for 1000 codons (Wada et al., Nucleic Acids Research (1990) 18(Suppl.):2367–2411):

ARG: CGA (5.4), CGC (11.3), CGG (10.4), CGU (4.7), AGA (9.9), AGG (11.1)
LEU: CUA (6.2), CUC (19.9), CUG (42.5), CUU (10.7), UUA (5.3), UUG (11.0)
SER: UCA (9.3), UCC (17.7), UCG (4.2), UCU (13.2), AGC (18.7), AGU (9.4)
THR: ACA (14.4), ACC (23.0), ACG (6.7), ACU (12.7)
PRO: CCA (14.6), CCC (20.0), CCG (6.6), CCU (15.5)
ALA: GCA (14.0), GCC (29.1), GCG (7.2), GCU (19.6)
GLY: GGA (17.1), GGC (25.4), GGG (17.3), GGU (11.2)
VAL: GUA (5.9), GUC (16.3), GUG (30.9), GUU (10.4)
LYS: AAA (22.2), AAG (34.9)
ASN: AAC (22.6), AAU (16.6)
GLN: CAA (11.1), CAG (33.6)
HIS: CAC (14.2), CAU (9.3)
GLU: GAA (26.8), GAG (41.4)
ASP: GAC (29.0), GAU (21.7)
TYR: UAC (18.8), UAU (12.5)
CYS: UGC (14.5), UGU (9.9)
PHE: UUU (22.6), UUC (15.8)
ILE: AUA (5.8), AUC (24.3), AUU (14.9)
MET: AUG (22.3)
TRP: UGG (13.8)
TER: UAA (0.7), AUG (0.5), UGA (1.2)

Thus, a TWIK channel nucleic acid sequence in which the glutamic acid codon, GAA has been replaced with the codon GAG, which is more commonly used in human genes, is an example of a humanized TWIK channel nucleic acid sequence. A detailed discussion of the humanization of nucleic acid sequences is provided in U.S. Pat. No. 5,874,304 to Zolotukhin et al.

In various embodiments, the nucleic acids of the invention are less than 15 kb, 10 kb, 5 kb, or 2 kb, or less than 500 bases.

In a specific embodiment, the invention provides an isolated nucleic acid molecule of less than about 15 kb in size comprising a nucleic acid sequence selected from the group consisting of:

(a) a nucleic acid sequence that encodes a polypeptide comprising at least x contiguous amino acids of any one of SEQ ID NOs:2, 4, 6, 8, 10, 12, and 14, wherein for each respective SEQ ID NO, x is the number of amino acids listed in the column entitled "100% identity length x" in Table 4;

(b) a nucleic acid sequence that encodes a polypeptide comprising at least y amino acids that share 100% sequence identity or similarity with y amino acids of any one of SEQ ID NOs:2, 4, 6, 8, 10, 12, and 14, wherein for each respective SEQ ID NO, y is the number of amino acids listed in the column entitled "100% identity or similarity length y" in Table 4; and (c) the complement of the nucleic acid sequence of (a) or (b).

By way of example, such nucleic acid sequence can encode an amino acid sequence that comprises a sequence of 100% identity or similarity (e.g., as determined with no insertions or deletions, or via a computer algorithm known in the art) with at least 60 contiguous amino acids of residues 158 to 303 of SEQ ID NO:12. In a specific embodiment, the nucleic acid sequence encodes an amino acid sequence that comprises at least 60 contiguous amino acids of residues 158 to 303 of SEQ ID NO:12.

In another specific embodiment, the invention provides an isolated nucleic acid molecule comprising at least 14 or 39 contiguous nucleotides of residues 472 to 909 of SEQ ID NO:11.

5.2. Isolation, Production, and Expression of TWIK Channel Nucleic Acids

Nucleic acid encoding the amino acid sequence of any one of SEQ ID NOs:2, 4, 6, 8, 10, 12, and 14, may be obtained from an appropriate cDNA library prepared from any eukaryotic species that encodes TWIK channel proteins such as vertebrates, preferably mammalian (e.g. primate, porcine, bovine, feline, equine, and canine species, etc.) and invertebrates, such as arthropods, particularly insects species (preferably Drosophila and Leptotarsa), acarids, crustacea, molluscs, coelomates and pseudocoelomates. An expression library can be constructed using known methods. For example, mRNA can be isolated to make cDNA which is ligated into a suitable expression vector for expression in a host cell into which it is introduced. Various screening assays can then be used to select for the gene or gene product (e.g. oligonucleotides of at least about 20 to 80 bases designed to identify the gene of interest, or labeled antibodies that specifically bind to the gene product). The gene and/or gene product can then be recovered from the host cell using known techniques.

Polymerase chain reaction (PCR) can also be used to isolate nucleic acids of the TWIK channel where oligonucleotide primers representing fragmentary sequences of interest amplify RNA or DNA sequences from a source such as a genomic or cDNA library (as described by Sambrook et al., supra). Additionally, degenerate primers for amplifying homologues from any species of interest may be used. Once a PCR product of appropriate size and sequence is obtained, it may be cloned and sequenced by standard techniques, and utilized as a probe to isolate a complete cDNA or genomic clone.

Fragmentary sequences of SEQ ID NOs 1, 3, 5, 7, 9, 11, and 13 may be synthesized by known methods. For example, oligonucleotides may be synthesized using an automated DNA synthesizer available from commercial suppliers (e.g. Biosearch, Novato, Calif.; Perkin-Elmer Applied Biosystems, Foster City, Calif.). Antisense RNA sequences can be produced intracellularly by transcription from an exogenous sequence, e.g. from vectors that contain antisense TWIK channel nucleic acid sequences. Newly generated sequences may be identified and isolated using standard methods.

An isolated TWIK channel nucleic acid sequence can be inserted into any appropriate cloning vector, for example bacteriophages such as lambda derivatives, or plasmids such as PBR322, pUC plasmid derivatives and the Bluescript vector (Stratagene, San Diego, Calif.). Recombinant molecules can be introduced into host cells via transformation, transfection, infection, electroporation, etc. The transformed cells can be cultured to generate large quantities of the TWIK channel nucleic acid. Suitable methods for isolating and producing the subject nucleic acid sequences are well-known in the art (Sambrook et al., supra; DNA Cloning: A Practical Approach, Vol. 1, 2, 3, 4, (1995) Glover, ed., MRL Press, Ltd., Oxford, U.K.).

The nucleotide sequence encoding a TWIK channel protein or fragment or derivative thereof, can be inserted into any appropriate expression vector for the transcription and translation of the inserted protein-coding sequence. Alternatively, the necessary transcriptional and translational signals can be supplied by the native TWIK channel gene and/or its flanking regions. A variety of host-vector systems may be utilized to express the protein-coding sequence such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, DNA, plasmid DNA, or cosmid DNA. Expression of a TWIK channel protein may be controlled by a suitable promoter/enhancer element. In addition, a host cell strain may be selected which modulates the expression of the inserted sequences, or modifies and processes the gene product in the specific fashion desired.

In a specific embodiment, a vector is used that comprises a promoter operably linked to a TWIK channel gene nucleic acid, one or more origins of replication, and, one or more selectable markers (e.g. thymidine kinase activity, resistance to antibiotics, etc.) so that expression of the gene product can be detected. Alternatively, recombinant expression vectors can be identified by assaying for the expression of the TWIK channel gene product based on the physical or functional properties of the TWIK channel protein in in vitro assay systems (e.g. immunoassays).

In a specific embodiments, the TWIK channel protein, fragment, or derivative may be expressed as a fusion, or chimeric protein product (i.e. it is joined via a peptide bond to a heterologous protein sequence of a different protein). Such a chimeric product can be made by ligating the appropriate nucleic acid sequences encoding the desired amino acid sequences to each other in the proper coding frame (using methods known in the art) and expressing the chimeric product. Alternatively, such a chimeric product may be made by protein synthetic techniques, e.g. by use of a peptide synthesizer.

Once a recombinant which expresses the TWIK channel gene sequence is identified, the gene product can be isolated using standard methods (e.g. ion exchange, affinity, and sizing column chromatography; centrifugation; differential solubility). The amino acid sequence of the protein can be deduced from the nucleotide sequence of the chimeric gene contained in the recombinant. As a result, the protein can be synthesized by standard chemical methods known in the art (Hunkapiller et al., Nature (1984) 310:105–111). Alternatively, native TWIK channel proteins can be purified from natural sources, by standard methods (e.g. immunoaffinity purification).

5.3. TWIK Channel Proteins

The invention provides TWIK channel proteins that comprise or consist of an amino acid sequence of any one of SEQ ID NOs: 2, 4, 6, 8, 10, 12, and 14 or fragments or derivatives thereof. Compositions comprising these proteins may consist essentially of the TWIK channel proteins. Alternatively, the TWIK channel proteins may be a component of a composition that comprises other components (e.g. a diluent such as saline, a pharmaceutically acceptable carrier or excipient, a culture medium, carriers used in pesticide formulations, etc.).

Typically, a derivative of a TWIK channel protein will share a certain degree of sequence identity or sequence similarity with any one of SEQ ID NOs 2, 4, 6, 8, 10, 12, and 14, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported. Preferably, derivative amino acid sequences of the present invention have at least 80%, preferably at least 85%, more preferably at least 90%, and most preferably at least 95% sequence identity with any contiguous stretch of at least 20 amino acids, preferably at least 25 amino acids, more preferably at least 30 amino acids, and in some cases, the entire length of any one of SEQ ID NOs 2, 4, 6, 8, 10, 12, and 14. In some embodiments, the contiguous stretch of amino acids encodes a P or TM domain of the TWIK channel polypeptide. "Percent (%) amino acid sequence similarity" is determined by doing the same calculation as for determining % amino acid sequence identity described above, but including conservative amino acid substitutions in additional to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine and valine; interchangeable polar amino acids are glutamine and asparagine; interchangeable basic amino acids arginine, lysine and histidine; interchangeable acidic amino acids aspartic acid and glutamic acid; and interchangeable small amino acids alanine, serine, threonine, methionine, and glycine.

A preferred derivative of TWIK2 consists of or comprises an amino acid sequence that has at least 55%, preferably at least 60%, and more preferably, at least 65% sequence identity with any of amino acid residues 634–657, or 811–833 of SEQ ID NO:2 (i.e. the P domains), or any of amino acid residues 556–572, 676–692, 804–820, or 856–872 of SEQ ID NO:2 (i.e. the TM domains). Other preferred amino acid derivatives of TWIK2 consist of or comprise an amino acid sequence that shares at least 75% similarity, preferably at least 80% similarity, and more preferably, at least 85% similarity with any of amino acid residues 634–657, 811–833, 556–572, 676–692, 804–820, or 856–872 of SEQ ID NO:2. In another embodiment, a preferred derivative of TWIK2 consists of or comprises an amino acid sequence that shares 100% sequence similarity with any of at least 15, preferably at least 16, more preferably at least 17, and most preferably at least 18 contiguous amino acids of SEQ ID NO:2.

A preferred derivative of TWIK3 consists of or comprises an amino acid sequence that has at least 55%, preferably at least 60%, and more preferably, at least 65% sequence identity with any of amino acid residues 135–159, or 646–669 of SEQ ID NO:4 (i.e. the P domains), or any of amino acid residues 34–50, 169–185, 634–650, or 692–708 of SEQ ID NO:4 (i.e. the TM domains). Other preferred amino derivatives of TWIK3 consist of or comprise an amino acid sequence that shares at least 75% similarity, preferably at least 80% similarity, and more preferably, at least 85% similarity with any of amino acid residues of 135–159, 646–669, 34–50, 169–185, 634–650, or 692–708 of SEQ ID NO:4. In another embodiment, a preferred derivative of TWIK3 consists of or comprises an amino acid sequence that shares 100% sequence similarity with any of at least 17, preferably at least 18, more preferably at least 19, and most preferably at least 20 contiguous amino acids of SEQ ID NO:4.

A preferred derivative of TWIK4 consists of or comprises an amino acid sequence that has at least 55%, preferably at least 60%, and more preferably, at least 65% sequence identity with any of amino acid residues 127–151, or 311–334 of SEQ ID NO:6 (i.e. the P domains), or any of amino acid residues 34–50, 159–175, 287–303, or 355–371 of SEQ ID NO:6 (i.e. the TM domains). Other preferred amino derivatives of TWIK4 consist of or comprise an amino acid sequence that shares at least 75% similarity, preferably at least 80% similarity, and more preferably, at least 85% similarity with any of amino acid residues 127–151, 311–334, 34–50, 159–175, 287–303, or 355–371 of SEQ ID NO:6. In another embodiment, a preferred derivative of TWIK4 consists of or comprises an amino acid sequence that shares 100% sequence similarity with any of at least 16, preferably at least 17, more preferably at least 18, and most preferably at least 19 contiguous amino acids of SEQ ID NO:6.

A preferred derivative of TWIK5 consists of or comprises an amino acid sequence that has at least 55%, preferably at least 60%, and more preferably, at least 65% sequence identity with any of amino acid residues 191–214, or 1076–1099 of SEQ ID NO:8 (i.e. the P domains), or any of amino acid residues 74–94, 221–241, 1049–1070, or 1113–1137 of SEQ ID NO:8 (i.e. the TM domains). Other preferred amino derivatives of TWIK5 consist of or comprise an amino acid sequence that shares at least 75% similarity, preferably at least 80% similarity, and more preferably, at least 85% similarity with any of amino acid residues 191–214,1076–1099, 74–94,221–241, 1049–1070, or 1113–1137 of SEQ ID NO:8. In another embodiment, a preferred derivative of TWIK5 consists of or comprises an amino acid sequence that shares 100% sequence similarity with any of at least 18, preferably at least 19, more preferably at least 20, and most preferably at least 21 contiguous amino acids of SEQ ID NO:8.

A preferred derivative of TWIK6 consists of or comprises an amino acid sequence that has at least 55%, preferably at least 60%, and more preferably, at least 65% sequence identity with amino acid residues 15–35 of SEQ ID NO:10 (i.e. a P domains), or any of amino acid residues 45–105 of SEQ ID NO:10 (i.e. a TM domain). Other preferred amino derivatives of TWIK6 consist of or comprise an amino acid sequence that shares at least 75% similarity, preferably at least 80% similarity, and more preferably, at least 85% similarity with any of amino acid residues 15–35 or 45–105 of SEQ ID NO:10. In another embodiment, a preferred derivative of TWIK6 consists of or comprises an amino acid sequence that shares 100% sequence similarity with any of at least 15, preferably at least 16, more preferably at least 17, and most preferably at least 18 contiguous amino acids of SEQ ID NO:10.

A preferred derivative of TWIK7 consists of or comprises an amino acid sequence that has at least 55%, preferably at least 60%, and more preferably, at least 65% sequence identity with any of amino acid residues 78–101, or 184–207 of SEQ ID NO:12 (i.e. the P domains), or any of amino acid residues 9–25, 109–125, 161–177, or 224–240 of SEQ ID NO:12 (i.e. the TM domains). Other preferred amino derivatives of TWIK7 consist of or comprise an amino acid sequence that shares at least 75% similarity, preferably at least 80% similarity, and more preferably, at least 85% similarity with any of amino acid residues 78–101, 184–207, 9–25, 109–125, 161–177, or 224–240 of SEQ ID NO:12. In another embodiment, a preferred derivative of TWIK7 consists of or comprises an amino acid sequence that shares 100% sequence similarity with any of at least 31, preferably at least 32, more preferably at least 33, and most preferably at least 34 contiguous amino acids of SEQ ID NO:12.

A preferred derivative of cpbTWIK1 consists of or comprises an amino acid sequence that has at least 55%, preferably at least 60%, and more preferably, at least 65% sequence identity with any of amino acid residues 125–149, or 235–259 of SEQ ID NO:14 (i.e. the P domains), or any of amino acid residues 46–60, 156–176, 204–231, or 274–296 of SEQ ID NO:14 (i.e. the TM domains). Other preferred amino derivatives of cpbTWIK1 consist of or comprise an amino acid sequence that shares at least 75% similarity, preferably at least 80% similarity, and more preferably, at least 85% similarity with any of amino acid residues 125–149, 235–259, 46–60, 156–176, 204–231, or 274–296 of SEQ ID NO:14. In another embodiment, a preferred derivative of cpbTWIK1 consists of or comprises an amino acid sequence that shares 100% sequence similarity with any of at least 20, preferably at least 21, more preferably at least 22, and most preferably at least 23 contiguous amino acids of SEQ ID NO:14.

The invention also provides proteins having amino acid sequences that consist of or comprise a fragment of any one of SEQ ID NOs 2, 4, 6, 8, 10, 12, and 14. The fragments usually have at least 24, preferably at least 26, more preferably at least 30, and most preferably at least 45 contiguous amino acids of any one of SEQ ID NOs 2, 4, 6, 8, 10, 12, and 14. In certain embodiments, the following fragments are preferred: at least 8, preferably at least 9, more preferably at least 10, and most preferably at least 11 contiguous amino acids of any of SEQ ID NO:2, SEQ ID NO:6, SEQ ID NO:8, and SEQ ID NO:14; at least 7, preferably at least 8, more preferably at least 9, and most preferably at least 10 contiguous amino acids of SEQ ID NO:10; at least 9, preferably at least 10, more preferably at least 11, and most preferably at least 12 contiguous amino acids of SEQ ID NO:4; and at least 23, preferably at least 24, more preferably at least 25, and most preferably at least 26 contiguous amino acids of SEQ ID NO:12. A preferred fragment of SEQ ID NO:12 comprises residues 158 to 303, which are 100% identical to SEQ ID NO:69. The invention also provides a protein comprising at least 60 contiguous amino acids of residues 158 to 303 of SEQ ID NO:12, or comprising an amino acid sequence of 100% similarity or identity (e.g., as determined with no insertions or deletions, or via a computer algorithm known in the art) with at least 60 contiguous amino acids of residues 158 to 303 of SEQ ID NO:12.

Preferably the fragment or derivative of the TWIK channel protein is "functionally active" meaning that the TWIK channel protein derivative or fragment exhibits one or more functional activities associated with a full-length, wild-type TWIK channel protein comprising the amino acid sequence of any one of SEQ ID NOs:2, 4, 6, 8, 10, 12, and 14. As one example, a fragment or derivative may have antigenicity such that it can be used in immunoassays, for immunization, for inhibition of TWIK channel activity, etc, as discussed further below regarding generation of antibodies to TWIK channel proteins. For purposes herein, functionally active fragments also include those fragments that exhibit one or more structural features of a TWIK channel, such as a P or TM domain. Fragments or derivatives of TWIK channel proteins can be tested for functional activity by various procedures known in the art.

The TWIK channel derivatives of the invention can be produced by various methods known in the art. The manipulations which result in their production can occur at the gene or protein level. For example, a cloned TWIK channel gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, a TWIK channel gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, NaBH4, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the TWIK channel protein sequence.

Chimeric or fusion proteins can be made comprising an TWIK channel protein or fragment thereof (preferably consisting of at least a domain or motif of the TWIK channel protein) joined at its amino- or carboxy-terminus via a peptide bond to an amino acid sequence of a different protein. Such a chimeric protein can be produced by any known method, including: recombinant expression of a nucleic acid encoding the protein (comprising a TWIK channel-coding sequence joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

5.4. Antibodies to TWIK Channel Proteins

TWIK channel proteins, including functional derivatives and fragments thereof (e.g. a TWIK channel protein encoded by a sequence of any one of SEQ ID NOs:2, 4, 6, 8, 10, 12, and 14, or a subsequence thereof) may be used as an immunogen to generate monoclonal or polyclonal antibodies and antibody fragments or derivatives (e.g. chimeric, single chain, Fab fragments). For example, antibodies to a particular domain of an TWIK channel protein may be desired (e.g. a P or TM domain). In a specific embodiment, fragments of a TWIK channel protein identified as hydrophilic are used as immunogens for antibody production using art-known methods. Various known methods for antibody production can be used including cell culture of hybridomas; production of monoclonal antibodies in germ-free animals (PCT/US90/02545); the use of human hybridomas (Cole et al., PNAS (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101). In a particular embodiment, TWIK polypeptide fragments provide specific antigens and/or immunogens, especially when coupled to carrier proteins. For example, peptides are covalently coupled to keyhole limpet antigen (KLH) and the conjugate is emulsified in Freund's complete adjuvant. Laboratory rabbits are immunized according to conventional protocol and bled. The presence of specific antibodies is assayed by solid phase immunosorbent assays using immobilized corresponding polypeptide. Specific activity or function of the antibodies produced may be determined by convenient in vitro, cell-based, or in vivo assays: e.g. in vitro binding assays, etc. Binding specificity may be assayed by binding equilibrium constants (usually at least about $10^7$ $M^{-1}$, preferably at least about $10^8$ $M^{-1}$, more preferably at least about $10^9$ $M^{-1}$).

5.5. Identification of Proteins That Interact with TWIK Channels

The present invention provides methods of identifying or screening for molecules, such as proteins or other compounds, which interact with TWIK channel proteins, or derivatives, or fragments thereof. Assays to find interacting proteins can be performed by any method known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, etc. A preferred method for identifying interacting proteins is a two hybrid assay system or variation thereof (Fields and Song, Nature (1989) 340:245–246; U.S. Pat. No. 5,283,173; for review see Brent and Finley, Annu. Rev. Genet. (1997) 31:663–704).

The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with TWIK channel proteins, the "bait" is preferably a TWIK channel protein, expressed as a fusion protein to a DNA binding domain; and the "prey" protein is a protein to be tested for ability to interact with the bait, and is expressed as a fusion protein to a transcription activation domain. In one embodiment, the prey proteins can be obtained from recombinant biological libraries expressing random peptides.

The bait fusion protein can be constructed using any suitable DNA binding domain, such as the *E. coli* LexA repressor protein, or the yeast GAL-4 protein (Bartel et al., BioTechniques (1993) 14:920–924, Chasman et al., Mol. Cell. Biol. (1989) 9:4746–4749; Ma et al., Cell (1987) 48:847–853; Ptashne et al., Nature (1990) 346:329–331).

The prey fusion protein can be constructed using any suitable activation domain such as GAL-4, VP-16, etc. In various embodiments the preys contain useful moieties such as nuclear localization signals (Ylikomi et al., EMBO J. (1992) 11:3681–3694; Dingwall and Laskey, Trends Biochem. Sci. Trends Biochem. Sci. (1991) 16:479–481) or epitope tags (Allen et al., Trends Biochem. Sci. Trends Biochem. Sci. (1995) 20:511–516) to facilitate isolation of the encoded proteins.

Any reporter gene can be used that has a detectable phenotype. In various specific embodiments, some reporter genes allow cells expressing them to be selected by growth on appropriate medium (e.g HIS3, LEU2 described by Chien et al., PNAS (1991) 88:9572–9582; and Gyuris et al., Cell (1993) 75:791–803). Others allow cells expressing them to be visually screened such as LacZ and GFP (Chien et al., supra; and http:/www.bio101.com), etc.

Although the preferred host for two-hybrid screening is the yeast, the host cell in which the interaction assay and transcription of the reporter gene occurs can be any cell, such as mammalian (e.g. monkey, mouse, rat, human, bovine), chicken, bacterial, or insect cells. Various vectors and host strains for expression of the two fusion protein populations in yeast can be used (U.S. Pat. No. 5,468,614; Bartel et al., Cellular Interactions in Development (1993) Hartley, ed., Practical Approach Series xviii, IRL Press at Oxford University Press, New York, N.Y., pp. 153–179; and Fields and Sternglanz, Trends In Genetics (1994) 10:286–292). As an example of a mammalian system, interaction of activation tagged VP16 derivatives with a GAL-4-derived bait drives expression of reporters that direct the synthesis of Hygromycin B phosphotransferase, Chloramphenicol acetyltransferase, or CD4 cell surface antigen (Fearon et al., PNAS (1992) 89:7958–7962). In another embodiment, interaction of VP16-tagged derivatives with GAL-4-derived baits drives the synthesis of SV40 T antigen, which in turn promotes the replication of the prey plasmid, which carries an SV40 origin (Vasavada et al., PNAS (1991) 88:10686–10690).

In a preferred embodiment, the bait TWIK channel gene and the prey library of chimeric genes are combined by mating the two yeast strains on solid or liquid media for a period of approximately 6–8 hours. The resulting diploids contain both kinds of chimeric genes, i.e., the DNA-binding domain fusion and the activation domain fusion.

Transcription of the reporter gene can be detected by a linked replication assay, for example, as described by Vasavada et al., supra, or using immunoassay methods, preferably as described in Alam and Cook (Anal. Biochem. (1990)188:245–254). The activation of other reporter genes like URA3, HIS3, LYS2, or LEU2 enables the cells to grow in the absence of uracil, histidine, lysine, or leucine, respectively, and hence serves as a selectable marker. Other types of reporters are monitored by measuring a detectable signal. For example, GFP and lacZ have gene products that are fluorescent and chromogenic, respectively.

After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotide primers specific for the coding region of the DNA binding domain or activation domain. Other known amplification methods can be used, such as ligase chain reaction, use of Q replicase, or various other methods described (see Kricka et al., Molecular Probing, Blotting, and Sequencing (1995) Academic Press, New York, Chapter 1 and Table IX).

If a shuttle (yeast to *E. coli*) vector is used to express the fusion proteins, the DNA sequences encoding the proteins can be isolated by transforming the yeast DNA into *E. coli* and recovering the plasmids from *E. coli*. Alternatively, the yeast vector can be isolated, and the insert encoding the fusion protein subcloned into a bacterial expression vector, for growth of the plasmid in E. coli.

It should be noted that one of the inefficiencies in the two-hybrid system is use of transmembrane portions of proteins in the bait or the prey fusions (Ausubel et al., supra; Allen et al., supra). Since most of the two-hybrid systems are engineered to enter the nucleus and activate transcription, use of transmembrane portions of proteins will interfere with proper association, folding, and nuclear transport of bait or prey segments for transcriptional activation. Since all proteins in the present invention are transmembrane proteins, a successful two-hybrid scheme for TWIK channel proteins will use non-membrane associated domains for bait.

5.6. Biochemical and Functional Assays Using TWIK Channel Proteins

TWIK channel proteins are useful for biochemical assays aimed at the identification and characterization of molecules that modulate the action of TWIK channel proteins and modify their properties as ion channels. The cDNAs encoding the TWIK channel proteins can be individually subcloned into any of a large variety of eukaryotic expression vectors permitting expression in insect and mammalian cells, described above. The resulting genetically engineered cell lines expressing TWIK channel proteins can be assayed for production, processing, and secretion of mature TWIK channel proteins, for example with antibodies to Drosophila, or Leptotarsa TWIK channel proteins and Western blotting assays, ELISA assays, or electrophysiology studies.

The TWIK channel proteins, their derivatives, fragments, or domains, can be used in assays to identify molecules that would specifically bind to them. For assays specific to ion channels and their functional activation, one can employ either crude culture medium or extracts containing secreted protein from genetically engineered cells (devoid of other TWIK channel proteins), or partially purified culture medium or extracts, or preferably highly purified Drosophila TWIK channel protein fractionated, for example, by chromatographic methods. Alternatively, a mature TWIK channel protein can be synthesized using chemical methods (Nagata et al., Peptides (1992) 13(4):653–662).

5.7. Identification of TWIK Binding Proteins

The functional activity of TWIK proteins, derivatives and fragments can be assayed by various methods known to one skilled in the art (Current Protocols in Protein Science (1998) Coligan et al., eds., John Wiley & Sons, Inc., Somerset, N.J.). For example, various immunoassays are available for testing the ability of a protein to bind to or compete with a wild-type TWIK protein for binding to an anti-TWIK protein antibody. Suitable assays include radioimmunoassays, ELISA (enzyme linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g. gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Other assays would include binding assays between a TWIK, its binding protein, its substrates, or receptors, where such molecules are identified.

Finally, function of a TWIK gene can be assayed by mis-expressing a wild-type or mutant TWIK gene that encodes the TWIK gene protein in a transgenic animal by driving expression with a homologous or heterologous promoter; and detecting a phenotype in the transgenic animal, so as to study the function of the TWIK gene.

5.8. TWIK Gene Regulatory Elements

TWIK gene regulatory DNA elements such as enhancers or promoters, can be assayed to identify tissues, cells, genes and factors that specifically control TWIK protein production. Analyzing components that are specific to TWIK protein function can lead to an understanding of how to manipulate these regulatory processes, especially for pesticide and therapeutic applications, as well as an understanding of how to diagnose dysfunction in these processes.

In a specific embodiment, gene fusions with the TWIK regulatory elements can be made. For compact genes that have relatively few and small intervening sequences, such as those described herein for Drosophila, or Leptinotarsa, it is typically the case that the regulatory elements that control spatial and temporal expression patterns are found in the DNA immediately upstream of the coding region, extending to the nearest neighboring gene. Regulatory regions can be used to construct gene fusions where the regulatory DNAs are operably fused to a coding region for a reporter protein whose expression is easily detected, and these constructs are introduced as transgenes into the animal of choice. An entire regulatory DNA region can be used, or the regulatory region can be divided into smaller segments to identify subelements that might be specific for controlling expression a given cell type or stage of development. Examples of reporter proteins that can be used for construction of these gene fusions include E. coli beta-galactosidase or green fluorescent protein (GFP) whose products can be detected readily in situ and that are useful for histological studies (O'Kane and Gehring PNAS (1987) 84(24):9123–9127; Chalfie et al., Science (1994) 263:802–805) and sorting of specific cells that express TWIK proteins (Cumberledge and Krasnow (1994) Methods in Cell Biology 44:143–159); the cre or FLP recombinase proteins that can be used to control the presence and expression of other genes in the same cells through site-specific recombination (Golic and Lindquist (1989) Cell 59(3):499–509; White et al., Science (1996) 271:805–807); toxic proteins such as the reaper and hid cell death proteins, which are useful to specifically ablate cells that normally express TWIK proteins in order to assess the physiological function of the cells (Kingston, In Current Protocols in Molecular Biology (1998) Ausubel et al., John Wiley & Sons, Inc. sections 12.0.3–12. 10) or any other protein where it is desired to examine the function this particular protein specifically in cells that synthesize TWIK proteins.

Alternatively, a binary reporter system can be used, similar to that described above, where the TWIK regulatory element is operably fused to the coding region of an exogenous transcriptional activator protein, such as the GAL4 or tTA activators described above, to create an TWIK regulatory element "driver gene". For the other half of the binary system the exogenous activator controls a separate "target gene" containing a coding region of a reporter protein operably fused to a cognate regulatory element for the exogenous activator protein, such as UASG or a tTA-response element, respectively. An advantage of a binary system is that a single driver gene construct can be used to activate transcription from preconstructed target genes encoding different reporter proteins, each with its own uses as delineated above.

The TWIK regulatory element-reporter gene fusions described in the preceding paragraph are also useful for tests of genetic interactions, where the objective is to identify those genes that have a specific role in controlling the expression of TWIK genes, or promoting the growth and differentiation of the tissues that expresses the TWIK protein.

In another specific embodiment, TWIK gene regulatory DNA elements are useful in protein-DNA binding assays to identify gene regulatory proteins that control the expression of TWIK genes. Such gene regulatory proteins can be detected using a variety of methods that probe specific protein-DNA interactions well known to those skilled in the art (Kingston, supra) including in vivo footprinting assays based on protection of DNA sequences from chemical and enzymatic modification within living or permeabilized cells, in vitro footprinting assays based on protection of DNA sequences from chemical or enzymatic modification using protein extracts nitrocellulose filter-binding assays and gel electrophoresis mobility shift assays using radioactively labeled regulatory DNA elements mixed with protein extracts. Candidate TWIK gene regulatory proteins can themselves be purified using a combination of conventional and DNA-affinity purification techniques. Molecular cloning strategies can also be used to identify proteins that specifically bind TWIK gene regulatory DNA elements. For example, a Drosophila cDNA library in an expression vector, can be screened for Drosophila cDNAs that encode TWIK gene regulatory element DNA-binding activity. Similarly, the yeast "one-hybrid" system can be used (Li and Herskowitz, Science (1993) 262:1870–1874; Luo et al., Biotechniques (1996) 20(4):564–568; Vidal et al., PNAS (1996) 93(19):10315–10320).

5.9. Generation and Genetic Analysis of Animals and Cell Lines with Altered Expression of TWIK Genes Both genetically modified animal models (i.e. in vivo models), such as *C. elegans* and Drosophila, and in vitro models such as genetically engineered cell lines expressing or mis-expressing TWIK pathway genes, are useful for the functional analysis of these channels. Such models that display detectable phenotypes, such as those described in more detail below, can be used for the identification and characterization of TWIK pathway genes or other genes of interest and/or phenotypes associated with the mutation or mis-expression of an TWIK pathway protein. The term "mis-expression" as used herein encompasses mis-expression due to gene mutations. Thus, a mis-expressed TWIK pathway protein may be one having an amino acid sequence that differs from wild-type (i.e. it is a derivative of the normal protein). A mis-expressed TWIK pathway protein may also be one in which one or more amino acids have been deleted, and thus is a "fragment" of the normal protein. As used herein, "mis-expression" also includes ectopic expression (e.g. by altering the normal spatial or temporal expression), over-expression (e.g. by multiple gene copies), underexpression, non-expression (e.g. by gene knockout or blocking expression that would otherwise normally occur), and further, expression in ectopic tissues. As used in the following discussion concerning in vivo and in vitro models, the term "gene of interest" refers to an TWIK pathway gene (i.e. TWIK, TAP), or any other gene involved in regulation or modulation of the TWIK pathway.

The in vivo and in vitro models may be genetically engineered or modified so that they 1) have deletions and/or insertions of one or more TWIK pathway genes, 2) harbor interfering RNA sequences derived from TWIK pathway genes, 3) have had one or more endogenous TWIK pathway genes mutated (e.g. contain deletions, insertions, rearrangements, or point mutations in an TWIK gene or genes), and/or 4) contain transgenes for mis-expression of wild-type or mutant forms of such genes. Such genetically modified in vivo and in vitro models are useful for identification of new genes that are involved in the synthesis, activation, control, etc. of TWIK pathway genes and/or gene products. The newly identified genes could constitute possible pesticide targets (as judged by animal model phenotypes such as non-viability, block of normal development, defective feeding, defective movement, or defective reproduction). The model systems can also be used for testing potential pesticidal or pharmaceutical compounds that interact with the TWIK pathway, for example by administering the compound to the model system using any suitable method (e.g. direct contact, ingestion, injection, etc.) and observing any changes in phenotype, for example defective movement, lethality, etc.

Various genetic engineering and expression modification methods which can be used are known to one of ordinary skill in the art, including chemical mutagenesis, transposon mutagenesis, antisense RNA interference, and transgene-mediated mis-expression.

5.10. Generating Loss-of-Function Mutations by Mutagenesis

Loss-of-function mutations in an invertebrate metazoan TWIK gene can be generated by one of many mutagenesis methods known to investigators skilled in the art (Ashbumer, In *Drosophila melanogaster*: A Laboratory Manual (1989), Cold Spring Harbor, N.Y., Cold Spring Harbor Laboratory Press: pp. 299–418; Fly pushing: The Theory and Practice of *Drosophila melanogaster* Genetics (1997) Cold Spring Harbor Press, Plainview, N.Y.; The nematode *C. elegans* (1988) Wood, Ed., Cold Spring Harbor Laboratory Press, Cold Spring harbor, N.Y.). Techniques for producing mutations in a gene or genome could include use of radiation (e.g., X-ray, UV, or gamma ray), or chemicals (e.g., EMS, MMS, ENU, formaldehyde, etc.). Other methods of altering expression of genes include use of transposons (e.g., P element, EP-type "overexpression trap" element, mariner element, piggyBac transposon, hermes, minos, sleeping beauty, etc.), antisense, double-stranded RNA interference, peptide and RNA aptamers, directed deletions, homologous recombination, dominant negative alleles, and intrabodies.

5.11. Generating Loss-of-Function Phenotypes Using RNA-Based Methods

TWIK genes may be identified and/or characterized by generating loss-of-function phenotypes in animals of interest through RNA-based methods. Loss-of-function phenotypes can be generated by antisense RNA methods (Schubiger and Edgar, Methods in Cell Biology (1994) 44:697–713). One form of the antisense RNA method involves the injection of embryos with an antisense RNA that is partially homologous to the gene-of-interest (in this case a TWIK gene). Another form of the antisense RNA method involves expression of an antisense RNA partially homologous to the gene-of-interest by operably joining a portion of the gene-of-interest in the antisense orientation to a powerful promoter that can drive the expression of large quantities of antisense RNA, either generally throughout the animal or in specific tissues. Antisense RNA-generated loss-of-function phenotypes have been reported previously for several Drosophila genes including cactus, pecanex, and Krüppel (LaBonne et al., Dev. Biol. (1989) 136(1):1–16; Schuh and Jackle, Genome (1989) 31(1):422–425; Geisler et al., Cell (1992) 71(4):613–621).

Loss-of-function phenotypes can also be generated by cosuppression methods (Bingham Cell (1997) 90(3):385–387; Smyth, Curr. Biol. (1997) 7(12):793–795; Que an Jorgensen, Dev. Genet. (1998) 22(1):100–109). Cosuppression is a phenomenon of reduced gene expression produced by expression or injection of a sense strand RNA corresponding to a partial segment of the gene-of-interest. Cosuppression effects have been employed extensively in plants to generate loss-of-function phenotypes, but there is only a single report of cosuppression in Drosophila where reduced expression of the Adh gene was induced from a white-Adh transgene (Pal-Bhadra et al., Cell (1997) 90(3):479–490).

Another method for generating loss-of-function phenotypes is by double-stranded RNA interference (dsRNAi). This method is based on the interfering properties of double-stranded RNA derived from the coding regions of gene, and has proven to be of great utility in genetic studies of C. elegans (Fire et al., Nature (1998) 391:806–811), and can also be used to generate loss-of-function phenotypes in Drosophila (Kennerdell and Carthew, Cell (1998) 95:1017–1026; Misquitta and Patterson PNAS (1999) 96:1451–1456). In this method, complementary sense and antisense RNAs derived from a substantial portion of a gene of interest, such as a sensitizer or TWIK gene, are synthesized in vitro. The resulting sense and antisense RNAs are annealed in an injection buffer, and the double-stranded RNA injected or otherwise introduced into animals (such as in their food or by soaking in the buffer containing the RNA). Progeny of the injected animals are then inspected for phenotypes of interest.

5.12. Generating Loss-of-Function Phenotypes Using Peptide and RNA Aptamers

Another method for generating loss-of-function phenotypes is the use of peptide aptamers, which are peptides or small polypeptides that act as dominant inhibitors of protein function. Peptide aptamers specifically bind to target proteins, blocking their ability to function (Kolonin and Finley, PNAS (1998) 95:14266–14271). Due to the highly selective nature of peptide aptamers, they may be used not only to target a specific protein, but also to target specific functions of a given protein. Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. In one method, they are isolated from random peptide libraries by yeast two-hybrid screens (Xu et al., PNAS (1997) 94:12473–12478). They can also be isolated from phage libraries (Hoogenboom et al., Immunotechnology (1998) 4:1–20) or chemically generated peptides/libraries.

RNA aptamers are specific RNA ligands for proteins, that can specifically inhibit protein function of the gene (Good et al., Gene Therapy (1997) 4:45–54; Ellington. et al., Biotechnol. Annu. Rev. (1995) 1:185–214). In vitro selection methods can be used to identify RNA aptamers having a selected specificity (Bell et al., J. Biol. Chem. (1998) 273:14309–14314). RNA aptamers can be used to decrease the expression of an TWIK protein or derivative thereof, or a protein that interacts with the TWIK protein.

5.13. Generating Loss of Function Phenotypes Using Intrabodies

Intracellularly expressed antibodies, or intrabodies, are single-chain antibody molecules designed to bind and inactivate target molecules inside cells. Intrabodies have been used in cell assays and in whole organisms such as Drosophila (Chen et al., Hum. Gen. Ther. (1994) 5:595–601; Hassanzadeh et al., Febs Lett. (1998) 16(1, 2):75–80 and 81–86). In a preferred embodiment, inducible expression vectors are constructed with intrabodies that would react specifically with TWIK proteins.

5.14. Transgenesis

Typically, transgenic animals are created that contain gene fusions of the coding regions of the TWIK pathway gene (from either genomic DNA or cDNA) operably joined to a specific promoter and transcriptional enhancer whose regulation has been well characterized, preferably heterologous promoters/enhancers (i.e. promoters/enhancers that are non-native to the TWIK pathway genes being expressed). Heat shock promoters/enhancers, useful for temperature induced mis-expression in Drosophila include the hsp70 and hsp83 genes, and in C. elegans, include hsp 16-2 and hsp 16-41. Tissue specific promoters/enhancers are also useful, and in Drosophila, include sevenless (Bowtell et al., Genes Dev. (1988) 2(6):620–634), eyeless (Bowtell et al., PNAS (1991) 88(15):6853–6857), and glass-responsive promoters/enhancers (Quiring et al, Science (1994) 265:785–789) which are useful for expression in the eye; and enhancers/promoters derived from the dpp or vestigal genes which are useful for expression in the wing (Staehling-Hampton et al., Cell Growth Differ. (1994) 5(6):585–593; Kim et al., Nature (1996) 382:133–138). Finally, where it is necessary to restrict the activity of dominant active or dominant negative transgenes to regions where the pathway is normally active, it may be useful to use endogenous promoters of genes in the pathway, such as the TWIK pathway genes.

In C. elegans, examples of useful tissue specific promoters/enhancers include the myo-2 gene promoter, useful for pharyngeal muscle-specific expression; the hlh-1 gene promoter, useful for body-muscle-specific expression; and the mec-3 gene promoter, useful for touch-neuron-specific gene expression. In a preferred embodiment, gene fusions for directing the mis-expression of TWIK pathway genes are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of the TWIK pathway gene.

In Drosophila, binary control systems that employ exogenous DNA are useful when testing the mis-expression of genes in a wide variety of developmental stage-specific and tissue-specific patterns. Two examples of binary exogenous regulatory systems include the UAS/GAL4 system from yeast (Hay et al., PNAS (1997) 94(10):5195–5200; Ellis et al., Development (1993) 119(3):855–865), and the "Tet system" derived from *E. coli* (Bello et al., Development (1998) 125:2193–2202). The UAS/GAL4 system is a well-established and powerful method of mis-expression in Drosophila which employs the UASG upstream regulatory sequence for control of promoters by the yeast GAL4 transcriptional activator protein (Brand and Perrimon, Development (1993) 118(2):401–15). In this approach, transgenic Drosophila, termed "target" lines, are generated where the gene of interest to be mis-expressed is operably fused to an appropriate promoter controlled by UASG. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of pre-existing driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food. Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a gene of interest (e.g. a tumor suppressor gene) has lethal or deleterious effects when mis-expressed at an early stage in development, such as the embryonic or larval stages, the function of the gene of interest in the adult can still be assessed by adding tetracycline to the food during early stages of development and removing tetracycline later so as to induce mis-expression only at the adult stage.

Transposon insertions lying adjacent to the TWIK gene of interest may be use to generate deletions of flanking genomic DNA, which if induced in the germline, are stably propagated in subsequent generations. The utility of this technique in generating deletions has been demonstrated in male Drosophila using P elements in a technique known as P-mediated male recombination (Preston and Engels, Genetics (1996) 144:1611–1638).

Dominant negative mutations, where a mutation to a gene creates an inactive protein, can result in loss-of-function or reduced-function phenotype even in the presence of a normal copy of the gene, can be made using known methods (Hershkowitz, Nature (1987) 329:219–222). In the case of active monomeric proteins, over expression of an inactive form, achieved for example, by linking the mutant gene to a highly active promoter, can cause competition for natural substrates or ligands sufficient to significantly reduce net activity of the normal protein. Alternatively, changes to active site residues can be made to create a virtually irreversible association with a target.

In the case of active multimeric proteins, several strategies can guide selection of a dominant negative mutant. In one embodiment, activity of a multmeric complex can be decreased by expression of genes coding exogenous protein fragments that bind to the association domains of the wild type proteins and prevent multimer formation. Alternatively, over-expression of an inactive protein unit can sequester wild-type active units in inactive multimers, and thereby decrease multimeric activity (Nocka et al., EMBO J. (1990) 9:1805–1813). For example, in the case of multimeric DNA binding proteins, the DNA binding domain can be deleted, or the activation domain deleted. Also, in this case, the DNA binding domain unit can be expressed without the activation domain causing sequestering of the target DNA. Thereby, DNA binding sites are tied up without any possible activation of expression. In the case where a particular type of unit normally undergoes a conformational change during activity, expression of a rigid unit can also inactivate resultant complexes. It is also possible to replace an activation domain with a transcriptional repression domain and thus change a transcriptional activator into a transcriptional repressor. Transcriptional repression domains from the engrailed and Krüppel proteins have been used for such a purpose (Jaynes and O'Ferrell, EMBO J. (1991) 10:1427–1433; Licht et al., PNAS (1993) 90:11361–11365).

5.15. Assays for Change in Gene Expression

Various expression analysis techniques may be used to identify genes which are differentially expressed between a cell line or an animal expressing a wild type TWIK gene compared to another cell line or animal expressing a mutant TWIK gene. Such expression profiling techniques include differential display, serial analysis of gene expression (SAGE), nucleic acid array technology, subtractive hybridization, and proteome analysis (e.g. mass-spectrometry and two-dimensional protein gels). Nucleic acid array technology may be used to determine a global (i.e., genome-wide) gene expression pattern in a normal animal for comparison with an animal having a mutation in one or more TWIK gene. Gene expression profiling can also be used to identify other genes (or proteins) that may have a functional relation to (e.g. may participate in a signaling pathway with) or be a transcriptional target of an TWIK gene. The genes are identified by detecting changes in their expression levels following mutation, i.e., insertion, deletion or substitution in, or over-expression, under-expression, mis-expression or knock-out, of a TWIK gene.

5.16. Predicted Phenotypes Associated with TWIK Pathway Gene Mutations

After isolation of model animals carrying mutated or mis-expressed TWIK pathway genes or inhibitory RNAs, animals are carefully examined for phenotypes of interest. For analysis of TWIK pathway genes that have been mutated (i.e. deletions, insertions, and/or point mutations) animal models that are both homozygous and heterozygous for the altered TWIK pathway gene are analyzed. Examples of specific phenotypes that may be investigated include lethality; sterility; feeding behavior, perturbations in neuromuscular function including alterations in motility, and alterations in sensitivity to pesticides and pharmaceuticals. Some phenotypes more specific to flies include alterations in: larval crawling, flight ability, walking, grooming and phototaxis, alterations in the responses of sensory organs, changes in the morphology, size or number of imaginal discs, eyes, wings, legs, bristles, antennae, gut, fat body, and musculature. Some phenotypes more specific to nematodes include: locomotory, egg laying, chemosensation, male mating, and intestinal expulsion defects.

Genomic sequences containing an TWIK pathway gene can be used to confirm whether an existing mutant insect or worm line corresponds to a mutation in one or more TWIK pathway genes, by rescuing the mutant phenotype. Briefly, a genomic fragment containing the TWIK pathway gene of interest and potential flanking regulatory regions can be subcloned into any appropriate insect (such as Drosophila) or worm (such as C. elegans) transformation vector, and injected into the animals. For Drosophila, an appropriate helper plasmid is used in the injections to supply transposase. Resulting transformants are crossed for complementation testing to an existing panel of Drosophila or C. elegans lines whose mutations have been mapped to the vicinity of the gene of interest (Fly Pushing: The Theory and Practice of Drosophila Genetics, supra; and Caenorhabditis elegans: Modem Biological Analysis of an Organism (1995), Epstein and Shakes, eds.). If a mutant line is discovered to be rescued by this genomic fragment, as judged by complementation of the mutant phenotype, then the mutant line likely harbors a mutation in the TWIK pathway gene. This prediction can be further confirmed by sequencing the TWIK pathway gene from the mutant line to identify the lesion in the TWIK pathway gene.

5.17. Identification of Genes that Modify TWIK Genes

The characterization of new phenotypes created by mutations in TWIK genes enables one to test for genetic interactions between TWIK genes and other genes that may participate in the same, related, or interacting genetic or biochemical pathway(s). Individual genes can be used as starting points in large-scale genetic modifier screens as described in more detail below. Alternatively, RNAi methods can be used to simulate loss-of-function mutations in the genes being analyzed. It is of particular interest to investigate whether there are any interactions of TWIK genes with other well-characterized genes, particularly genes involved in ion transport.

5.18. Genetic Modifier Screens

A genetic modifier screen using invertebrate model organisms is a particularly preferred method for identifying genes that interact with TWIK genes, because large numbers of animals can be systematically screened making it more that interacting genes will be identified. In C. elegans and Drosophila, a screen of up to about 10,000 animals is considered to be a pilot-scale screen. Moderate-scale screens usually employ about 10,000 to about 50,000 flies or up to about 100,000 worms, and large-scale screens employ greater than about 50,000 or 100,000 flies or worms, respectively. In a genetic modifier screen, animals having a mutant phenotype due to a mutation in one or more TWIK genes are further mutagenized, for example by chemical mutagenesis or transposon mutagenesis. The mutagenesis procedures used in typical genetic modifier screens of C. elegans are well known in the art. One method involves exposure of hermaphrodites that carry mutations in one or more TWIK genes to a mutagen, such as EMS or trimethylpsoralen with ultraviolet radiation (Huang and Sternberg, Methods in Cell Biology (1995) 48:97–122). Alternatively, transposable elements are used, often by the introduction of a mutator locus, such as mut-2 or mut-7, which promotes mobility of transposons (Anderson, Methods in Cell Biology (1995) 4:31–58).

In Drosophila, the mutagenesis methods and other procedures used in a genetic modifier screen depend upon the precise nature of the mutant allele being modified; these methods are discussed in more detail below under the Drosophila genetic modifier screen subheading.

Progeny of the mutagenized animals are generated and screened for the rare individuals that display suppressed or enhanced versions of the original mutant TWIK phenotype. Such animals are presumed to have mutations in other genes, called "modifier" genes, that participate in the same phenotype-generating pathway. The newly-identified modifier genes can be isolated away from the mutations in the TWIK genes by genetic crosses, so that the intrinsic phenotypes caused by the modifier mutations can be assessed in isolation.

Modifier genes can be mapped using a combination of genetic and molecular methods known in the art. Modifiers that come from a genetic screen in C. elegans are preferably mapped with visible genetic markers and/or with molecular markers such as STS markers (The nematode C. elegans, supra, Caenorhabditis elegans: Modern Biological Analysis of an Organism, supra). Modifier genes may be uncovered by identification of a genomic clone which rescues the mutant phenotype. Alternatively, modifier genes that are identified by a Tc1-based screen can be uncovered using transposon display technology (Korswagen et al., PNAS (1996) 93:14680–14685).

Standard techniques used for the mapping of modifiers that come from a genetic screen in Drosophila include meiotic mapping with visible or molecular genetic markers; complementation analysis with deficiencies, duplications, and lethal P-element insertions; and cytological analysis of chromosomal aberrations (Fly Pushing: Theory and Practice of Drosophila Genetics, supra; Drosophila: A Laboratory Handbook, supra). Genes corresponding to modifier mutations that fail to complement a lethal P-element may be cloned by plasmid rescue of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated with TWIK genes using methods described above. Also, the new modifier mutations can be tested for interactions with genes in other pathways that are not believed to be related to ion transport (e.g. Notch in Drosophila, and lin-15 in C. elegans). New modifier mutations that exhibit specific genetic interactions with other genes implicated in ion transport, but not interactions with genes in unrelated pathways, are of particular interest.

The modifier mutations may also be used to identify "complementation groups". Two modifier mutations are considered to fall within the same complementation group if animals carrying both mutations in trans exhibit essentially the same phenotype as animals that are homozygous for each mutation individually and, generally are lethal when in trans to each other (Fly Pushing: The Theory and Practice of Drosophila Genetics, supra). Generally, individual complementation groups defined in this way correspond to individual genes.

When TWIK modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of TWIK genes, human and rodent homologues of the modifier genes are of particular interest. For pesticide and other agricultural applications, homologues of modifier genes in insects and arachnids are of particular interest. Insects, arachnids, and other organisms of interest include, among others, Isopoda; Diplopoda; Chilopoda; Symphyla; Thysanura; Collembola; Orthoptera, such as Scistocerca spp; Blattoidea, such as *Blattella germanica*; Dermaptera; Isoptera; Anoplura; Mallophaga; Thysanoptera; Heteroptera; Homoptera, including *Bemisia tabaci*, and Myzus spp.; Lepidoptera including *Plodia interpunctella, Pectinophora gossypiella*, Plutella spp., Heliothis spp., and Spodoptera species; Coleoptera such as Leptinotarsa, Diabrotica spp., Anthonomus spp., and Tribolium spp.; Hymenoptera, including *Apis mellifera*; Diptera, including Anopheles spp.; Siphonaptera, including *Ctenocephalides felis*; Arachnida; and Acarinan, including *Amblyoma americanum*; and nematodes, including Meloidogyne spp., and *Heterodera glycinii*.

5.19. Genetic Modifier Screens in Drosophila

The procedures involved in typical Drosophila genetic modifier screens are well-known in the art (Wolfner and Goldberg, Methods in Cell Biology (1994) 44:33–80; and Karim et al., Genetics (1996) 143:315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Although the above-described Drosophila genetic modifier screens are quite powerful and sensitive, some genes that interact with TWIK channel genes may be missed in this approach, particularly if there is functional redundancy of those genes. This is because the vast majority of the mutations generated in the standard mutagenesis methods will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth et al., Development (1998) 125:1049–1057). This method is based on a modular mis-expression system utilizing components of the GAL-4/UAS system (described above) where a modified P element, termed an "enhanced P" (EP) element, is genetically engineered to contain a GAL-4-responsive UAS element and promoter. Any other transposons can also be used for this system. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL-4-regulated promoter, and increased expression or mis-expression of the randomly tagged gene can be induced by crossing in a GAL-4 driver gene.

Systematic gain-of-function genetic screens for modifiers of phenotypes induced by mutation or mis-expression of a TWIK gene can be performed by crossing several thousand Drosophila EP lines individually into a genetic background containing a mutant or mis-expressed TWIK gene, and further containing an appropriate GAL-4 driver transgene. It is also possible to remobilize the EP elements to obtain novel insertions. The progeny of these crosses are then analyzed for enhancement or suppression of the original mutant phenotype as described above. Those identified as having mutations that interact with the TWIK can be tested further to verify the reproducibility and specificity of this genetic interaction. EP insertions that demonstrate a specific genetic interaction with a mutant or mis-expressed TWIK gene, have a physically tagged a new gene which can be identified and sequenced using PCR or hybridization screening methods, allowing the isolation of the genomic DNA adjacent to the position of the EP element insertion.

5.20. Identification of Compounds with Binding Capacity

Proteins and other compounds that bind to, or otherwise directly interact with TWIK genes and proteins can be identified by screening methodologies that are well known in the art (see e.g., PCT International Publication No. WO 96/34099). The proteins and compounds include endogenous cellular components that interact with the identified genes and proteins in vivo and may provide new targets for pharmaceutical and therapeutic interventions. Other recombinant, synthetic, and otherwise exogenous compounds may have binding capacity and, therefore, may be candidates for pharmaceutical agents. For example, cell lysates or tissue homogenates may be screened for proteins or other compounds that bind to one of the normal or mutant TWIK genes and proteins.

Any of a variety of exogenous compounds, both naturally occurring and/or synthetic (e.g., libraries of small molecules or peptides, or phage display libraries), may be screened for binding capacity. In a typical binding experiment a TWIK protein or fragment is mixed with test compounds under conditions conducive to binding for sufficient time for any binding to occur, and assays are performed to test for bound complexes.

5.21. Identification of Potential Pesticide or Drug Targets

Once TWIK channel genes or TWIK channel interacting genes are identified, they can be assessed as potential pesticide or drug targets. As used herein, the term "pesticide" refers generally to chemical compounds that kill, paralyze, sterilize or otherwise disable pest species in the areas of agricultural crop protection, human and animal health. Exemplary pest species include parasites and disease vectors such as mosquitoes, fleas, ticks, parasitic nematodes, chiggers, mites, etc. Pest species also include those that are eradicated for aesthetic and hygienic purposes (e.g. ants, cockroaches, clothes moths, flour beetles, etc.), home and garden applications, and protection of structures (including wood boring pests such as termites, and marine surface fouling organisms). Pesticidal compounds can include traditional small organic molecule pesticides (typified by compound classes such as the organophosphates, pyrethroids, carbamates, organochlorines, benzoylureas, etc.) as well as proteinaceous toxins (such as the *Bacillus thuringiensis* Crytoxins (Gill et al., Annu Rev Entomol (1992) 37:615–636) and *Photorabdus luminescens* toxins (Bowden et al., Science (1998) 280:2129–2132). The pesticides or small molecules can be delivered by a variety of means such as direct application of the protein or nucleic acid encoding the protein, viral infection, and transgenic plants expressing the toxin in their tissues.

Pesticides, drugs, and small molecules can be applied onto whole insects, nematodes, and other small invertebrate metazoans, and the ability of the compounds to modulate (e.g. block or enhance) TWIK channel activity can be observed. Alternatively, the effect of various compounds on TWIK channels can be assayed using cells that have been engineered to express one or more TWIK channels and associated proteins.

Assays of Compounds on Worms:

In a typical worm assay, the compounds to be tested are diluted in DMSO or other organic solvent, mixed with a bacterial solution, preferably OP50 strain of bacteria (Brenner, Genetics (1974) 110:421–440), and supplied as food to the worms. The population of worms to be treated can be synchronized larvae (Sulston and Hodgkin, in The nematode *C. elegans* (1988), supra) or adults. Further, compounds can be added directly to the plate media (e.g. agar), or worm assays can be performed in liquid culture that contain the compound of interest (The nematode *C. elegans*, supra, *Caenorhabditis elegans*: Modem Biological Analysis of an Organism, supra).

Adult and larval worms are treated with different concentrations of compounds, typically ranging from 1 mg/ml–0.001 mg/ml. Behavioral aberrations, such as a decrease in motility and growth, and morphological aberrations, sterility, and death are examined in both acutely and chronically treated adult and larval worms. For the acute assay, larval and adult worms are examined immediately after application of the compound and re-examined periodically (every 30 minutes) for 5–6 hours. Chronic, or long-term assays, are also performed on worms and the behavior of the treated worms are examined every 8–12 hours for 4–5 days. In some circumstances, it is necessary to reapply the pesticide to the treated worms every 24 hours for maximal effect.

Assays of Compounds on Insects:

Potential insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection. Insecticides are typically very hydrophobic molecules and must commonly be dissolved in organic solvents, which are allowed to evaporate in the case of methanol or acetone or at low concentrations can be included to facilitate uptake (ethanol, dimethyl sulfoxide).

The first step in an insect assay is the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from puparium). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior, locomotion, and molting may be observed. For application on adults, behavior and neurological defects are observed, and effects on fertility are noted.

For a chronic exposure assay, adults are placed on vials containing the compounds for 48 hours, then transferred to a clean container and observed for fertility, neurological defects, and death.

Assay of Compounds on Cell Cultures:

Compounds that modulate (e.g. block or enhance) TWIK channel activity may also be assayed using cell culture. For example, the effect of exogenously added compounds cells expressing TWIK channels may be screened for their ability to modulate the activity of TWIK genes based upon measurements of intracellular potassium ion levels or regulation. Since TWIK channels are integral membrane proteins which serve as ion channels, the compounds may be screened for their ability to modulate TWIK-related potassium ion transport by measurements of ion channel fluxes and/or transmembrane voltage or current fluxes using patch clamp, voltage clamp and fluorescent dyes sensitive to intracellular calcium or transmembrane voltage. Ion channel function can also be assayed using transcriptional reporters, altered localization of protein, or by measurements of activation of second messengers such as cyclic AMP, cGMP tyrosine kinases, phosphates, increases in intracellular potassium ion levels, etc.

Recombinantly made proteins may also be reconstructed in artificial membrane systems to study ion channel conductance and, therefore, the cells employed in such assays may comprise an artificial membrane or cell. Assays for changes in ion regulation or metabolism can be performed on cultured cells expressing endogenous normal or mutant TWIKs. Such studies also can be performed on cells transfected with vectors capable of expressing one of the TWIKs, or functional domains of one of the TWIKs, in normal or mutant form. In addition, to enhance the signal measured in such assays, cells may be cotransfected with genes encoding ion channel proteins. For example, Xenopus oocytes or human embryonic kidney cells (HEK293) may be transfected with normal or mutant TWIK sequences. Changes in TWIK-related or TWIK-mediated ion channel activity can be measured by two-microelectrode voltage-clamp recordings in oocytes or by whole-cell patch-clamp recordings in HEK293 cells. Methods for performing the experiments described here are detailed by Rudi and Iverson (Rudi B., and Iverson, L. in: Methods in Enzymology. Vol.207: Ion Channels. 1997, Publisher: Academic Press, New York). These procedures may be used to screen a battery of compounds, particularly potential pesticides or drugs. The selectivity of a material for a TWIK channel may be determined by testing the effect of the compound using cells expressing TWIK channels and comparing the results with that obtained using cells not expressing TWIK channels (see U.S. Pat. Nos. 5,670,335 and 5,882,873). Compounds that selectively modulate the TWIK channels are identified as potential pesticide and drug candidates having TWIK channel specificity.

Identification of small molecules and compounds as potential pesticides or pharmaceutical compounds at a rapid pace requires high-throughput screening (HTS) methods (Bolger, Drug Discovery Today (1999) 4:251–253). Several of the assays mentioned herein can lend themselves to such screening methods. For example, cells or cell lines expressing wild type or mutant TWIK channel proteins or their fragments, and a reporter gene can be subjected to compounds of interest, and depending on the reporter genes, interactions can be measured using a variety of methods such as color detection, fluorescence detection, autoradiography, scintillation analysis, etc. Examples of suitable cell-based screening assays are described in U.S. Pat. No. 5,559,026 and U.S. Pat. No. 5,756,351, incorporated herein by reference.

6. EXAMPLES

The following examples show how the nucleic acid sequences of SEQ ID NOs 1, 3, 5, 7, 9, 11, and 13 were isolated. An example of how these sequences and derivatives and fragments thereof can be used in compound screening assays is also provided. These examples are provided merely as illustrative of various aspects of the invention and should not be construed to limit the invention in any way.

6.1. Example 1

Preparation of CDNA Libraries
Drosophila Library

A Drosophila expressed sequence tag (EST) cDNA library was prepared as follows. Tissue from mixed stage embryos (0–20 hour), imaginal disks and adult fly heads were collected and total RNA was prepared. Mitochondrial rRNA was removed from the total RNA by hybridization with biotinylated rRNA specific oligonucleotides and the resulting RNA was selected for polyadenylated mRNA. The resulting material was then used to construct a random primed library. First strand cDNA synthesis was primed using a six nucleotide random primer. The first strand cDNA was then tailed with terminal transferase to add approximately 15 dGTP molecules. The second strand was primed using a primer which contained a NotI site followed by a 13 nucleotide C-tail to hybridize to the G-tailed first strand cDNA. The double stranded cDNA was ligated with BstX1 adaptors and digested with NotI. The cDNA was then sized on an agarose gel and the cDNA greater than 700 bp was purified. The cDNA was then ligated with NotI, BstX1 digested pcDNA-sk+ vector (a derivative of pBluescript, Stratagene) and transformed into bacterial cells (XL1blue). The final complexity of the library was 6×10$^6$ independent clones.

The cDNA library was normalized using a modification of a previously described method (Bonaldo et al., Genome Research (1996) 6:791–806). A biotinylated driver was prepared from the cDNA by PCR amplification of the inserts and allowed to hybridize with single stranded plasmids of the same library. The resulting double-stranded forms were removed using strepavidin magnetic beads, the remaining single stranded plasmids were converted to double stranded molecules using Sequenase (Amersham, Arlington Hills, Ill.), and the plasmid DNA stored at −20° C. prior to transformation. Aliquots of the normalized plasmid library were transformed into bacteria (XL1blue or DH10B), plated at moderate density, and the colonies picked into a 384-well master plate containing bacterial growth media using a Qbot robot (Genetix, Christchurch, UK). The clones were allowed to grow for 24 hours at 37° C. then the master plates were frozen at −80° C. for storage. The total number of colonies picked for sequencing from the normalized library was 240,000. The master plates were used to inoculate media for growth and preparation of DNA for use as template in sequencing reactions. The reactions were primarily carried out with primer that initiated at the 5' end of the cDNA inserts. However, a minor percentage of the clones were also sequenced from the 3' end. Clones were selected for 3' end sequencing based on either further biological interest or the selection of clones that could extend assemblies of contiguous sequences ("contigs") as discussed below. Sequencing reactions were carried out on ABI377s and used either ABI FS, dirhodamine or BigDye chemistries (Applied Biosystems, Inc., Foster City, Calif.).

Analysis of sequences were done as follows: the traces generated by the automated sequencers were base-called using the program "Phred" (Gordon, Genome Res. (1998) 8:195–202), which also assigned quality values to each base. The resulting sequences were trimmed for quality in view of the assigned scores. Vector sequences were also removed. Each sequence was compared to all other fly EST sequences using the BLAST program and a filter to identify regions of near 100% identity. Sequences with potential overlap were then assembled into contigs using the program "Phrap" (Phil Green, University of Washington, Seattle, Wash.; The resulting assemblies were then compared to existing public databases and homology to known proteins was then used to direct translation of the consensus sequence. Where no BLAST homology was available, the statistically most likely translation based on codon and hexanucleotide preference was used. The Pfam (Bateman et al., Nucleic Acids Res. (1999) 27:260–262) and Prosite (Hofmann et al., Nucleic Acids Res. (1999) 27(1):215–219) collection protein domains were used to identify motifs in the resulting translations. The contigs were placed in a database (FlyTag™, Exelixis Pharmaceuticals, Inc., South San Francisco, Calif.)

Leptinotarsa Library

The Leptinotarsa cDNA library was prepared using the Lambda ZAP cDNA cloning kit (Stratagene, cat#200450) following manufacturer's protocols. The original cDNA used to construct the library was oligo-dt primed using mRNA from mixed stage larvae Colorado Potato Beetle.

All colony picking, sequencing, and the data analysis were performed as described above for the Drosophila library. The resulting contigs were placed in a database (ColTag™, Exelixis Pharmaceuticals, Inc.).

6.2. Example 2

Cloning and Analysis of TWIK Nucleic Acid Sequences

The cloning of each of the TWIK nucleic acid sequences is described below. Upon completion of cloning, the sequences were analyzed using the Pfam and Prosite programs. The features of each sequence are outlined in Table 2 below. In addition, each completed sequence was searched using BLAST against the GenBank database to find the most similar DNA and protein sequences. The results of this search are outlined in Table 3.

Unless otherwise noted, the PCR conditions used for cloning each TWIK nucleic acid sequence were as follows:

A denaturation step of 94° C., 5 min; followed by 35 cycles of: 94° C. 1 min, 55° C. 1 min 72° C. 1 min; then, a final extension at 72° C. 10 min. All PCR primers encompassed the highly conserved P domains of TWIK nucleic acid sequences to help distinguish them from other potassium channels.

All DNA sequencing reactions were performed using standard protocols for the BigDye sequencing reagents (Applied Biosystems, Inc.) and products were analyzed using ABI 377 DNA sequencers. Trace data obtained from the ABI 377 DNA sequencers was analyzed and assembled into contigs using the Phred-Phrap programs.

As described where applicable below, some of the Drosophila TWIK nucleic acid and protein sequences are disclosed in co-pending U.S. applications Ser. No. 09/270,767 ('767) and Ser. No. 09/270,849 ('849), which were both filed on Mar. 17, 1999. All nucleic acid sequences below are shown in 5' to 3' orientation.

6.2.1. TWIK2

TWIK2 was discovered as a sequenced, large-insert P1 clone from the Berkeley Drosophila P1 library (P1 D205= DS02368, AC004313, GenBank id no. ("GI") 3006211) and deposited by the Berkeley Drosophila Genome Project, BDGP. This sequence was not annotated. The cDNA sequence was predicted using Genscan sequence prediction program (Burge & Karlin, J. Mol. Biol. (1997) 268:78–94). The full-length cDNA clone was produced by Rapid Amplification of cDNA ends (RACE) (Frohman et al., PNAS (1988) 85:8998–9002).

A RACE-ready library was generated from Clontech (Palo Alto, Calif.) Drosophila embryo polyA+ RNA (Cat# 6947-1) using Clontech's Marathon cDNA amplification kit (Cat# K1802 1), and following manufacturer's protocols. The following PCR primers were used on the library to retrieve full-length clones:

TWIK2F2: TGGCTAAATGACGAGCACGAGCAC SEQ ID NO:15

TWIK2R5: CAGTCCTCCTCTCTCATGTTGTGG SEQ ID NO:16

TWIK2F6: ACAGGTGCATTGCCTATCTCATCT SEQ ID NO:17

TWIK2R4: CGCGTTACGGTAAATTCGATTG SEQ ID NO:18

PCR conditions were as follows: An initial denaturation step at 94° C. for 2.5 min, followed by 30 cycles of 95° C., 40 sec; 68° C., 5 min, and a final extension at 72° C. for 7 min. Products of PCR reactions were fractionated on a 1% agarose gel, and purified from the gel using Qiagen (Valencia, Calif.) gel extraction kit following manufacturer's directions. The purified products were subject to a further round of PCR reactions, using only primers TWIK2F2/TWIK2R4. Products of this reaction were fractionated on a gel. The largest product was gel-purified and subcloned using Invitrogen's (Carlsbad, Calif.) TA cloning kit, following manufacturer's protocols. The obtained clones were then sequenced, and the final data resulted in a 3 kb contiguous sequence ("contig").

The predicted protein sequence of TWIK2 was analyzed using BLAST against known protein databases. The longest contiguous stretch of amino acid identity between TWIK2 and prior art sequences was 7, shared with C. elegans clone F31D4.7 (GI 3876514); the longest stretch of contiguous amino acid sequence similarity was 14, shared with the same clone.

6.2.2. TWIK3

TWIK3 was discovered as two independent EST clones found in the Exelixis FlyTag™ cDNA database, as described above. PCR using conserved sequences in the ESTs was used to probe the Berkeley Drosophila P1 library (From BDGP, and available from Research Genetics (Huntsville, Ala.,) to obtain large insert P1 clones covering the region, and also to obtain cytological information. 5' and 3' RACE reactions were employed to obtain full-length cDNA clones.

The following primers were used to perform PCR on Drosophila genomic DNA:

TWIK3.F1: TTACGACGACGATGACTCTATG SEQ ID NO:19

TWIK3.R1: AATCTTTAGTTCAAGTGCAGGTTT SEQ ID NO:20

TWIK5.F1: CTCCACTGCTCCGATGTCCGAACT SEQ ID NO:21

TWIK5.R1: CAACCGAGCGGCAAATTAGCCAA SEQ ID NO:22

The PCR products were fractionated on a 1% agarose gel, gel-purified, and then quantified with the aid of Hoefer DynaQuant 200 fluorometer (Amersham, Piscataway, N.J.). A total of 50 ng of each product was then used as a probe for hybridization onto P1 library filters. Each probe was labeled with α-dCTP 32P using Amersham's "redi-prime kit" as suggested by manufacturer. Labeled probes were then cleaned according to specifications with Pharmacia "probe-quant" columns. Counts were determined using a scintillation counter with counts ranging from 9×10 5–1×10 6 cpm. Probes were boiled for 10 min. at 100° C. and quickly added to pre-warmed (65° C.) hybridization buffer (5×SSPE, 5×Denhardt's solution, 0.5% SDS, 0.1 mg/ml fish DNA) which was subsequently added to library filters and hybridized overnight at 65° C.

Washes were performed the next day:

2 changes of 0.1×SSC, 0.1% SDS at room temperature for at least 15 min. each.

2 changes of 0.1×SSC, 0.1% SDS at 65° C. for at least 30 min. each.

The membranes were then exposed to BioMax autoradiography X-ray film (Kodak, Rochester, N.Y.) with two intensifying screens at −80° C. for two days.

The P1 filter produced 4 positive clones. Comparison of these clones to the BDGP database revealed all to map to a contig, Aprt, mapped to cytological band 61F3 62B11. PCR was then used using the same conditions and primers as before to verify the clones. Clones were propagated as described by Sambrook et al., supra. Genomic P1 clones in this contig have been sequenced by the BDGP.

The full-length cDNAs for each were obtained by RACE. The starting materials, as well as the protocols, were the same as those mentioned in the previous section. The following primers were used for RACE reactions on the EST clones believed to cover the 5' and the 3' portion of the TWIK gene coding region, respectively:

TWIK 3: 5' EST:

5' RACE TWK5-R4: TTGCCGGATCCCTGTTC-TACTCGA SEQ ID NO:23

3' RACE TWK5-F4: TGCGTCGTCGGACAGTAGCCA-GAT SEQ ID NO:24

TWIK 3: 3' EST

5' RACE TWK3-R4: CAAATCCGATTGTTGT-CAGTGT SEQ ID NO:25

3' RACE TWK3-F4: GAACACACTTTGAAAGATG-GATA SEQ ID NO:26

PCR conditions were as follows: an initial denaturation step of 95° C. for 1 min, followed by 30 cycles of 95° C. for 30 sec, 60° C. for 30 sec, and 68° C. for 3 min. The products of the PCR reactions were separated on a 1% agarose gel, and purified from the as mentioned above. The major reaction products were subcloned into the vector pCRII using Invitrogen's TA cloning kit, following manufacturer's protocols. Subsequent clones were sequenced with the above TWIK-specific primers, M13 forward and M13 reverse vector primers, and the following primers:

TWK3-F1: TTACGACGACGATGACTCTATG SEQ ID NO:27

TWK3-R2: CTCACTACCAGAAAGACGCATA SEQ ID NO:28

TWK5-F1: CTCCACTGCTCCGATGTCCGAACT SEQ ID NO:29

TWK5-R2: ATGACCCAACGGTCTGGGAATGAC SEQ ID NO:30

The sequence information was used to produce an approximately 3 kb of a total contiguous cDNA clone, containing a 2.2 kb open reading frame (ORF). Two separate PCR reactions were then used to generate two overlapping fragments: an approximately 1.5 kb 5' SacII-SalI fragment and an approximately 1 kb 3' SalI-NotI site for assembly into a protein expression vector. The following primers were used in these reactions:

TWK3-FF1-Sac: GTACATCCGCGGGAGGAGGCCA-GAGGAGGGTGACCATG SEQ ID NO:31

TWK3-RR2-SalI: GCGGTGGAGCATCATAGTCGG-GAAGT SEQ ID NO:32

TWK3-RR1-NotI: ACTAGTACTAGCGGCCGC-CTAATCCTCATCCTGCTCGTCGTCATCA SEQ ID NO:33

TWK3-FF2-SalI: ATCTTCCAAAGCGTCCA-GAGAACTGC SEQ ID NO:34

The reaction products TWIK3-FF1-Sac/TWK3-RR2-SalI and TWK3-RR1-NotI/TWK3-FF2-SalI were fractionated on 1.2% agarose gels, gel-purified, and cloned into pCRII vector using the TOPO TA kit (Invitrogen). Four independent clones were then isolated, DNA purified, and sequenced with M13 forward and reverse primers, TWK3 -F1, TWK3-R2, TWK5-F1, TWK5-R2, TWK3-F4, TWK3-R4, TWK5-F4, and TWK5-R4 primers, and the following primers:

TWK3-SF5: TCGCCGAAGGGAGCGGACTGAACG SEQ ID NO:35

TWK3-SF6: GTCCATCGCCTATTGCTCGCTGTA SEQ ID NO:36

TWK3-SR5: CCCTACTTCTCCCAGGTGCCGAGT SEQ ID NO:37

TWK3-SF6: AGTAGGCGGAATCCAAGAAGGACC SEQ ID NO:38

From the consensus sequence, one clone for each of the two fragments was digested with 1) SacII/SalI and 2) NotI/SalI, respectively. The two fragments were then directionally cloned into the expression vector p1E1-3 (Novagen Inc., Madison, Wis.) which had been digested with SacII/NotI and purified.

The TWIK3 nucleic acid sequence (SEQ ID NO:3) is greater than 99% identical to SEQ ID NO:13,872 disclosed in the co-pending application Ser. No. 09/270,767. The predicted amino acid sequence (SEQ ID NO:4) for TWIK3 is greater than 99% identical to SEQ ID NO:45,442 disclosed in the co-pending application Ser. No. 09/270,767. The differences between the two sequences are at residues 242 and 566.

The predicted protein sequence (SEQ ID NO:4) of TWIK3 was analyzed using BLAST against known protein databases. The longest contiguous stretch of identical amino acid sequence was 8, shared with C. elegans clone C24H11 (GI 1694994); the longest contiguous stretch of similar amino acids was 16, shared with the same clone.

6.2.3. TWIK4

TWIK4 was discovered as an EST clone found in the Exelixis FlyTag™ cDNA database, as described above. To obtain full-length cDNA clones, available cDNA libraries were screened. P1 library filters were also screened to generate genomic coverage and cytological information.

One oligo-dT-primed and one random-primed embryonic Drosophila cDNA libraries were kindly provided by Dr. Rubin (Berkeley Drosophila Genome Project, Rubin Lab, LSA Rm. 539, U.C. Berkeley, Berkeley, Calif. 94720-3200). The random-primed library was plated out at a "low density" (5,000 pfu/plate×20 plates) and the oligo-dt library was plated out at "high density" (50,000 pfu/plate×20 plates) according to published protocols (Sambrook et al., supra). Since the Drosophila genome is approximately 160 Mb and the clones are about 1 kb in length this should respectively provide 62.5×coverage and 625×coverage. Plaques were plated out as described by Sambrook et al., supra.

Primers were made from the highly conserved P domains of TWIK4 to perform PCR reactions on Drosophila genomic DNA:

TWIK4.F1: CCTCACTGACGGTGATCACGACCA SEQ ID NO:39

TWIK4.R1: CGCCCGAATGTTGTAACGACCT SEQ ID NO:40

PCR products were used as probes to hybridize onto library filters, as described above. Positive clones were picked, replated, and rescreened by hybridization as described above. Positive clones were picked and confirmed by PCR using the same primers and conditions for amplifying the original probes. The clones were then sequenced using T3 and T7 vector primers, PCR primers indicated before, and the following:

TWIK4.F2: TGCCGACAGGGATAAGGTGGAGGT SEQ ID NO:41

TWIK4.F3: CTGGTGCCAGGCGATCGTGTGATA SEQ ID NO:42

TWIK4.F4: TTCGGTCGTTGGGAGGACTGGAAC SEQ ID NO:43

TWIK4.R2: CGCCAATGTTGGACAGGTAGAGCA SEQ ID NO:44

TWIK4.R3: AAGGACTTGGCCAGGACGTCGC SEQ ID NO:45

TWIK4.R4: GGCAGATGCGACATAGGCACACCT SEQ ID NO:46

The sequence data obtained resulted in a 1.7 kb contig, of which the ORF was about 1.2 kb in length.

For genomic library screening the same PCR products for the hybridization of cDNA libraries were used for hybridization onto P1 high density filters. The hybridizations produced 4 positive clones. Comparison of these clones to the BDGP database revealed all to map to contig Dm 0746, located on cytological band 44A1-44B2. Clones in this contig have been sequenced by the BDGP, so further genomic sequencing was not necessary.

A BLAST comparison of the predicted TWIK4 amino acid sequence (SEQ ID NO:6) with sequences deposited in the public databases revealed a longest contiguous stretch of identical amino acids of 7 amino acids, shared with C. elegans clone C24H11.8(GI 3874493); the longest contiguous stretch of similar amino acids was 15, shared with the same clone.

6.2.4. TWIK 5

TWIK 5 was discovered as unanalyzed genomic P1 sequence found in BDGP database (P1s D345, D349, D355= DS00191, DS00050, DS05369, AC005894, GI 3818342). The cDNA clone was predicted using Genscan. In order to obtain a full-length cDNA clone, cDNA libraries were screened. The P1(DS05369) genomic clone, located at cytological band 46B1-46B2, was re-sequenced to verify the public sequences. cDNA library screening was performed as described above. The PCR primers were:

TWIK5.F1: CGAACGCAACTGGACGAT SEQ ID NO:47

TWIK5.R1: CGCACTGCTGGCAGATGG SEQ ID NO:48

TWIK5.F2: GCAACTGTCCGCACGGAA SEQ ID NO:49

TWIK5.R2: GGCAATGCGTTTGCACTT SEQ ID NO:50

Three positive cDNA clones were identified. A comparison of the predicted TWIK5 amino acid sequence (SEQ ID NO:8) with sequences deposited in the public databases revealed a longest contiguous stretch of identical amino acids of 7 amino acids, shared with mouse TREK1 potassium channel subunit (GI 4584799); and a longest similar stretch of 17 amino acids, shared with *C. elegans* clone C24H11.8(GI 3874493). Subsequent to the cloning and initial BLAST analysis of TWIK5, a fill-length, unannotated sequence that encodes TWIK5 was deposited in the public databases by the BDGP (GI 5052537).

6.2.5. TWIK6

TWIK6 was discovered as an unannotated EST clone from the BDGP database. In order to obtain full-length clones, the available cDNA libraries were screened as described above. To obtain genomic clones both P1 and BAC libraries (from the BDGP and also available from Research Genetics) were screened as described above.

The following primers were used for screening cDNA libraries:

TWIK6.F1: CACCATGACAACCATCGG SEQ ID NO:51

TWIK6.R1: GGCATTCGTGATGGCTTC SEQ ID NO:52

P1 and BAC genomic library screening was carried out. The P1 filter produced 2 positive clones while the BAC filter produced 7. The clones were verified by PCR. Comparison of the results to the BDGP databases did not reveal a cytological location.

A BLAST comparison of the predicted TWIK6 amino acid sequence (SEQ ID NO:9) with sequences deposited in the public databases revealed a longest contiguous stretch of identical amino acid sequence of 6 amino acids, shared with *C. elegans* clone T28A8.1 (GI 3880336); the longest stretch of contiguous similar amino acids was 14, also shared with the same clone.

6.2.6. TWIK7

TWIK7 was discovered as an EST clone in the Exelixis FlyTag™ cDNA database, as described above. To obtain full-length clone, the available cDNA libraries were screened. To get genomic coverage and cytological location, both P1 and BAC libraries were screened.

cDNA libraries were screened as described above, using the following primers:

TWIK7.F1: GACCTCATCTGTGTTGTG SEQ ID NO:53

TWIK7.R1: GAGGGCTGGAGCTACTTC SEQ ID NO:54

TWIK7.F2: GCACATGGACGAGATGTT SEQ ID NO:55

TWIK7.R2: CACATCGCCCTCCAGCTT SEQ ID NO:56

Five positive cDNA clones were identified, and re-screened as described above. The clones were then sequenced, as described above, using T3 and T7 vector primers, PCR primers indicated above, and the following:

TWIK7.F3: CAACATCTCGTCCATGTG SEQ ID NO:57

TWIK7.F4: GAAGCTGGAGGGCGATGTG SEQ ID NO:58

TWIK7.R3: CACAACACAGATGAGGTC SEQ ID NO:59

TWIK7.R4: GAAGTAGCTCCAGCCCCTC SEQ ID NO:60

These sequences produced a 2.0 kb contig, of which 1.2 kb constituted an ORF.

Genomic screening was carried out. The P1 filter produced 3 positive clones while the BAC filter produced 7. Comparison of these results with the databases from BDGP did not produce a cytological location. One P1 clone was submitted for full-length sequencing.

Subsequent to the above-described cloning of the TWIK7 coding region, an unfinished genomic sequence of a BAC clone covering the TWIK7 gene was entered in the public databases (AC007646, GI 4895159, BACR03J04=BAC D687).

Nucleotides 472–909 of TWIK7 (SEQ ID NO:11) are 100% identical to SEQ ID NOs:56 and 15,338 disclosed in the co-pending '767 application, and SEQ ID NO:355 in the co-pending '849 application. Nucleotides 1011–1227 of SEQ ID NO:11 are greater than 99% identical to nucleotides 1–217 of both SEQ ID NOs:9,024 and 24,306 of the '767 application, and SEQ ID NO: 14,589 in the co-pending '849 application. Amino acid residues 158 to 303 of SEQ ID NO:12 are 100% identical to SEQ ID NO:31,685 of the '767 application.

A comparison of the predicted TWIK 7 amino acid sequence (SEQ ID NO: 12) with sequences deposited in the public databases revealed a longest contiguous stretch of identical amino acid sequence of 22 amino acids, shared with *Homo sapiens* TWIK-related acid-sensitive $K^+$ channel (GI 2465542); the longest contiguous stretch of similar amino acids was 32, shared with the same sequence.

6.2.7. cpbTWIK1

The Leptinotarsa cpbTWIK1 nucleic acid sequence was discovered as an EST clone in the Exelixis ColTag™ cDNA database, as described above. It was sequenced from the 5' end and then re-sequenced from both ends, but the sequence was not overlapping. Primers were made in the 5' and 3' ends to obtain overlapping sequences. The following primers were used for sequencing:

CPBT.5'A TGTGTAGCGGAGCAGCGGTTTT SEQ ID NO:61

CPBT.5'B AGCGGTTTTCAGTTACTTTGAGG SEQ ID NO:62

CPBT.5'C. GCGGTTTTCAGTTACTTTGAGGC SEQ ID NO:63

CPBT.5'D GCACCTGAGGAACGGGCACTGAG SEQ ID NO:64

CPBT.3'A CCCGGAACTGGCTAACCTCACTT SEQ ID NO:65

The sequence reactions produced a 1 kb contig representing the full-length sequence of cpbTWIK1. The translation of the nucleotide sequence was made by analyzing BLAST results. A comparison of the predicted cpbTWIK1 amino acid sequence (SEQ ID NO:14) with sequences deposited in the public databases revealed a longest contiguous stretch of identical amino acid sequence of 7 amino acids, shared with *Oryctolagus cuniculus* rabKCNK1 (GI 2213891); the longest stretch of similar amino acids was 19, shared with the same sequence.

6.2.8. Features of TWIK Channel Nucleic Acid Sequences

Table II summarizes the features of the above-described TWIK channel nucleic acid sequences and their encoded proteins. "NA" refers to nucleic acid and "AA" refers to amino acid.

TABLE II

| NAME | CODING SEQUENCE LENGTH (NA) | TRANS-MEMBRANE (TM) DOMAINS (NA) | TRANS-MEMBRANE (TM) DOMAINS (NA) | PORE (P) DOMAINS (NA) | PORE (P) DOMAINS (AA) |
|---|---|---|---|---|---|
| TWIK2 | 2988 | TM1: 1668–1716<br>TM2: 2028–2076<br>TM3: 2412–2460<br>TM4: 2568–2616 | TM1: 556–572<br>TM2: 676–692<br>TM3: 804–820<br>TM4: 856–872 | P1: 1902–1971<br>P2: 2433–2499 | P1: 634–657<br>P2: 811–833 |
| TWIK3 | 2193 | TM1: 102–150<br>TM2: 507–555<br>TM3: 1902–1950<br>TM4: 2076–2124 | TM1: 34–50<br>TM2: 169–185<br>TM3: 634–650<br>TM4: 692–708 | P1: 405–477<br>P2: 1938–2007 | P1: 135–159<br>P2: 646–669 |
| TWIK4 | 1188 | TM1: 102–150<br>TM2: 477–525<br>TM3: 861–909<br>TM4: 1065–1113 | TM1: 34–50<br>TM2: 159–175<br>TM3: 287–303<br>TM4: 355–371 | P1: 381–453<br>P2: 933–1002 | P1: 127–151<br>P2: 311–334 |
| TWIK5 | 3465 | TM1: 222–282<br>TM2: 663–723<br>TM3: 3147–3210<br>TM4: 3339–3411 | TM1: 74–94<br>TM2: 221–241<br>TM3: 1049–1070<br>TM4: 1113–1137 | P1: 573–642<br>P2: 3228–3297 | P1: 191–214<br>P2: 1076–1099 |
| TWIK6 | 605 (incomplete) | TM: 124–191 | TM: 41–64 | P: 45–105 | P: 15–35 |
| TWIK7 | 1229 | TM1: 27–75<br>TM2: 327–375<br>TM3: 483–531<br>TM4: 672–720 | TM1: 9–25<br>TM2: 109–125<br>TM3: 161–177<br>TM4: 224–240 | P1: 234–303<br>P2: 552–621 | P1: 78–101<br>P2: 184–207 |
| cpb-TWIK1 | 1082 | TM1: 324–366<br>TM2: 654–714<br>TM3: 798–879<br>TM4: 1008–1074 | TM1: 46–60<br>TM2: 156–176<br>TM3: 204–231<br>TM4: 274–296 | P1: 561–633<br>P2: 891–963 | P1: 125–149<br>P2: 235–259 |

6.2.9. Blast Results for the TWIK Nucleic Acid Sequences

Nucleotide and amino acid sequences for each of the TWIK nucleic acid sequences and their encoded proteins were searched against all available nucleotide and amino acid sequences in the public databases, using BLAST (Altschul et al., supra). Table 3 below summarizes the results. In each case, the 5 most similar sequences are listed.

TABLE 3

| TWIK | DNA BLAST | | PROTEIN BLAST | |
|---|---|---|---|---|
| | GI# | DESCRIPTION | GI# | DESCRIPTION |
| TWIK2 | 3006211 = AC004313 | D502368 (P1 D205) Drosophila | 3876514 (Z92832) | F31D4.7 C. elegans clone |
| | 1877065 | C. elegans clone C18D11 | 1877088 (Z92783) | F14H10 C. elegans clone |
| | 1694994 | C. elegans clone C24H11 | 4584799 = AAC53005 (U73488) | TREK-1 K + channel subunit Mus musculus |
| | 3150442 | AF033017 Mus musculus TWIK-1 | 3808068 | Drosophila two P domain K + channel ORK1 |
| | 392542 | AF084830 Homo sapiens two pore domain K + channel, TASK2 | 1916869 | TWIK-1 K + channel Mus musculus |
| TWIK3 | 3779012 = AC005847 | Drosophila DNA sequence (P1s DS03179 (D226), DS06357 (D230), DS03404 (D231), DS06962 (D232), and DS07291 (D240)) | 1877065 = Z92826 | C. elegans DNA from clone C18D11 |
| | 416040 U01842 | Drosophila kinesin-like protein mRNA | 1694994 Z81475 | C. elegans cosmid C24H11 |
| | 4056406 = AC005473 | Drosophila P1 clone DS02142 | 3924830 = CAA98957 (Z74475) | Predicted using Genefinder; similar to K + channel protein [C. elegans] |
| | 1772445 = D87747 | Mus musculus mRNA for murine CXCR-4 | 4103376 = AAD09338 (AF022821) | putative K + channel DP4 [Mus musculus] |
| | 2465543 = AF006824 | Mus musculus TWIK-related acid-sensinve K + channel (TASK) mRNA | 4584799 = AAC53005 (U73488) | TREK-1 K + channel subunit [Mus musculus] |
| TWIK4 | 4056406 = AC005473 | Drosophila P1 clone DS02142 | 3874493 = CAB03914 (Z81475) | C. elegans clone C24H11.8 |
| | 3779012 = AC005847 | Drosophila DNA sequence (P1s DS03179 (D226), DS06357 (D230), | 3880336 = CAB07286 | C. elegans clone T28A8.1 |

TABLE 3-continued

| | DNA BLAST | | PROTEIN BLAST | |
|---|---|---|---|---|
| TWIK | GI# | DESCRIPTION | GI# | DESCRIPTION |
| | | DS03404 (D231), DS06962 (D232), and DS07291 (D240)) | (Z92813) | |
| | 1869276 = Z92062\|FR0008252 | *F. rubripes* GSS sequence, clone 19OO22bB9 | 3452417 = AAC32863\| (AF083652) | Putative K + channel subunit n2P38 *C. elegans* |
| | 3818343 = AC005430 | Drosophila P1 clone DS04740 | 2429407 = AAC71151 (AF025454) | Contains similarity to outward-rectifier K + channels *C. elegans* |
| | 157452 = M23221 | DROFSHA Drosophila fsh membrane protein | 3924830 = CAA98957 (Z74475) | Predicted using Genefinder; similar to potassium K + protein *C. elegans* |
| TWIK5 | 3818342 = AC005894. | Drosophila P1 clones DS00050, D500191, and DS05369 | 4584799 = AAC53005 (U73488) | TREK-1 K+ channel subunit [*Mus musculus*] |
| | 3261554 = AL022022.1 MTV023 | Mycobacterium tuberculosis H37Rv complete genome; segment 148/162 | 3874493 = CAB03914 (Z81475) | *C. elegans* clone C24H11.8 |
| | 2102687 U58944.1 DMU58944 | *Dissostichus mawsoni* AFGP antifreeze glycopeptide polyprotein precursor gene | 1405526 | *C. elegans* clone R04F11.4 |
| | 1633571 = U52064.1 KSU52064 | Kaposi's sarcoma-associated herpes-like virus ORF73 homolog gene | 3924830 = CAA98957\| (Z74475) | Predicted using Genefinder; similar to potassium channel protein *C. elegans* |
| | 2065526 = U75698.1 KSU75698 | Kaposi's sarcoma-associated herpesvirus long unique region | 3880336 = CAB07286\| (Z92813) | *C. elegans* clone T28A8.1 |
| TWIK6 | 3943225 = AI293818 | LP07049.5prime LP Drosophila larval-early pupal cDNA clone | 3880336 = e1349878 | *C. elegans* clone T28A8.1 |
| | 1695114 = Z82073 | *C. elegans* cosmid W06D12 P34410 | 465874 = | *C. elegans* TWK-8 protein |
| | 1439623 = U64598 | *C. elegans* cosmid C52B9 S44635 | 1078847 = | *C. elegans* f22b7.7 protein |
| | 1255391 = U53150 | *C. elegans* cosmid F20A1 | 156306 | *C. elegans* cosmid F22B7 |
| | 2653149 = Z82073 | *C. elegans* cosmid W06D12 AAB16491 | 1613511 = | SEQ4 from U.S. Pat. No. 5559026 |
| TWIK7 | 4895159 = AC007646 | Unfinished BAC clone BACR03J04 = BAC D687 | 2429407 = AAC71151\| | contains similarity to outward-rectifier K + channels [*C. elegans*, TWIL23] |
| | 2465541 = AF006823 | *Homo sapiens* TWIK-related acid-sensitive K + channel (TASK) mRNA | 3452417 = AAC32863\| | *C. elegans* putative K + channel subunit n2P38 |
| | 3043543 = AB008537 | *Mus musculus* mRNA for cTBAK | 2465542 = AAC51777 | *Homo sapiens* TWIK-related acid-sensitive K + channel |
| | 3149958 = AB013345 | *Mus musculus* mRNA for cTBAK | 2809391 = AAC39952 | *Rattus norvegicus* TWIK-related acid-sensitive K + channel |
| | 2465543 = AF006824 | *Mus musculus* TWIK-related acid-sensitive K + channel (TASK) mRNA | 3043544 = BAA25436 | *Mus musculus* cTBAK |
| cpbTWIK1 | 4581226 = AL020988 | *C. elegans* DNA clone Y80D3 | 2213891 = AAB61602 | *Oryctolagus cuniculus* rabKCNK1 |
| | 4581216 = Z95399 | *C. elegans* clone Y39B6 | 2135518 = S65566 | *Homo sapiens* inward rectifier K + channel TWIK-1 |
| | 1503390 = C06614 | *Rattus norvegicus* pancreatic islet cDNA | 1086491 = AAB01688 | *Homo sapiens* TWIK-1 |
| | | | 1916295 = AAB51147 | *Homo sapiens* K + channel KCNO1 |
| | | | 2811120 = AAB97878 | *Homo sapiens* two P domain K + channel subunit |

Table IV further summarizes the BLAST results for each TWIK channel amino acid sequence. The "% Identity" column indicates, for each TWIK channel amino acid sequence, the longest stretch of contiguous amino acids that is novel with respect to prior art sequences as determined by BLAST. Thus, for example, any contiguous stretch of 8 amino acids of the TWIK2 amino acid sequence (SEQ ID NO:2) is novel over sequences in public databases. The "% Similarity" column shows the longest stretch of contiguous amino acids for which there are no sequences contained within public database sharing 100% sequence similarity. For example, for any contiguous stretch of 15 amino acids of the TWIK2 channel protein, there are no sequences in the public databases that share 100% sequence identity.

TABLE IV

| TWIK | 100% Identity Length (x) | 100% Similarity Length (y) |
|---|---|---|
| TWIK 2 (SEQ ID NO: 2) | 8 | 15 |
| TWIK 3 (SEQ ID NO: 4) | 9 | 17 |
| TWIK 4 (SEQ ID NO: 6) | 8 | 16 |
| TWIK 5 (SEQ ID NO: 8) | 8 | 18 |
| TWIK 6 (SEQ ID NO: 10) | 7 | 15 |
| TWIK 7 (SEQ ID NO: 12) | 23 | 33 |
| cpbTWIK1 (SEQ ID NO: 14) | 8 | 20 |

6.3. Example 3

TWIK Expression Analysis

TWIK expression analysis was carried out by in situ hybridization to Drosophila embryonic and larval tissues for the Drosophila TWIKs, using the cDNAs to generate antisense probes on Drosophila embryos and larval tissue. Antisense DIG-labeled RNA probes were synthesized using the Roche (NJ) Dig RNA Labeling Kit and T7 RNA polymerase according to the in situ hybridization protocol of BDGP methods page (http://www.fruitfly.org/methods/).

The results showed that TWIK2 is expressed in the progenitor and developing muscle cells of the embryo and larval musculature. TWIK3 is expressed in the developing esophagus and hindgut of the embryo. TWIK6 is expressed in a region of the gut, in band of cells around the larval proventriculus. This most likely corresponding to the described imaginal ring that will give rise to adult tissues. TWIK7 is highly expressed in neuronal tissues: during late differentiation of the embryonic central nervous system, throughout the larval CNS during $1^{st}$ instar and in the brains of $3^{rd}$ instar larvae, particularly the optic lobes.

6.4. Example 4

Compound Screening Using TWIK Expression Systems cDNAs encoding TWIK channels of interest are cloned into baculovirus-compatible vectors (e.g. pIE-1 series, Novagen, Madison, Wis.) or mammalian cell culture-compatible vectors (e.g. pCDNA, Invitrogen, Carlsbad, Calif.) using standard methods. The resultant constructs are transiently transfected into insect or mammalian cell cultures, respectively. The transiently transfected cell lines are typically used 24–48 hours following transfection for electrophysiology studies. Whole cell recordings, using the voltage clamp technique, are taken on the transfected cells and compared with recordings taken from cells transfected with vector only. The cells are injected with a current of designated intensity for brief periods (up to 200 milliseconds). A resultant current, generated by the cell in returning to the resting potential, is recorded. The amplitude and duration of this current indicates the presence of a functional channel in the transfected cells. Current injections are repeated with increasing amperage—the resultant channel-generated current should increase to reflect the increased injected current. A channel-blocking compound may then be applied to the cell culture in the concentration range of about $1 \times 10^{-9}$ to $1 \times 10^{-6}$ M to determine the effect on the channel activity. If the compound inhibits channel activity, a resultant current is not generated in response to the injected current. The compound may be washed out of the cell culture and another compound tested in series.

In a second type of experiment, the resting potential of transfected cells is compared to that of control cells. For potassium leak channels e.g. the TWIKS, a depolarized resting potential is observed in the transfected cells. A series of compounds can then be tested for interactions with the expressed channel by applying each compound and measuring any resultant changes in cellular resting potential.

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims. The disclosure of each reference cited herein, including patents, patent applications, and other references, is hereby incorporated herein by reference in its entirety for all purposes.

What is claimed is:

1. An isolated nucleic acid comprising the nucleotide sequence of SEQ ID NO: 11.

2. A vector comprising the nucleic acid molecule of claim 1.

3. An isolated host cell comprising the vector of claim 2.

4. A process for producing a TWIK channel protein comprising culturing the host cell of claim 3 under conditions suitable for expression of said TWIK channel protein and recovering said TWIK channel protein.

5. An isolated nucleic acid that encodes the amino acid sequence of SEQ ID NO 12.

* * * * *

SEQUENCE LISTING

```
<160> NUMBER OF SEQ ID NOS:  70

<210> SEQ ID NO 1
<211> LENGTH: 2988
<212> TYPE: DNA
<213> ORGANISM: Drosophila melanogaster

<400> SEQUENCE: 1
atgacgagca cgagcacaaa gatagatcgc gaaagtagca cacgactgcg gctggacaag      60
atggagcagc cgatggacgc caggcagcag cagcgccatc gaaggcgcct gggtcgcagc     120
caccgggaac cgacgcccgt cactggagac gccctgcccc aggacgatgc cagtccggat     180
gccctccctg atccatcacc tcagatggtg cgcatgcaga tcaggccacc cggctcgatg     240
tccgcccacg agagcaagat cctgcgaaag cgggacaagt ccttcgccag ctcctcggcg     300
```

-continued

```
cgtagtcaat cgcagccacg ggaggctgag aagctgagta gtccggatgc caatcatctg    360
atcaagcatc gcagcctctc ctcgccgcgg cacaaggagg agtccagcga gagtgagctg    420
accaccggca gcagtagtca gcagcaaagg cccattccta atcttggcca gacacaggat    480
acgctaagca gattggagca gaatctgcag cgcttcgagg acgaacgacg gcgtttcgag    540
gccgagaaga ggctctttga gcgcgagaag cgggagcaca agatgcgcca tcgccagcag    600
ctggacaacg aggagcgcaa gcgcctcctg cagagctacc gcaagctcag cgatcgcatc    660
cagctgccgc aggacgagga ggaacggcgc cgcctcatcc acagcctgcg tctgcagcga    720
cacgaggcgc ccaagactcg gggtcgcaat cgaagtagcg gctacgatga gtcctccacc    780
cagttcagct cctccgatgc cgatgcgacg gaggagactc acccgcggcc ccgagcacct    840
aagattcccc agggctttgt ggcagcccca atccgcggcg cacctccacc gccgccatcg    900
gcgtcgacag ctccaaaacc accggaaagg ctgtctgtga gtcgcaacaa ctccctgtcg    960
cccgtgagac cacagcgacg atccaagact ccggagcaac gggaggagat cctccggaag   1020
cacgagtact tggaggtggg cgagtccaga gacgaggtga taaagccccg catctcggag   1080
gcagaacagc agtcggagct gatgcaaaag tacatggagg ccgctgagcg ggcggcaaaa   1140
gcggaggccg ccctggcgga gcaaatcctg acggcggagg gagtgcgtcg cagtcacagc   1200
ttgagattag cggataagga agagaagcct caaaagcgca gctccagttt ggagcgtcca   1260
ctaagaccca agcgatcggg cagtttggaa agaaaggaac aggtaactca agagctcctt   1320
gagggaacta ctacaaatga agctgatacg gaaccaaaat ctcttgggga tcaacccttg   1380
ttgccagagg aatccatctc agaggcgaaa cccaaagtta ccttatggca gcggctgaaa   1440
aatctgttta ggcgaaagaa gaagattcag gcaaagggcg aagatgtcac agatctgtcc   1500
acagaattgc cactggagaa gttggcctcc aggggtctgc tgtacagttt cagcctagaa   1560
gcccggcatg aatggaaacg cctcaagctg gactatcccc aaaaggtgaa ggaactgcgt   1620
cagctacgca acaggtgcat tgcctatctc atctgcatgg ctatgcttct gggattcgga   1680
ggactcctgt tccggtacac ggaaggagca gcggagaata tatacaagtg cgaggtgcgc   1740
aaggtgaagc gggatttcat agaccgactg tgggacgtca gccacaacat gagagaggag   1800
gactggaagt ctcttgcccg ccagaagctg cgcagcttcg aggatgaact aaataattta   1860
gccgagttgg gactacgccg ctatccgggc caaaagtcct ggaactttgt caattgcttc   1920
atcttctgtt ggaccgtgat cacaactata ggttacggcc acatcactcc aaagacgggc   1980
atgggtcgat ccctgaccat cgtctatgcc atcatcggca tccccatgtt cctgatcgtg   2040
ctggccgatc tgggcaagtt attcacgcgc tgcgtcaagt tcctgtgggt gtatgtgcga   2100
cggatgtact acacgcgctc ctgccgccgg atacgaaagc agcagcagat ccggagcgcc   2160
atgacaggct caatacgat gtacgacatg gccatccgca ggccgagcat gttcttcagc   2220
aactctgcgc cagagaacga tgaggagtcg caggcggatg ccgaggccgc aagatcggtg   2280
ggcacctcgc acccggagac acccacatca ccctatccag agaccttcga ggtggacgac   2340
gagttcaatt tgccagtgtc ggtggcctcg ctgctgctca ttacgtacat cctcctagga   2400
tccttcggct ttctaatgat ggagcccagc tggactccac tggatgcctt ctactacgtg   2460
ttcatctcga tgtccacaat tgggttcggc gacctggtgc ccagtaatcc cttctacgta   2520
atggtcagca tgatctatct gatgttcggc ttggccctga cctccatgtt catcaatgtg   2580
gtgcagatca agctgagcga tcacttcaaa atggccagcg ccaaagtggg cgccaccatt   2640
```

-continued

```
ggcatgaaca tgaccagcga gcttggtgat gagggcggct cccaggtgaa gactccctcc    2700
gagcttgcct cggtgcacgg ttcgcgactg gacaggatcg aggaggatgg ccaggaggcg    2760
aatggcaatg ccactcccc ggtgccacca ctcacctcga tcctgcgcgc accgcgtcct    2820
ctatcgccgg cgtccaatgg agtggatgct aatggagttg gagccgatgc tgttggagct    2880
ggggatgtta ctccgccacc tctgctgccc aggcgtcagg tttccgtgga tccccagccg    2940
ccggcggagg gggagaacaa gaagaagaaa agcacaggt ttttctag                 2988
```

<210> SEQ ID NO 2
<211> LENGTH: 995
<212> TYPE: PRT
<213> ORGANISM: Drosophila melanogaster

<400> SEQUENCE: 2

```
Met Thr Ser Thr Ser Thr Lys Ile Asp Arg Glu Ser Ser Thr Arg Leu
  1               5                  10                  15

Arg Leu Asp Lys Met Glu Gln Pro Met Asp Ala Arg Gln Gln Gln Arg
             20                  25                  30

His Arg Arg Leu Gly Arg Ser His Arg Glu Pro Thr Pro Val Thr
         35                  40                  45

Gly Asp Ala Leu Pro Gln Asp Ala Ser Pro Asp Ala Leu Pro Asp
     50                  55                  60

Pro Ser Pro Gln Met Val Arg Met Gln Ile Arg Pro Gly Ser Met
 65                  70                  75                  80

Ser Ala His Glu Ser Lys Ile Leu Arg Lys Arg Asp Lys Ser Phe Ala
                 85                  90                  95

Ser Ser Ser Ala Arg Ser Gln Ser Gln Pro Arg Glu Ala Glu Lys Leu
            100                 105                 110

Ser Ser Pro Asp Ala Asn His Leu Ile Lys His Arg Ser Leu Ser Ser
        115                 120                 125

Pro Arg His Lys Glu Glu Ser Ser Glu Ser Glu Leu Thr Thr Gly Ser
    130                 135                 140

Ser Ser Gln Gln Gln Arg Pro Ile Pro Asn Leu Gly Gln Thr Gln Asp
145                 150                 155                 160

Thr Leu Ser Arg Leu Glu Gln Asn Leu Gln Arg Phe Glu Asp Glu Arg
                165                 170                 175

Arg Arg Phe Glu Ala Glu Lys Arg Leu Phe Glu Arg Glu Lys Arg Glu
            180                 185                 190

His Lys Met Arg His Arg Gln Gln Leu Asp Asn Glu Glu Arg Lys Arg
        195                 200                 205

Leu Leu Gln Ser Tyr Arg Lys Leu Ser Asp Arg Ile Gln Leu Pro Gln
    210                 215                 220

Asp Glu Glu Arg Arg Arg Leu Ile His Ser Leu Arg Leu Gln Arg
225                 230                 235                 240

His Glu Ala Pro Lys Thr Arg Gly Arg Asn Arg Ser Ser Gly Tyr Asp
                245                 250                 255

Glu Ser Ser Thr Gln Phe Ser Ser Asp Ala Asp Ala Thr Glu Glu
            260                 265                 270

Thr His Pro Arg Pro Arg Ala Pro Lys Ile Pro Gln Gly Phe Val Ala
        275                 280                 285

Ala Pro Ile Arg Gly Ala Pro Pro Pro Ser Ala Ser Thr Ala
    290                 295                 300

Pro Lys Pro Pro Glu Arg Leu Ser Val Ser Arg Asn Asn Ser Leu Ser
305                 310                 315                 320
```

-continued

Pro Val Arg Pro Gln Arg Arg Ser Lys Thr Pro Glu Gln Arg Glu Glu
                325                 330                 335

Ile Leu Arg Lys His Glu Tyr Leu Glu Val Gly Glu Ser Arg Asp Glu
            340                 345                 350

Val Ile Lys Pro Arg Ile Ser Glu Ala Glu Gln Gln Ser Glu Leu Met
        355                 360                 365

Gln Lys Tyr Met Glu Ala Ala Glu Arg Ala Ala Lys Ala Glu Ala Ala
    370                 375                 380

Leu Ala Glu Gln Ile Leu Thr Ala Glu Gly Val Arg Arg Ser His Ser
385                 390                 395                 400

Leu Arg Leu Ala Asp Lys Glu Glu Lys Pro Gln Lys Arg Ser Ser Ser
            405                 410                 415

Leu Glu Arg Pro Leu Arg Pro Lys Arg Ser Gly Ser Leu Glu Arg Lys
        420                 425                 430

Glu Gln Val Thr Gln Glu Leu Leu Glu Gly Thr Thr Thr Asn Glu Ala
    435                 440                 445

Asp Thr Glu Pro Lys Ser Leu Gly Asp Gln Pro Leu Leu Pro Glu Glu
    450                 455                 460

Ser Ile Ser Glu Ala Lys Pro Lys Val Thr Leu Trp Gln Arg Leu Lys
465                 470                 475                 480

Asn Leu Phe Arg Arg Lys Lys Ile Gln Ala Lys Gly Glu Asp Val
            485                 490                 495

Thr Asp Leu Ser Thr Glu Leu Pro Leu Glu Lys Leu Ala Ser Arg Gly
            500                 505                 510

Leu Leu Tyr Ser Phe Ser Leu Glu Ala Arg His Glu Trp Lys Arg Leu
        515                 520                 525

Lys Leu Asp Tyr Pro Gln Lys Val Lys Glu Leu Arg Gln Leu Arg Asn
    530                 535                 540

Arg Cys Ile Ala Tyr Leu Ile Cys Met Ala Met Leu Leu Gly Phe Gly
545                 550                 555                 560

Gly Leu Leu Phe Arg Tyr Thr Glu Gly Ala Ala Glu Asn Ile Tyr Lys
            565                 570                 575

Cys Glu Val Arg Lys Val Lys Arg Asp Phe Ile Asp Arg Leu Trp Asp
            580                 585                 590

Val Ser His Asn Met Arg Glu Glu Asp Trp Lys Ser Leu Ala Arg Gln
        595                 600                 605

Lys Leu Arg Ser Phe Glu Asp Glu Leu Asn Asn Leu Ala Glu Leu Gly
    610                 615                 620

Leu Arg Arg Tyr Pro Gly Gln Lys Ser Trp Asn Phe Val Asn Cys Phe
625                 630                 635                 640

Ile Phe Cys Trp Thr Val Ile Thr Thr Ile Gly Tyr Gly His Ile Thr
            645                 650                 655

Pro Lys Thr Gly Met Gly Arg Ser Leu Thr Ile Val Tyr Ala Ile Ile
            660                 665                 670

Gly Ile Pro Met Phe Leu Ile Val Leu Ala Asp Leu Gly Lys Leu Phe
        675                 680                 685

Thr Arg Cys Val Lys Phe Leu Trp Val Tyr Val Arg Arg Met Tyr Tyr
    690                 695                 700

Thr Arg Ser Cys Arg Arg Ile Arg Lys Gln Gln Gln Ile Arg Ser Ala
705                 710                 715                 720

Met Thr Gly Phe Asn Thr Met Tyr Asp Met Ala Ile Arg Arg Pro Ser
            725                 730                 735

```
Met Phe Phe Ser Asn Ser Ala Pro Glu Asn Asp Glu Glu Ser Gln Ala
            740                 745                 750
Asp Ala Glu Ala Ala Arg Ser Val Gly Thr Ser His Pro Glu Thr Pro
            755                 760                 765
Thr Ser Pro Tyr Pro Glu Thr Phe Glu Val Asp Asp Glu Phe Asn Leu
            770                 775                 780
Pro Val Ser Val Ala Ser Leu Leu Ile Thr Tyr Ile Leu Leu Gly
785                 790                 795                 800
Ser Phe Gly Phe Leu Met Met Glu Pro Ser Trp Thr Pro Leu Asp Ala
                805                 810                 815
Phe Tyr Tyr Val Phe Ile Ser Met Ser Thr Ile Gly Phe Gly Asp Leu
                820                 825                 830
Val Pro Ser Asn Pro Phe Tyr Val Met Val Ser Met Ile Tyr Leu Met
                835                 840                 845
Phe Gly Leu Ala Leu Thr Ser Met Phe Ile Asn Val Val Gln Ile Lys
            850                 855                 860
Leu Ser Asp His Phe Lys Met Ala Ser Ala Lys Val Gly Ala Thr Ile
865                 870                 875                 880
Gly Met Asn Met Thr Ser Glu Leu Gly Asp Glu Gly Gly Ser Gln Val
                885                 890                 895
Lys Thr Pro Ser Glu Leu Ala Ser Val His Gly Ser Arg Leu Asp Arg
            900                 905                 910
Ile Glu Glu Asp Gly Gln Glu Ala Asn Gly Asn Gly His Ser Pro Val
            915                 920                 925
Pro Pro Leu Thr Ser Ile Leu Arg Ala Pro Arg Pro Leu Ser Pro Ala
930                 935                 940
Ser Asn Gly Val Asp Ala Asn Gly Val Gly Ala Asp Ala Val Gly Ala
945                 950                 955                 960
Gly Asp Val Thr Pro Pro Leu Leu Pro Arg Arg Gln Val Ser Val
                965                 970                 975
Asp Pro Gln Pro Pro Ala Glu Gly Glu Asn Lys Lys Lys Lys His
            980                 985                 990
Arg Phe Phe
        995
```

<210> SEQ ID NO 3
<211> LENGTH: 2193
<212> TYPE: DNA
<213> ORGANISM: Drosophila melanogaster

<400> SEQUENCE: 3

| | | | | | |
|---|---|---|---|---|---|
| atgtcgggta | ggcgggccca | atctctgccg | gcgcacatgt | tggagccagc | gaagccgcaa | 60 |
| cgcggacgct | gtgtagctgc | catctgcttc | tcgtggaagg | tgctcacctg | cattgtgtcc | 120 |
| catgtgctgc | tcgtgcttct | cgtggtttcc | tattgcgtgg | gcggtgccta | cctcttccag | 180 |
| catctcgaac | gaccccacga | actagaggtg | aagcgagaca | tacagaatct | tcgcgttaat | 240 |
| ctcacggaga | atatctggct | actgtccgac | gacgcagtgg | tcctaaggga | aagcgattgg | 300 |
| atggccaatg | tcagcaagca | cctggccaat | tttgaaaagc | aaatccttac | ggccatcaag | 360 |
| gccgacggct | gggatggcga | cgaggatctg | cgcaagtccc | agtggacctt | gccggatcc | 420 |
| ctgttctact | cgattattgt | gataacgacc | ataggctatg | gtcacatatc | gccgcgtacg | 480 |
| gattggggca | aggtgacaac | gattttctac | gccattgtgg | gcattccgct | gatgctcatc | 540 |
| tgcttgtcca | acattggcga | tgtcatggcc | acatcatttc | ggtttctgta | ctggagaata | 600 |

-continued

```
tgctgctatg tgtgcacccg cacggccaaa cgtccgagga atgcccgatc ccggcagaga    660
tcgatgcgct ctcagcgcca tgcccgatcc cagccgccgc cctcgttccg gcgctccatg    720
aagatgaccc aacggtctgg gaatgactcg ggtctgggtc cttccatggg tcatgcctat    780
tcagatcccg acctgcgcac catgggccgg ggctacgatg accgcgagtt cggacatcgg    840
agcagtggag gcggacggaa tcgtcgtcag cagcagcagc agcagcattt gcatcacgat    900
cctcgccagc gtcacaccat ttacggagat gggtacgaaa ctcagaccct gaacagatcc    960
aaccgctaca gtagccggca agacaacgg gatcggatga gggacagaca cacggtagaa   1020
agggagcgct actcccgatc ccacttggat gctggatcca ttgaggactt cggtgacatg   1080
caacctcctg cgaaagagc tgccagtgtg cgatcggttc gatcgccaca caatcaggaa   1140
tcttccaaag cgtccagaga actgcatcgt cttcactcgg cacctgggag aagtagggcc   1200
aagtccgtgg atcccaggca cgtttcttca cattacgaag acgtcgacga ggacgtggtg   1260
aggaaaacac caattatacc aaataggtat gctttagatg acttcggggg caacagaaga   1320
caagcagctc caaggagtca atccatgccc agatctgctc accaaaggca acgccagaag   1380
gacagagaac gggaacgatc tccacagccg ccaccgcaga gctcctatcg ccaacagcat   1440
gatagacgag ctggaagtct gggcaggcaa tcatctcgct atggcaacca tctcgaactt   1500
cccgactatg atgctccacc gccgggacgg gaccatcgac gggataggcg tggtcactcc   1560
cagggtcgct acgaggacta cgtggaagag agcttcgatg agggatccct ttacggagac   1620
aataactacg aggattatcc gcctgagcgc caccactcaa ggagtcgaga accaaaaaga   1680
aatcgccgaa gagagcgggc tgaacgtttg ccccctttcc cgagaatcat gtcaccaatg   1740
ggatttccgg tccagcggca aatccgtcgg cgacccagct acgattacga cgacgatgac   1800
tctatgtacg gggatgagta tggggactat ggagatctgc tgcccaagga tcgacctgtc   1860
cccatttggt tatgcgtctt tctggtagtg agctacatcc ttggcggagc tgttcttttt   1920
gcgtactggg agaactggtc cttcttggat tccgcctact tttgcttcat tacactgaca   1980
acaatcggat ttggtgactt tgtccccgcg aaaggagtca aggacgagtc ggagcagtcc   2040
atcgcctatt gctcgctgta ccttcttttc ggcattgcct tgttggccat gagtttttaac   2100 ctggtccagg aggagttcat tgccaatgtg aaggaggtag cccgccgtct gggcattctt   2160
aaggatgatg acgacgagca ggatgaggat tag                                 2193
```

<210> SEQ ID NO 4
<211> LENGTH: 730
<212> TYPE: PRT
<213> ORGANISM: Drosophila melanogaster

<400> SEQUENCE: 4

```
Met Ser Gly Arg Arg Ala Gln Ser Leu Pro Ala His Met Leu Glu Pro
  1               5                  10                  15

Ala Lys Pro Gln Arg Gly Arg Cys Val Ala Ala Ile Cys Phe Ser Trp
             20                  25                  30

Lys Val Leu Thr Cys Ile Val Ser His Val Leu Leu Val Leu Val
         35                  40                  45

Val Ser Tyr Cys Val Gly Gly Ala Tyr Leu Phe Gln His Leu Glu Arg
     50                  55                  60

Pro His Glu Leu Glu Val Lys Arg Asp Ile Gln Asn Leu Arg Val Asn
 65                  70                  75                  80

Leu Thr Glu Asn Ile Trp Leu Leu Ser Asp Asp Ala Val Val Leu Arg
                 85                  90                  95
```

-continued

```
Glu Ser Asp Trp Met Ala Asn Val Ser Lys His Leu Ala Asn Phe Glu
                100                 105                 110
Lys Gln Ile Leu Thr Ala Ile Lys Ala Asp Gly Trp Asp Gly Asp Glu
            115                 120                 125
Asp Leu Arg Lys Ser Gln Trp Thr Phe Ala Gly Ser Leu Phe Tyr Ser
        130                 135                 140
Ile Ile Val Ile Thr Thr Ile Gly Tyr Gly His Ile Ser Pro Arg Thr
145                 150                 155                 160
Asp Trp Gly Lys Val Thr Thr Ile Phe Tyr Ala Ile Val Gly Ile Pro
                165                 170                 175
Leu Met Leu Ile Cys Leu Ser Asn Ile Gly Asp Val Met Ala Thr Ser
            180                 185                 190
Phe Arg Phe Leu Tyr Trp Arg Ile Cys Cys Tyr Val Cys Thr Arg Thr
        195                 200                 205
Ala Lys Arg Pro Arg Asn Ala Arg Ser Arg Gln Arg Ser Met Arg Ser
210                 215                 220
Gln Arg His Ala Arg Ser Gln Pro Pro Ser Phe Arg Arg Ser Met
225                 230                 235                 240
Lys Met Thr Gln Arg Ser Gly Asn Asp Ser Gly Leu Gly Pro Ser Met
            245                 250                 255
Gly His Ala Tyr Ser Asp Pro Asp Leu Arg Thr Met Gly Arg Gly Tyr
        260                 265                 270
Asp Asp Arg Glu Phe Gly His Arg Ser Gly Gly Arg Asn Arg
        275                 280                 285
Arg Gln Gln Gln Gln Gln His Leu His His Asp Pro Arg Gln Arg
290                 295                 300
His Thr Ile Tyr Gly Asp Gly Tyr Glu Thr Gln Thr Leu Asn Arg Ser
305                 310                 315                 320
Asn Arg Tyr Ser Ser Arg Gln Arg Gln Arg Asp Arg Met Arg Asp Arg
                325                 330                 335
His Thr Val Glu Arg Glu Arg Tyr Ser Arg Ser His Leu Asp Ala Gly
            340                 345                 350
Ser Ile Glu Asp Phe Gly Asp Met Gln Pro Pro Ala Lys Arg Ala Ala
        355                 360                 365
Ser Val Arg Ser Val Arg Ser Pro His Asn Gln Glu Ser Ser Lys Ala
370                 375                 380
Ser Arg Glu Leu His Arg Leu His Ser Ala Pro Gly Arg Ser Arg Ala
385                 390                 395                 400
Lys Ser Val Asp Pro Arg His Val Ser Ser His Tyr Glu Asp Val Asp
                405                 410                 415
Glu Asp Val Val Arg Lys Thr Pro Ile Ile Pro Asn Arg Tyr Ala Leu
            420                 425                 430
Asp Asp Phe Gly Gly Asn Arg Gln Ala Ala Pro Arg Ser Gln Ser
        435                 440                 445
Met Pro Arg Ser Ala His Gln Arg Gln Arg Gln Lys Asp Arg Glu Arg
450                 455                 460
Glu Arg Ser Pro Gln Pro Pro Gln Ser Ser Tyr Arg Gln Gln His
465                 470                 475                 480
Asp Arg Arg Ala Gly Ser Leu Gly Arg Gln Ser Ser Arg Tyr Gly Asn
                485                 490                 495
His Leu Glu Leu Pro Asp Tyr Asp Ala Pro Pro Gly Arg Asp His
            500                 505                 510
```

-continued

```
Arg Arg Asp Arg Arg Gly His Ser Gln Gly Arg Tyr Glu Asp Tyr Val
            515                 520                 525
Glu Glu Ser Phe Asp Glu Gly Ser Leu Tyr Gly Asp Asn Asn Tyr Glu
        530                 535                 540
Asp Tyr Pro Pro Glu Arg His His Ser Arg Ser Arg Glu Pro Lys Arg
545                 550                 555                 560
Asn Arg Arg Arg Glu Arg Ala Glu Arg Leu Pro Pro Ser Pro Arg Ile
                565                 570                 575
Met Ser Pro Met Gly Phe Pro Val Gln Arg Gln Ile Arg Arg Arg Pro
            580                 585                 590
Ser Tyr Asp Tyr Asp Asp Asp Ser Met Tyr Gly Asp Glu Tyr Gly
        595                 600                 605
Asp Tyr Gly Asp Leu Leu Pro Lys Asp Arg Pro Val Pro Ile Trp Leu
610                 615                 620
Cys Val Phe Leu Val Val Ser Tyr Ile Leu Gly Gly Ala Val Leu Phe
625                 630                 635                 640
Ala Tyr Trp Glu Asn Trp Ser Phe Leu Asp Ser Ala Tyr Phe Cys Phe
                645                 650                 655
Ile Thr Leu Thr Thr Ile Gly Phe Gly Asp Phe Val Pro Ala Lys Gly
            660                 665                 670
Val Lys Asp Glu Ser Glu Gln Ser Ile Ala Tyr Cys Ser Leu Tyr Leu
        675                 680                 685
Leu Phe Gly Ile Ala Leu Leu Ala Met Ser Phe Asn Leu Val Gln Glu
    690                 695                 700
Glu Phe Ile Ala Asn Val Lys Glu Val Ala Arg Arg Leu Gly Ile Leu
705                 710                 715                 720
Lys Asp Asp Asp Glu Gln Asp Glu Asp
                725                 730
```

<210> SEQ ID NO 5
<211> LENGTH: 1188
<212> TYPE: DNA
<213> ORGANISM: Drosophila melanogaster

<400> SEQUENCE: 5

```
atgtcctccc gacgcagctc cttcaggcgg agggagaagc cggccttcga gcgctttaag     60
gaccactgcc gccacttcac ggcgttcatg ttcagcaacg tgggcatcat tctactggtc    120
acatttata  ttatcggcgg agcgttcata ttccagagca tcgagatttt cgagtacgag    180
cggctcaagt cggagaagcc gcaccggttt atagcacgga acttcagtgg cgagtgcctc    240
agccgcatat gggagttgac ggcggagaac atcagcttct tcgaccacca cgcctacagg    300
agacgggtga acgatgtgct tctggattat cagagggcca tagtgaaaaa gcagctgaag    360
ggacccgacg tggagcagtg gagcttctcc ggagcttttc tctactcact gacggtgatc    420
acgaccatcg ggtacgggaa cattacgccg cactccgagt gcggaaagct ggtgaccatt    480
ctatatgcga taattggcat gccgctgttc ttgctctacc tgtccaacat ggagacgtc     540
ctggccaagt ccttcaagtg gatatactcg aaggtgtgcc tatgtcgcat ctgccccggc    600
gtggccaagc gccggataat ccgcgagaga cgaaaaatgc gacagttggc cagagcgctc    660
cagatgcacg acatggagaa tgcccgggga agcagcagct acactagcac cagcagtacc    720
acctcctcca cagcagcag  tagcgaatac accagaagtt cccgccagag ttccagcctc    780
gtggatattc agtacaccga gtctgattcg gatatcgagc gggaaatacg cggcagcacg    840
gatgaaatta cagtgccagt cactgtgtgc gtcttcgtta tggtcgggta tatcctgtgg    900
```

```
ggtgcgctgc tcttcggtcg ttgggaggac tggaactatc tggatgggag ctacttctgc    960
cttatatcgc tcagcagcat tggatttggc gatctggtgc caggcgatcg tgtgataact   1020
gccgacaggg ataaggtgga ggttagcttc attctctgcg ccatatatct gctgctcggc   1080
atggccgtga ttgccatgtg cttcaatttg atgcaggagc aggtcgttca acacattcgg   1140
gcgatcaagc gggattcaa ggcctgcttt cggtgccgca cctcctag                 1188
```

<210> SEQ ID NO 6
<211> LENGTH: 395
<212> TYPE: PRT
<213> ORGANISM: Drosophila melanogaster

<400> SEQUENCE: 6

```
Met Ser Ser Arg Arg Ser Ser Phe Arg Arg Glu Lys Pro Ala Phe
 1               5                  10                  15

Glu Arg Phe Lys Asp His Cys Arg His Phe Thr Ala Phe Met Phe Ser
                20                  25                  30

Asn Val Gly Ile Ile Leu Leu Val Thr Phe Tyr Ile Ile Gly Gly Ala
            35                  40                  45

Phe Ile Phe Gln Ser Ile Glu Ile Phe Glu Tyr Glu Arg Leu Lys Ser
        50                  55                  60

Glu Lys Pro His Arg Phe Ile Ala Arg Asn Phe Ser Gly Glu Cys Leu
65                  70                  75                  80

Ser Arg Ile Trp Glu Leu Thr Ala Glu Asn Ile Ser Phe Phe Asp His
                85                  90                  95

His Ala Tyr Arg Arg Val Asn Asp Val Leu Leu Asp Tyr Gln Arg
            100                 105                 110

Ala Ile Val Lys Lys Gln Leu Lys Gly Pro Asp Val Glu Gln Trp Ser
        115                 120                 125

Phe Ser Gly Ala Phe Leu Tyr Ser Leu Thr Val Ile Thr Thr Ile Gly
    130                 135                 140

Tyr Gly Asn Ile Thr Pro His Ser Glu Cys Gly Lys Leu Val Thr Ile
145                 150                 155                 160

Leu Tyr Ala Ile Ile Gly Met Pro Leu Phe Leu Leu Tyr Leu Ser Asn
                165                 170                 175

Ile Gly Asp Val Leu Ala Lys Ser Phe Lys Trp Ile Tyr Ser Lys Val
            180                 185                 190

Cys Leu Cys Arg Ile Cys Pro Gly Val Ala Lys Arg Ile Ile Arg
        195                 200                 205

Glu Arg Arg Lys Met Arg Gln Leu Ala Arg Ala Leu Gln Met His Asp
    210                 215                 220

Met Glu Asn Ala Arg Gly Ser Ser Ser Tyr Thr Ser Thr Ser Thr
225                 230                 235                 240

Thr Ser Ser Asn Ser Ser Ser Glu Tyr Thr Arg Ser Ser Arg Gln
                245                 250                 255

Ser Ser Ser Leu Val Asp Ile Gln Tyr Thr Glu Ser Asp Ser Asp Ile
            260                 265                 270

Glu Arg Glu Ile Arg Gly Ser Thr Asp Glu Ile Thr Val Pro Val Thr
        275                 280                 285

Val Cys Val Phe Val Met Val Gly Tyr Ile Leu Trp Gly Ala Leu Leu
    290                 295                 300

Phe Gly Arg Trp Glu Asp Trp Asn Tyr Leu Asp Gly Ser Tyr Phe Cys
305                 310                 315                 320
```

-continued

```
Leu Ile Ser Leu Ser Ser Ile Gly Phe Gly Asp Leu Val Pro Gly Asp
            325                 330                 335

Arg Val Ile Thr Ala Asp Arg Asp Lys Val Glu Val Ser Phe Ile Leu
            340                 345                 350

Cys Ala Ile Tyr Leu Leu Gly Met Ala Val Ile Ala Met Cys Phe
            355                 360                 365

Asn Leu Met Gln Glu Gln Val Val His Asn Ile Arg Ala Ile Lys Arg
        370                 375                 380

Gly Phe Lys Ala Cys Phe Arg Cys Arg Thr Ser
385                 390                 395

<210> SEQ ID NO 7
<211> LENGTH: 3462
<212> TYPE: DNA
<213> ORGANISM: Drosophila melanogaster

<400> SEQUENCE: 7
```

| | | | | | |
|---|---|---|---|---|---|
| atgtccgacg | ttgagcaggc | gattaaggcc | aagcaaccgc | agccgtctca | gttggactgc | 60 |
| tccattgacg | atgagacgga | tgccaccgaa | ttcggaggcc | tgggcggagt | gggtggtgcg | 120 |
| ggttgtggat | cggagatggg | tgccaagacc | accgcttcgc | tgaccgccaa | gccgcgcagc | 180 |
| agtctccggc | gctgctgcgg | tcacttgctc | aagctgctct | tctccacgcc | cggcctggtg | 240 |
| ctcctggtca | tcggctactc | cgtgctgggc | gggctcctct | tcccgctgct | ggaggcgccg | 300 |
| caggacatca | gcaagtcggc | tgccattgcc | aagagccggg | aggactgctt | gcgcgaactc | 360 |
| tggatcatta | cagagaaact | caacgttctg | tacgaacgca | actggacgat | gttggtccac | 420 |
| gagcagctgc | gtcgcttcga | gggctccatt | gtggcggcca | cgcgccaagg | atctgctggc | 480 |
| tcctccggcg | gaggaggagc | aggactcttc | cacgagggca | gtgcgagtgc | cctgggccac | 540 |
| tttggctacg | atgccggcga | ctcgcagagc | tggtcattca | gcgaagctct | gctctactcg | 600 |
| gtcactgtga | taacgacaat | tggtcacggc | agcctgacgc | cgcgcaccgc | cgccgggaag | 660 |
| ctggcgacca | tcttctacgc | cctggtgggc | gtgcccctca | tgctgatgtg | cctgtccagc | 720 |
| ttgggagccc | tgctcgccga | tggcctgcag | tgcacctacg | tgcgactgtg | ctgccagctg | 780 |
| cagaggcacc | aggagcacag | aagaaagtcc | acaccaggca | tcgacgcc | atctgccagc | 840 |
| agtgcggcca | actcgaggga | aaaggacacg | gacaagaggt | ccaagcggcg | aatgttttc | 900 |
| ccacccctac | acgaaagttt | tcccccggca | actaagacag | tttcgttttt | ggccagcgga | 960 |
| aaacctgaat | ccctggtcgc | ttatgtatgg | aaatggaagg | ctggcaagtc | aggatgtgat | 1020 |
| gggaatcttc | gattgtccgg | cgatttgctt | tcctcaatgg | aattcaaccc | atttttcgca | 1080 |
| gatcagactg | cactgggctc | tcaaattacg | gcttttaatt | acgacagcag | aagccttta | 1140 |
| agtggatctc | caagccgcac | aaggatgcgt | ctggcaattg | ataagactgc | cagcagattg | 1200 |
| cggttggctc | tggggatgtg | cagtcatcgg | ttgaattatt | atcgccatcg | tgttgactgc | 1260 |
| tgccatttcg | gcttttggtc | ttttgctctt | ttggcctttg | ccatcgttct | tgcaattatc | 1320 |
| atgacgcatg | ctgccgtaac | ggtttttcgc | cgcagtgtgg | acacaggaca | tccccggaac | 1380 |
| cagggagata | ttattcggc | attatctttt | aagtgcacag | ccaattgcaa | gggctgccag | 1440 |
| tacgatgcgg | ctaacagtga | gacgagctta | atgactgct | tggagtatgg | ccaaaaggga | 1500 |
| aagctgccgc | cagacaaaaa | ggaaggagat | gcctgtcaat | tgttgcgcaa | cttgaatccg | 1560 |
| cagcagcact | tctaccagca | gcagcagcag | cagccgcagc | agccggatgt | catgctaatg | 1620 |
| acaacgacat | cgggcagtgc | gctgctgaaa | tacgcaccgc | aacagcaaca | actgcagcag | 1680 |

-continued

```
cagcagcaat tatcgacagc aacactcccg cgacaacatc atcagatgca gctgcagcag     1740
cagcagcagc aactgcaaca gaacttcgtg gctgtgccca gcagcatgct gcgaatgccg     1800
ctcacagtgc cgccaaattg ttatgcgccc gcgacagcaa cgatctactt tccgttcggc     1860
cacgccccct ccgccccggg cagtcccgcc cacaaccaag cccacccaac ccagaatccg     1920
aatggcaatg cactgggaaa cactaccctc ggttcccagc cgctggtcaa gtaccacacg     1980
atacacttgc aacccgcatc cgggaagcat cgagtgttgg cttctggact tcaggatgca     2040
acagccgtga atctcgtgac agcatccgag gcatccactt ccaccctgga ggccatcact     2100
ttgccaccgc ctccggccta ccaaacagcc agcgtgcacg gacgaagccc ccctcggatg     2160
tcccccttca acgccacagt gctcatttac gctttcaatt atataacaat tttcatcatc     2220
atcatcatca tcagcagctt gcagcagcgt gttaaaatga cagattttca acttgtgctg     2280
ctcgacatgc caggacatca acagcaacag caacaaggac ctgtgcggcg ggccaagttc     2340
gtggcgaagc cattgccaca agagatcaac gcactgatgg actgcggaac gggatcgcca     2400
gacttatccg gcagacatga tttattgccg ccacccccatt cggggtcacc agcaacaggc     2460
accgccgcaa gtcctttgtt gacctacaca gccgcagcaa caagcccaca gctgtcagct     2520
ggaattaaag gcggatcagg accagcaccc acggctggag caccaatgct tgtcagcgga     2580
gccggcagag gggcagccgc tctgaccgat aacggtttta tggccgcagg tgtctgtggc     2640
atgggtgctg ctgctgcacc ccttccagta acatcaatgg gtgcagccac tacaacagcc     2700
tcctcggcag catccacatt gtcggctctt ctaagcgcca actccacggg caacgtggac     2760
atcatggagg acgaggatga gcaggaacgg gagcgtttga gcaactgtcc gcacggaacg     2820
ccgtcccgag tgccgctgat agcgagtcct ttgagtgtgc cgcaggactc gggcgagaat     2880
accacccgca acaccgcctt caaccgccac acactgcagc cgctgagccg caagacgctg     2940
ctgctgactc gccgttgcca cagacacgcc tctggaacgc tgtacgacag tacggcgaac     3000
aacacggaga cctccgacga cgaggagtac atgcaacacg gcagcgagca gtttgtgctg     3060
aagaagttgc gctaccactg cgacggcaag gactgccgcg aggcggagga ctccgaggag     3120
gaggacgaga aggcggacgg tcggcaggtg cccatcagcc tggtgctgct catcctggcc     3180
agctacatct gcgtgggcac cgtgatcttc gctctgtggg agaactggtc gctggtggac     3240
ggagcgtact tctgttttgt taccctgtcg accattggat acggtgattt tgtgcccgcg     3300
cggagcttta acgggcctga gttgcagcta tacgcctgct gcgcttactt gcttctggga     3360
ctcgtcctgg ttgcgatgtc cttcagcatc ctggaaacgc agctcatgtg gaagtgcaaa     3420
cgcattgccg tgcgactgaa gctggcccgc gcggatggat aa                       3462
```

<210> SEQ ID NO 8
<211> LENGTH: 1153
<212> TYPE: PRT
<213> ORGANISM: Drosophila melanogaster

<400> SEQUENCE: 8

```
Met Ser Asp Val Glu Gln Ala Ile Lys Ala Lys Gln Pro Gln Pro Ser
 1               5                  10                  15

Gln Leu Asp Cys Ser Ile Asp Asp Glu Thr Asp Ala Thr Glu Phe Gly
            20                  25                  30

Gly Leu Gly Gly Val Gly Gly Ala Gly Cys Gly Ser Glu Met Gly Ala
        35                  40                  45

Lys Thr Thr Ala Ser Leu Thr Ala Lys Pro Arg Ser Ser Leu Arg Arg
    50                  55                  60
```

-continued

```
Cys Cys Gly His Leu Leu Lys Leu Leu Phe Ser Thr Pro Gly Leu Val
 65                  70                  75                  80

Leu Leu Val Ile Gly Tyr Ser Val Leu Gly Leu Leu Phe Pro Leu
                 85                  90                  95

Leu Glu Ala Pro Gln Asp Ile Ser Lys Ser Ala Ala Ile Ala Lys Ser
                100                 105                 110

Arg Glu Asp Cys Leu Arg Glu Leu Trp Ile Ile Thr Glu Lys Leu Asn
                115                 120                 125

Val Leu Tyr Glu Arg Asn Trp Thr Met Leu Val His Glu Gln Leu Arg
    130                 135                 140

Arg Phe Glu Gly Ser Ile Val Ala Ala Thr Arg Gln Gly Ser Ala Gly
145                 150                 155                 160

Ser Ser Gly Gly Gly Ala Gly Leu Phe His Glu Gly Ser Ala Ser
                165                 170                 175

Ala Leu Gly His Phe Gly Tyr Asp Ala Gly Asp Ser Gln Ser Trp Ser
                180                 185                 190

Phe Ser Glu Ala Leu Leu Tyr Ser Val Thr Val Ile Thr Thr Ile Gly
    195                 200                 205

His Gly Ser Leu Thr Pro Arg Thr Ala Ala Gly Lys Leu Ala Thr Ile
    210                 215                 220

Phe Tyr Ala Leu Val Gly Val Pro Leu Met Leu Met Cys Leu Ser Ser
225                 230                 235                 240

Leu Gly Ala Leu Leu Ala Asp Gly Leu Gln Cys Thr Tyr Val Arg Leu
                245                 250                 255

Cys Cys Gln Leu Gln Arg His Gln Glu His Arg Arg Lys Ser Thr Pro
                260                 265                 270

Gly Thr Ser Thr Pro Ser Ala Ser Ala Ala Asn Ser Arg Glu Lys
    275                 280                 285

Asp Thr Asp Lys Arg Ser Lys Arg Arg Met Phe Phe Pro Pro His His
    290                 295                 300

Glu Ser Phe Ser Pro Ala Thr Lys Thr Val Ser Phe Leu Ala Ser Gly
305                 310                 315                 320

Lys Pro Glu Ser Leu Val Ala Tyr Val Trp Lys Trp Lys Ala Gly Lys
                325                 330                 335

Ser Gly Cys Asp Gly Asn Leu Arg Leu Ser Gly Asp Leu Leu Ser Ser
                340                 345                 350

Met Glu Phe Asn Pro Phe Phe Ala Asp Gln Thr Ala Leu Gly Ser Gln
    355                 360                 365

Ile Thr Ala Phe Asn Tyr Asp Ser Arg Ser Leu Leu Ser Gly Ser Pro
    370                 375                 380

Ser Arg Thr Arg Met Arg Leu Ala Ile Asp Lys Thr Ala Ser Arg Leu
385                 390                 395                 400

Arg Leu Ala Leu Gly Met Cys Ser His Arg Leu Asn Tyr Tyr Arg His
                405                 410                 415

Arg Val Asp Cys Cys His Phe Gly Phe Trp Ser Phe Ala Leu Leu Ala
                420                 425                 430

Phe Ala Ile Val Leu Ala Ile Ile Met Thr His Ala Ala Val Thr Val
                435                 440                 445

Phe Arg Arg Ser Val Asp Thr Gly His Pro Arg Asn Gln Gly Asp Asn
    450                 455                 460

Tyr Ser Ala Leu Ser Phe Lys Cys Thr Ala Asn Cys Lys Gly Cys Gln
465                 470                 475                 480
```

-continued

```
Tyr Asp Ala Ala Asn Ser Glu Thr Ser Leu Asn Asp Cys Leu Glu Tyr
                485                 490                 495
Gly Gln Lys Gly Lys Leu Pro Asp Lys Lys Glu Gly Asp Ala Cys
            500                 505                 510
Gln Leu Leu Arg Asn Leu Asn Pro Gln Gln His Phe Tyr Gln Gln Gln
            515                 520                 525
Gln Gln Gln Pro Gln Gln Pro Asp Val Met Leu Met Thr Thr Thr Ser
530                 535                 540
Gly Ser Ala Leu Leu Lys Tyr Ala Pro Gln Gln Gln Leu Gln Gln
545                 550                 555                 560
Gln Gln Gln Leu Ser Thr Ala Thr Leu Pro Arg Gln His His Gln Met
            565                 570                 575
Gln Leu Gln Gln Gln Gln Gln Leu Gln Gln Asn Phe Val Ala Val
            580                 585                 590
Pro Ser Ser Met Leu Arg Met Pro Leu Thr Val Pro Pro Asn Cys Tyr
            595                 600                 605
Ala Pro Ala Thr Ala Thr Ile Tyr Phe Pro Phe Gly His Ala Pro Ser
            610                 615                 620
Ala Pro Gly Ser Pro Ala His Asn Gln Ala His Pro Thr Gln Asn Pro
625                 630                 635                 640
Asn Gly Asn Ala Leu Gly Asn Thr Thr Leu Gly Ser Gln Pro Leu Val
            645                 650                 655
Lys Tyr His Thr Ile His Leu Gln Pro Ala Ser Gly Lys His Arg Val
            660                 665                 670
Leu Ala Ser Gly Leu Gln Asp Ala Thr Ala Val Asn Leu Val Thr Ala
            675                 680                 685
Ser Glu Ala Ser Thr Ser Thr Leu Glu Ala Ile Thr Leu Pro Pro Pro
            690                 695                 700
Pro Ala Tyr Gln Thr Ala Ser Val His Gly Arg Ser Pro Pro Arg Met
705                 710                 715                 720
Ser Pro Phe Asn Ala Thr Val Leu Ile Tyr Ala Phe Asn Tyr Ile Thr
            725                 730                 735
Ile Phe Ile Ile Ile Ile Ile Ser Ser Leu Gln Gln Arg Val Lys
            740                 745                 750
Met Thr Asp Phe Gln Leu Val Leu Leu Asp Met Pro Gly His Gln Gln
            755                 760                 765
Gln Gln Gln Gln Gly Pro Val Arg Arg Ala Lys Phe Val Ala Lys Pro
770                 775                 780
Leu Pro Gln Glu Ile Asn Ala Leu Met Asp Cys Gly Thr Gly Ser Pro
785                 790                 795                 800
Asp Leu Ser Gly Arg His Asp Leu Leu Pro Pro His Ser Gly Ser
            805                 810                 815
Pro Ala Thr Gly Thr Ala Ala Ser Pro Leu Leu Thr Tyr Thr Ala Ala
            820                 825                 830
Ala Thr Ser Pro Gln Leu Ser Ala Gly Ile Lys Gly Ser Gly Pro
            835                 840                 845
Ala Pro Thr Ala Gly Ala Pro Met Leu Val Ser Gly Ala Gly Arg Gly
850                 855                 860
Ala Ala Ala Leu Thr Asp Asn Gly Phe Met Ala Ala Gly Val Cys Gly
865                 870                 875                 880
Met Gly Ala Ala Ala Pro Leu Pro Val Thr Ser Met Gly Ala Ala
            885                 890                 895
Thr Thr Thr Ala Ser Ser Ala Ala Ser Thr Leu Ser Ala Leu Leu Ser
```

```
            900             905             910
Ala Asn Ser Thr Gly Asn Val Asp Ile Met Glu Asp Glu Gln
        915             920             925

Glu Arg Glu Arg Leu Ser Asn Cys Pro His Gly Thr Pro Ser Arg Val
    930             935             940

Pro Leu Ile Ala Ser Pro Leu Ser Val Pro Gln Asp Ser Gly Glu Asn
945             950             955             960

Thr Thr Arg Asn Thr Ala Phe Asn Arg His Thr Leu Gln Pro Leu Ser
            965             970             975

Arg Lys Thr Leu Leu Thr Arg Arg Cys His Arg His Ala Ser Gly
        980             985             990

Thr Leu Tyr Asp Ser Thr Ala Asn Asn Thr Glu Thr Ser Asp Asp Glu
    995             1000            1005

Glu Tyr Met Gln His Gly Ser Glu Gln Phe Val Leu Lys Lys Leu Arg
    1010            1015            1020

Tyr His Cys Asp Gly Lys Asp Cys Arg Glu Ala Glu Asp Ser Glu Glu
1025            1030            1035            1040

Glu Asp Glu Lys Ala Asp Gly Arg Gln Val Pro Ile Ser Leu Val Leu
            1045            1050            1055

Leu Ile Leu Ala Ser Tyr Ile Cys Val Gly Thr Val Ile Phe Ala Leu
        1060            1065            1070

Trp Glu Asn Trp Ser Leu Val Asp Gly Ala Tyr Phe Cys Phe Val Thr
    1075            1080            1085

Leu Ser Thr Ile Gly Tyr Gly Asp Phe Val Pro Ala Arg Ser Phe Asn
    1090            1095            1100

Gly Pro Glu Leu Gln Leu Tyr Ala Cys Cys Ala Tyr Leu Leu Leu Gly
1105            1110            1115            1120

Leu Val Leu Val Ala Met Ser Phe Ser Ile Leu Glu Thr Gln Leu Met
            1125            1130            1135

Trp Lys Cys Lys Arg Ile Ala Val Arg Leu Lys Leu Ala Arg Ala Asp
        1140            1145            1150

Gly

<210> SEQ ID NO 9
<211> LENGTH: 604
<212> TYPE: DNA
<213> ORGANISM: Drosophila melanogaster

<400> SEQUENCE: 9
tatcatcgcc actgtgctgg gaattcggca cgagggacat tcttcgatgg cttctacttt      60
tgtttcatca ccatgacaac catcggattc ggtgatttgg tgccaaagaa acccaactac     120
atgctactgt gcacattgta tattcttatt ggcctggccc tgacatcgac catcattgag     180
ctggtgcgaa ggcaatatgc caccagttgg gccaagctgc aggagctatc tggtcccatg     240
gcggagactc tgcgtcgctt gggcgaaaca gccggcacgg gcctcgatta tacagccctg     300
cagaaggtgc ttacggtgtc catgcccaaa tggaatagta agaagaatag cacagtcccg     360
atattgcggc cctggaagcc atcacgaatg ccattttgaa ggaggtgaag gaggcgcaga     420
acaacaagcc gaaggtcctg cagatcgtca tatacgagtc gtccgtttag acggaaagga     480
gggatagaaa ccagacagcg agattgagct tccatcgatg aaaaaagtgc tgcatagttt     540
tgggcgagca ggcagaaaag caaaaaaaaa atatatatat acatatatca agcgaaatat     600
caat                                                                  604
```

<210> SEQ ID NO 10
<211> LENGTH: 132
<212> TYPE: PRT
<213> ORGANISM: Drosophila melanogaster

<400> SEQUENCE: 10

```
Tyr His Arg His Cys Ala Gly Asn Ser Ala Arg Gly Thr Phe Phe Asp
 1               5                  10                  15
Gly Phe Tyr Phe Cys Phe Ile Thr Met Thr Thr Ile Gly Phe Gly Asp
             20                  25                  30
Leu Val Pro Lys Lys Pro Asn Tyr Met Leu Leu Cys Thr Leu Tyr Ile
         35                  40                  45
Leu Ile Gly Leu Ala Leu Thr Ser Thr Ile Ile Glu Leu Val Arg Arg
     50                  55                  60
Gln Tyr Ala Thr Ser Trp Ala Lys Leu Gln Glu Leu Ser Gly Pro Met
 65                  70                  75                  80
Ala Glu Thr Leu Arg Arg Leu Gly Glu Thr Ala Gly Thr Gly Leu Asp
                 85                  90                  95
Tyr Thr Ala Leu Gln Lys Val Leu Thr Val Ser Met Pro Lys Trp Asn
            100                 105                 110
Ser Lys Lys Asn Ser Thr Val Pro Ile Leu Arg Pro Trp Lys Pro Ser
        115                 120                 125
Arg Met Pro Phe
    130
```

<210> SEQ ID NO 11
<211> LENGTH: 1227
<212> TYPE: DNA
<213> ORGANISM: Drosophila melanogaster

<400> SEQUENCE: 11

| | | |
|---|---|---|
| atgaagaaac aaaatgtgcg cacgatatcc ttgatcgtgt gtacatttac ctatctgctt | 60 |
| gtcggcgccg ccgtctttga cgccctcgaa tcggaaacgg aaaagcgtcg ttgggaggcg | 120 |
| ctgcaagatg ccgaggatat gataatacgc aaatacaata tctcacagga ggacttcaaa | 180 |
| gtcatggaga ctgtggtgct caaatcggaa tcgcacaagg ccggccagca atggaaattc | 240 |
| accggtgcat tctattatgc aaccacggtg ctaaccacca ttggctacgg acactcgacg | 300 |
| cccagcacgg tgggcgggaa gctcttcacc atgtgctatg ccatcgtggg gattcccctg | 360 |
| ggtctcgtta tgttccagag catcggagaa agagtgaata gactgagcag ctatgttatc | 420 |
| aaggcggtcc gctcctcgct gcgctgcaag aggaccgtcg cctcggaggt ggacctcatc | 480 |
| tgtgttgtga ccacactcag ttcgctgacg atagctggcg gtgctgcggc cttttccaaa | 540 |
| tttgagggct ggagctactt cgattcagta tattactgtt ttattacttt aaccactata | 600 |
| ggctttggcg acatggtagc cctgcagcgg gacaatgcac tgaacaggaa gcccgaatac | 660 |
| gtgatgttcg cactgatatt tatactattt ggcctggcca ttgtggccgc ctcgctgaac | 720 |
| ttgttagtac ttaggtttgt tacgatgaat accgaggatg agcgacgcga cgaggcccag | 780 |
| gccatgcagg cgctgcaagt ggctgtgaag ctggagggcg atgtgataac atccaacgga | 840 |
| tccattctga gcggctacga gggacacgat ggccaatctc tgaacggaag caacatctcg | 900 |
| tccatgtgct cgtgccactg catctgcctc aatggcaacc ggcacaaaaa agtagcaac | 960 |
| ttggaaaaga caacgatgc agaaaatcaa tacaagctga gcaatcgcc gacgcacata | 1020 |
| cgacaccttc tgccggaggt ggtgcccatg caggatttga actacgacta cgatacgcag | 1080 |

```
agcctgcaca cccttgccga tcgtggaacc atggacagca gctacatggg cgtggacatg    1140
gcggacatgg gggatacggg cagcatggag ctgcggccac acacgttgct caagcgcaat    1200
gtctcactgc tgtccatacg catctag                                         1227
```

<210> SEQ ID NO 12
<211> LENGTH: 408
<212> TYPE: PRT
<213> ORGANISM: Drosophila melanogaster

<400> SEQUENCE: 12

```
Met Lys Lys Gln Asn Val Arg Thr Ile Ser Leu Ile Val Cys Thr Phe
  1               5                  10                  15

Thr Tyr Leu Leu Val Gly Ala Ala Val Phe Asp Ala Leu Glu Ser Glu
                 20                  25                  30

Thr Glu Lys Arg Arg Trp Glu Ala Leu Gln Asp Ala Glu Asp Met Ile
             35                  40                  45

Ile Arg Lys Tyr Asn Ile Ser Gln Glu Asp Phe Lys Val Met Glu Thr
         50                  55                  60

Val Val Leu Lys Ser Glu Ser His Lys Ala Gly Gln Gln Trp Lys Phe
 65                  70                  75                  80

Thr Gly Ala Phe Tyr Tyr Ala Thr Thr Val Leu Thr Thr Ile Gly Tyr
                 85                  90                  95

Gly His Ser Thr Pro Ser Thr Val Gly Gly Lys Leu Phe Thr Met Cys
            100                 105                 110

Tyr Ala Ile Val Gly Ile Pro Leu Gly Leu Val Met Phe Gln Ser Ile
        115                 120                 125

Gly Glu Arg Val Asn Arg Leu Ser Ser Tyr Val Ile Lys Ala Val Arg
    130                 135                 140

Ser Ser Leu Arg Cys Lys Arg Thr Val Ala Ser Glu Val Asp Leu Ile
145                 150                 155                 160

Cys Val Val Thr Thr Leu Ser Ser Leu Thr Ile Ala Gly Gly Ala Ala
                165                 170                 175

Ala Phe Ser Lys Phe Glu Gly Trp Ser Tyr Phe Asp Ser Val Tyr Tyr
            180                 185                 190

Cys Phe Ile Thr Leu Thr Thr Ile Gly Phe Gly Asp Met Val Ala Leu
        195                 200                 205

Gln Arg Asp Asn Ala Leu Asn Arg Lys Pro Glu Tyr Val Met Phe Ala
    210                 215                 220

Leu Ile Phe Ile Leu Phe Gly Leu Ala Ile Val Ala Ala Ser Leu Asn
225                 230                 235                 240

Leu Leu Val Leu Arg Phe Val Thr Met Asn Thr Glu Asp Glu Arg Arg
                245                 250                 255

Asp Glu Ala Gln Ala Met Gln Ala Leu Gln Val Ala Val Lys Leu Glu
            260                 265                 270

Gly Asp Val Ile Thr Ser Asn Gly Ser Ile Leu Ser Gly Tyr Glu Gly
        275                 280                 285

His Asp Gly Gln Ser Leu Asn Gly Ser Asn Ile Ser Ser Met Cys Ser
    290                 295                 300

Cys His Cys Ile Cys Leu Asn Gly Asn Arg His Lys Lys Ser Ser Asn
305                 310                 315                 320

Leu Glu Lys Asn Asn Asp Ala Glu Asn Gln Tyr Lys Leu Arg Gln Ser
                325                 330                 335

Pro Thr His Ile Arg His Leu Leu Pro Glu Val Val Pro Met Gln Asp
            340                 345                 350
```

```
Leu Asn Tyr Asp Tyr Asp Thr Gln Ser Leu His Thr Leu Ala Asp Arg
        355                 360                 365

Gly Thr Met Asp Ser Ser Tyr Met Gly Val Asp Met Ala Asp Met Gly
    370                 375                 380

Asp Thr Gly Ser Met Glu Leu Arg Pro His Thr Leu Leu Lys Arg Asn
385                 390                 395                 400

Val Ser Leu Leu Ser Ile Arg Ile
                405
```

<210> SEQ ID NO 13
<211> LENGTH: 1086
<212> TYPE: DNA
<213> ORGANISM: Leptinotarsa decemlineata

<400> SEQUENCE: 13

```
atggacttct gcaactacgg cacagttaat aataactctt catccattgg ggatgacgag      60
gaaatcggtt tacttcccaa aattgtcgaa ggaaatcgca acaaaattat tggcatggag     120
aaaacttcct ttcggttttc actgtattta tttgcttatt tcatgttttt gtgtagcgga     180
gcagcggttt tcagttactt tgaggcacct gaggaacggg cactgagagt taaacttgga     240
acagcagtac aaaaattttt ggtgtctaat cctaacgtta cagatgcaga tttggaagaa     300
ttgatagtag aaatagtgag agcaaataat cgtggagttt cagctatcga aaatgccact     360
tcagagccta attggagttt tggtcaatca tttttctttg ccagcacagt catcacaact     420
ataggatatg gtcatgttac tccactcagc agaaatggta aattattttg catgttttat     480
gccgtggttg gaattccttt gactctggta ctgctttctg ctctcgtgga acgattactg     540
attccgacag tttggctctt gcaatggctt aattcaaaat taggacacct ttatcagcct     600
cttcgaatac gaatcgtcca tttggcaatt atagttttag tactacttgt attcttcctg     660
ctactcccag ctgcaatttt tgcgtctttg gaaccagaat gggactattt ggattctctt     720
tactattgct ttatatccct cacaacaata ggattgggag actacattcc tggagattcc     780
gcccaccagc cttaccgtcc tttatacaaa ataatgacta catgttacct tttcctgggt     840
ataacaataa tgatgttgac gctaacagta ttttacgata tacccccaact caatttgggc     900
ctactcttca caactagcga agactctgaa aaagtgaggt tagccagttc cgggccaggt     960
ttacagtacg gagcaggttt tagccctcat aatgaagata atatccaccg acaagtagtg    1020
agggttagat cgagacacaa cgatagtccc agtcctgaag aaccaccaca taaggatttt    1080
ccctaa                                                               1086
```

<210> SEQ ID NO 14
<211> LENGTH: 361
<212> TYPE: PRT
<213> ORGANISM: Leptinotarsa decemlineata

<400> SEQUENCE: 14

```
Met Asp Phe Cys Asn Tyr Gly Thr Val Asn Asn Ser Ser Ser Ile
  1               5                  10                  15

Gly Asp Asp Glu Glu Ile Gly Leu Leu Pro Lys Ile Val Glu Gly Asn
             20                  25                  30

Arg Asn Lys Ile Ile Gly Met Glu Lys Thr Ser Phe Arg Phe Ser Leu
         35                  40                  45

Tyr Leu Phe Ala Tyr Phe Met Phe Leu Cys Ser Gly Ala Ala Val Phe
     50                  55                  60
```

```
Ser Tyr Phe Glu Ala Pro Glu Arg Ala Leu Arg Val Lys Leu Gly
 65                  70                  75                  80

Thr Ala Val Gln Lys Phe Leu Val Ser Asn Pro Asn Val Thr Asp Ala
                 85                  90                  95

Asp Leu Glu Glu Leu Ile Val Glu Ile Val Arg Ala Asn Asn Arg Gly
            100                 105                 110

Val Ser Ala Ile Glu Asn Ala Thr Ser Glu Pro Asn Trp Ser Phe Gly
        115                 120                 125

Gln Ser Phe Phe Phe Ala Ser Thr Val Ile Thr Thr Ile Gly Tyr Gly
130                 135                 140

His Val Thr Pro Leu Ser Arg Asn Gly Lys Leu Phe Cys Met Phe Tyr
145                 150                 155                 160

Ala Val Val Gly Ile Pro Leu Thr Leu Val Leu Ser Ala Leu Val
                165                 170                 175

Glu Arg Leu Leu Ile Pro Thr Val Trp Leu Leu Gln Trp Leu Asn Ser
            180                 185                 190

Lys Leu Gly His Leu Tyr Gln Pro Leu Arg Ile Arg Ile Val His Leu
        195                 200                 205

Ala Ile Ile Val Leu Val Leu Leu Val Phe Phe Leu Leu Pro Ala
210                 215                 220

Ala Ile Phe Ala Ser Leu Glu Pro Glu Trp Asp Tyr Leu Asp Ser Leu
225                 230                 235                 240

Tyr Tyr Cys Phe Ile Ser Leu Thr Thr Ile Gly Leu Gly Asp Tyr Ile
                245                 250                 255

Pro Gly Asp Ser Ala His Gln Pro Tyr Arg Pro Leu Tyr Lys Ile Met
            260                 265                 270

Thr Thr Cys Tyr Leu Phe Leu Gly Ile Thr Ile Met Met Leu Thr Leu
        275                 280                 285

Thr Val Phe Tyr Asp Ile Pro Gln Leu Asn Leu Gly Leu Leu Phe Thr
290                 295                 300

Thr Ser Glu Asp Ser Glu Lys Val Arg Leu Ala Ser Ser Gly Pro Gly
305                 310                 315                 320

Leu Gln Tyr Gly Ala Gly Phe Ser Pro His Asn Glu Asp Asn Ile His
                325                 330                 335

Arg Gln Val Val Arg Val Arg Ser Arg His Asn Asp Ser Pro Ser Pro
            340                 345                 350

Glu Glu Pro Pro His Lys Gly Phe Pro
        355                 360

<210> SEQ ID NO 15
<211> LENGTH: 24
<212> TYPE: DNA
<213> ORGANISM: Drosophila melanogaster

<400> SEQUENCE: 15
tggctaaatg acgagcacga gcac                                        24

<210> SEQ ID NO 16
<211> LENGTH: 24
<212> TYPE: DNA
<213> ORGANISM: Drosophila melanogaster

<400> SEQUENCE: 16
cagtcctcct ctctcatgtt gtgg                                        24

<210> SEQ ID NO 17
```

```
<211> LENGTH: 24
<212> TYPE: DNA
<213> ORGANISM: Drosophila melanogaster

<400> SEQUENCE: 17
acaggtgcat tgcctatctc atct                                              24

<210> SEQ ID NO 18
<211> LENGTH: 22
<212> TYPE: DNA
<213> ORGANISM: Drosophila melanogaster

<400> SEQUENCE: 18
cgcgttacgg taaattcgat tg                                                22

<210> SEQ ID NO 19
<211> LENGTH: 22
<212> TYPE: DNA
<213> ORGANISM: Drosophila melanogaster

<400> SEQUENCE: 19
ttacgacgac gatgactcta tg                                                22

<210> SEQ ID NO 20
<211> LENGTH: 24
<212> TYPE: DNA
<213> ORGANISM: Drosophila melanogaster

<400> SEQUENCE: 20
aatctttagt tcaagtgcag gttt                                              24

<210> SEQ ID NO 21
<211> LENGTH: 24
<212> TYPE: DNA
<213> ORGANISM: Drosophila melanogaster

<400> SEQUENCE: 21
ctccactgct ccgatgtccg aact                                              24

<210> SEQ ID NO 22
<211> LENGTH: 23
<212> TYPE: DNA
<213> ORGANISM: Drosophila melanogaster

<400> SEQUENCE: 22
caaccgagcg gcaaattagc caa                                               23

<210> SEQ ID NO 23
<211> LENGTH: 24
<212> TYPE: DNA
<213> ORGANISM: Drosophila melanogaster

<400> SEQUENCE: 23
ttgccggatc cctgttctac tcga                                              24

<210> SEQ ID NO 24
<211> LENGTH: 24
<212> TYPE: DNA
<213> ORGANISM: Drosophila melanogaster

<400> SEQUENCE: 24
tgcgtcgtcg gacagtagcc agat                                              24
```

-continued

```
<210> SEQ ID NO 25
<211> LENGTH: 22
<212> TYPE: DNA
<213> ORGANISM: Drosophila melanogaster

<400> SEQUENCE: 25
caaatccgat tgttgtcagt gt                                              22

<210> SEQ ID NO 26
<211> LENGTH: 23
<212> TYPE: DNA
<213> ORGANISM: Drosophila melanogaster

<400> SEQUENCE: 26
gaacacactt tgaaagatgg ata                                             23

<210> SEQ ID NO 27
<211> LENGTH: 22
<212> TYPE: DNA
<213> ORGANISM: Drosophila melanogaster

<400> SEQUENCE: 27
ttacgacgac gatgactcta tg                                              22

<210> SEQ ID NO 28
<211> LENGTH: 22
<212> TYPE: DNA
<213> ORGANISM: Drosophila melanogaster

<400> SEQUENCE: 28
ctcactacca gaaagacgca ta                                              22

<210> SEQ ID NO 29
<211> LENGTH: 24
<212> TYPE: DNA
<213> ORGANISM: Drosophila melanogaster

<400> SEQUENCE: 29
ctccactgct ccgatgtccg aact                                            24

<210> SEQ ID NO 30
<211> LENGTH: 24
<212> TYPE: DNA
<213> ORGANISM: Drosophila melanogaster

<400> SEQUENCE: 30
atgacccaac ggtctgggaa tgac                                            24

<210> SEQ ID NO 31
<211> LENGTH: 38
<212> TYPE: DNA
<213> ORGANISM: Drosophila melanogaster

<400> SEQUENCE: 31
gtacatccgc gggaggaggc cagaggaggg tgaccatg                             38

<210> SEQ ID NO 32
<211> LENGTH: 26
<212> TYPE: DNA
<213> ORGANISM: Drosophila melanogaster

<400> SEQUENCE: 32
gcggtggagc atcatagtcg ggaagt                                          26
```

<210> SEQ ID NO 33
<211> LENGTH: 46
<212> TYPE: DNA
<213> ORGANISM: Drosophila melanogaster

<400> SEQUENCE: 33
actagtacta gcggccgcct aatcctcatc ctgctcgtcg tcatca                    46

<210> SEQ ID NO 34
<211> LENGTH: 26
<212> TYPE: DNA
<213> ORGANISM: Drosophila melanogaster

<400> SEQUENCE: 34
atcttccaaa gcgtccagag aactgc                                          26

<210> SEQ ID NO 35
<211> LENGTH: 24
<212> TYPE: DNA
<213> ORGANISM: Drosophila melanogaster

<400> SEQUENCE: 35
tcgccgaagg gagcggactg aacg                                            24

<210> SEQ ID NO 36
<211> LENGTH: 24
<212> TYPE: DNA
<213> ORGANISM: Drosophila melanogaster

<400> SEQUENCE: 36
gtccatcgcc tattgctcgc tgta                                            24

<210> SEQ ID NO 37
<211> LENGTH: 24
<212> TYPE: DNA
<213> ORGANISM: Drosophila melanogaster

<400> SEQUENCE: 37
ccctacttct cccaggtgcc gagt                                            24

<210> SEQ ID NO 38
<211> LENGTH: 24
<212> TYPE: DNA
<213> ORGANISM: Drosophila melanogaster

<400> SEQUENCE: 38
agtaggcgga atccaagaag gacc                                            24

<210> SEQ ID NO 39
<211> LENGTH: 24
<212> TYPE: DNA
<213> ORGANISM: Drosophila melanogaster

<400> SEQUENCE: 39
cctcactgac ggtgatcacg acca                                            24

<210> SEQ ID NO 40
<211> LENGTH: 23
<212> TYPE: DNA
<213> ORGANISM: Drosophila melanogaster

<400> SEQUENCE: 40
cgcccgaatg ttgtgaacga cct                                             23

```
<210> SEQ ID NO 41
<211> LENGTH: 24
<212> TYPE: DNA
<213> ORGANISM: Drosophila melanogaster

<400> SEQUENCE: 41
tgccgacagg gataaggtgg aggt                                          24

<210> SEQ ID NO 42
<211> LENGTH: 24
<212> TYPE: DNA
<213> ORGANISM: Drosophila melanogaster

<400> SEQUENCE: 42
ctggtgccag gcgatcgtgt gata                                          24

<210> SEQ ID NO 43
<211> LENGTH: 24
<212> TYPE: DNA
<213> ORGANISM: Drosophila melanogaster

<400> SEQUENCE: 43
ttcggtcgtt gggaggactg gaac                                          24

<210> SEQ ID NO 44
<211> LENGTH: 24
<212> TYPE: DNA
<213> ORGANISM: Drosophila melanogaster

<400> SEQUENCE: 44
cgccaatgtt ggacaggtag agca                                          24

<210> SEQ ID NO 45
<211> LENGTH: 22
<212> TYPE: DNA
<213> ORGANISM: Drosophila melanogaster

<400> SEQUENCE: 45
aaggacttgg ccaggacgtc gc                                            22

<210> SEQ ID NO 46
<211> LENGTH: 24
<212> TYPE: DNA
<213> ORGANISM: Drosophila melanogaster

<400> SEQUENCE: 46
ggcagatgcg acataggcac acct                                          24

<210> SEQ ID NO 47
<211> LENGTH: 18
<212> TYPE: DNA
<213> ORGANISM: Drosophila melanogaster

<400> SEQUENCE: 47
cgaacgcaac tggacgat                                                 18

<210> SEQ ID NO 48
<211> LENGTH: 18
<212> TYPE: DNA
<213> ORGANISM: Drosophila melanogaster

<400> SEQUENCE: 48
```

-continued cgcactgctg gcagatgg                                                     18

<210> SEQ ID NO 49
<211> LENGTH: 18
<212> TYPE: DNA
<213> ORGANISM: Drosophila melanogaster

<400> SEQUENCE: 49
gcaactgtcc gcacggaa                                                     18

<210> SEQ ID NO 50
<211> LENGTH: 18
<212> TYPE: DNA
<213> ORGANISM: Drosophila melanogaster

<400> SEQUENCE: 50
ggcaatgcgt ttgcactt                                                     18

<210> SEQ ID NO 51
<211> LENGTH: 18
<212> TYPE: DNA
<213> ORGANISM: Drosophila melanogaster

<400> SEQUENCE: 51
caccatgaca accatcgg                                                     18

<210> SEQ ID NO 52
<211> LENGTH: 18
<212> TYPE: DNA
<213> ORGANISM: Drosophila melanogaster

<400> SEQUENCE: 52
ggcattcgtg atggcttc                                                     18

<210> SEQ ID NO 53
<211> LENGTH: 18
<212> TYPE: DNA
<213> ORGANISM: Drosophila melanogaster

<400> SEQUENCE: 53
gacctcatct gtgttgtg                                                     18

<210> SEQ ID NO 54
<211> LENGTH: 18
<212> TYPE: DNA
<213> ORGANISM: Drosophila melanogaster

<400> SEQUENCE: 54
gagggctgga gctacttc                                                     18

<210> SEQ ID NO 55
<211> LENGTH: 18
<212> TYPE: DNA
<213> ORGANISM: Drosophila melanogaster

<400> SEQUENCE: 55
gcacatggac gagatgtt                                                     18

<210> SEQ ID NO 56
<211> LENGTH: 18
<212> TYPE: DNA
<213> ORGANISM: Drosophila melanogaster

<400> SEQUENCE: 56

```
cacatcgccc tccagctt                                              18

<210> SEQ ID NO 57
<211> LENGTH: 18
<212> TYPE: DNA
<213> ORGANISM: Drosophila melanogaster

<400> SEQUENCE: 57
caacatctcg tccatgtg                                              18

<210> SEQ ID NO 58
<211> LENGTH: 19
<212> TYPE: DNA
<213> ORGANISM: Drosophila melanogaster

<400> SEQUENCE: 58
gaagctggag ggcgatgtg                                             19

<210> SEQ ID NO 59
<211> LENGTH: 18
<212> TYPE: DNA
<213> ORGANISM: Drosophila melanogaster

<400> SEQUENCE: 59
cacaacacag atgaggtc                                              18

<210> SEQ ID NO 60
<211> LENGTH: 19
<212> TYPE: DNA
<213> ORGANISM: Drosophila melanogaster

<400> SEQUENCE: 60
gaagtagctc cagcccctc                                             19

<210> SEQ ID NO 61
<211> LENGTH: 22
<212> TYPE: DNA
<213> ORGANISM: Drosophila melanogaster

<400> SEQUENCE: 61
tgtgtagcgg agcagcggtt tt                                         22

<210> SEQ ID NO 62
<211> LENGTH: 23
<212> TYPE: DNA
<213> ORGANISM: Drosophila melanogaster

<400> SEQUENCE: 62
agcggttttc agttactttg agg                                        23

<210> SEQ ID NO 63
<211> LENGTH: 23
<212> TYPE: DNA
<213> ORGANISM: Drosophila melanogaster

<400> SEQUENCE: 63
gcggttttca gttactttga ggc                                        23

<210> SEQ ID NO 64
<211> LENGTH: 23
<212> TYPE: DNA
<213> ORGANISM: Drosophila melanogaster
```

<400> SEQUENCE: 64
gcacctgagg aacgggcact gag　　　　　　　　　　　　　　　　　　　　　　　23

<210> SEQ ID NO 65
<211> LENGTH: 23
<212> TYPE: DNA
<213> ORGANISM: Drosophila melanogaster

<400> SEQUENCE: 65
cccggaactg gctaacctca ctt　　　　　　　　　　　　　　　　　　　　　　　23

<210> SEQ ID NO 66
<211> LENGTH: 3033
<212> TYPE: DNA
<213> ORGANISM: Drosophila melanogaster

<400> SEQUENCE: 66

| | |
|---|---|
| tttttttttt tttttttttt tttttttttt aaattatcat tgcttttatt ttcaatattt | 60 |
| ttagcacaac aaagaaaacg tagcctgatt gcattcgatg acagtagtag tctcccttc | 120 |
| ccagtaaccc gtttatgtta gtggatttcg gacgctgtgt ttgtttggct cttctggata | 180 |
| ttcattttat ctgtatatca atctttggaa tttcgtacat ttattattta aataaactca | 240 |
| gtatgctatg taaagttaag gaaatcttta gttcaagtgc aggtttaaga tatatcagaa | 300 |
| ggtattctta aacttcgata ctattttta gggaagaagt gaatttggtt ttttaatgat | 360 |
| gtcatgcctt ccaaggaagc gctttataat taatataatc ttaactattt tacttatcat | 420 |
| attctcgttt gtgaatttaa atttgttgaa gttttttca taaaacatttt aaacatatta | 480 |
| aatatccatc tttcaaagtg tgttccttat aattagagca tccaacatat ttaggaaaaa | 540 |
| acagatgtca taactatcta tctatctatt actaatcctc atcctgctcg tcgtcatcat | 600 |
| ccttaagaat gcccagacgg cgggctacct ccttcacatt ggcaatgaac tcctcctgga | 660 |
| ccaggttaaa actcatggcc aacaaggcaa tgccgaaaag aaggtacagc gagcaatagg | 720 |
| cgatggactg ctccgactcg tccttgactc ctttcgcggg gacaaagtca ccaaatccga | 780 |
| ttgttgtcag tgtaatgaag caaaagtagg cggaatccaa gaaggaccag ttctcccagt | 840 |
| acgcaaaaag aacagctccg ccaaggatgt agctcactac cagaaagacg cataaccaaa | 900 |
| tggggacagg tcgatccttg ggcagcagat ctccatagtc cccatactca tccccgtaca | 960 |
| tagagtcatc gtcgtcgtaa tcgtagctgg gtcgccgacg gatttgccgc tggaccggaa | 1020 |
| atcccattgg tgacatgatt ctcggggaag ggggcaaacg ttcagtccgc tcccttcggc | 1080 |
| gatttctttt tggttctcga ctccttgagt ggtggcgctc aggcggataa tcctcgtagt | 1140 |
| tattgtctcc gtaaagggat ccctcatcga agctctcttc cacgtagtcc tcgtagcgac | 1200 |
| cctgggagtg gccacgccta tcccgtcgat ggtcccgtcc cggcggtgga gcatcatagt | 1260 |
| cgggaagttc gagatggttg ccatagcgag atgattgcct gcccagactt ccagctcgtc | 1320 |
| tgtcatgctg ttggcgatag gagctctgcg gtggcggctg tggagatcgt tcccgttctc | 1380 |
| tgtccttctg gcgttgcctt tggtgagcag acctgggcat ggattgactc cttggagctg | 1440 |
| cttgtcttct gttgccccg aagtcatcta agcatacct atttggtata atgggtgttt | 1500 |
| tcctcaccac gtcctcgtcg acgtcttcgt aatgtgaaga acgtgcctg ggatccacgg | 1560 |
| acttggccct acttctccca ggtgccgagt gaaggcgatg cagttctctg gacgcttttgg | 1620 |
| aagattcctg attgtgtggc gatcgaaccg atcgcacact ggcagctctt ttcgcaggag | 1680 |
| gttgcatgtc accgaagtcc tcaatggatc cagcatccaa gtgggatcgg gagtagcgct | 1740 |

-continued

```
cccttttctac cgtgtgtctg tccctcatcc gatcccgttg tctttgccgg ctactgtagc    1800
ggttggatct gttcagggtc tgagtttcgt acccatctcc gtaaatggtg tgacgctggc    1860
gaggatcgtg atgcaaatgc tgctgctgct gctgctgaca cgattccgt ccgcctccac     1920
tgctccgatg tccgaactcg cggtcatcgt agccccggcc catggtgcgc aggtcgggat    1980
ctgaataggc atgacccatg gaaggaccca gacccgagtc attcccagac cgttgggtcc    2040
tcttcatgga gcgccggaac gagggcggcg gctgggatcg ggcatggcgc tgagagcgca    2100
tcgatctctg ccgggatcgg gcattcctcg gacgtttggc cgtgcgggtg cacacgtagc    2160
agcatattct ccagtacaga aaccgaaatg atgtggccat gacatcgcca atgttggaca    2220
agcagatgag catcagcgga atgcccacaa tggcgtagaa atcgttgtc accttgcccc     2280
aatccgtacg cggcgatatg tgaccatagc ctatggtcgt tatcacaata atcgagtaga    2340
acagggatcc ggcaaaaggt ccactgggac ttgcgcagat cctcgtcgcc atcccagccg    2400
tcggccttga tggccgtaag gatttgcttt tcaaaattgg ccaggtgctt gctgacattg    2460
gccatccaat cgctttccct taggaccact gcgtcgtcgg acagtagcca gatattctcc    2520
gtgagattaa cgcgaagatt ctgtatgtct cgcttcacct ccagttcgtg ggtcgttcg     2580
aggtgctgga gaggtaggc accgcccacg caataggaaa ccacgaggag cacgagcagc    2640
acatgggaca caatgcaggt gagcaccttc acgagaaagc agatggcagc cacacagcgt    2700
ccgcgttgcg gcttcgctgg ctccaacatg tgcgccggca gagattgggc ccgcctaccc    2760
gacatggtca ccctcctctg gcctcctcct tcctttggct aatttgccgc tcggttggcg    2820
atcgctgatc gccttctgat tcgcactgag gaaaaatttt cagttttcca cattaagttc    2880
catgctgtat actttgcccg cactctcccg tcttccgtct aacaatccgt ttccgattct    2940
atatccgatg ggatccgtac agagaaaaga agcaccgatc cgtaacctgc ccgggcggcc    3000
gctcgagccc tatagtgagt cgtattagga tgg                                3033
```

<210> SEQ ID NO 67
<211> LENGTH: 741
<212> TYPE: PRT
<213> ORGANISM: Drosophila melanogaster

<400> SEQUENCE: 67

| Pro | Lys | Glu | Gly | Gly | Gln | Arg | Arg | Val | Thr | Met | Ser | Gly | Arg | Arg |
|---|---|---|---|---|---|---|---|---|---|---|---|---|---|---|
| 1 | | | | 5 | | | | | 10 | | | | | 15 |

| Ala | Gln | Ser | Leu | Pro | Ala | His | Met | Leu | Glu | Pro | Ala | Lys | Pro | Gln | Arg |
|---|---|---|---|---|---|---|---|---|---|---|---|---|---|---|---|
| | | | 20 | | | | | 25 | | | | | 30 | | |

| Gly | Arg | Cys | Val | Ala | Ala | Ile | Cys | Phe | Ser | Trp | Lys | Val | Leu | Thr | Cys |
|---|---|---|---|---|---|---|---|---|---|---|---|---|---|---|---|
| | | 35 | | | | | 40 | | | | | 45 | | | |

| Ile | Val | Ser | His | Val | Leu | Leu | Val | Leu | Val | Val | Ser | Tyr | Cys | Val |
|---|---|---|---|---|---|---|---|---|---|---|---|---|---|---|
| | 50 | | | | | 55 | | | | | 60 | | | |

| Gly | Gly | Ala | Tyr | Leu | Phe | Gln | His | Leu | Glu | Arg | Pro | His | Glu | Leu | Glu |
|---|---|---|---|---|---|---|---|---|---|---|---|---|---|---|---|
| 65 | | | | | 70 | | | | | 75 | | | | | 80 |

| Val | Lys | Arg | Asp | Ile | Gln | Asn | Leu | Arg | Val | Asn | Leu | Thr | Glu | Asn | Ile |
|---|---|---|---|---|---|---|---|---|---|---|---|---|---|---|---|
| | | | | 85 | | | | | 90 | | | | | 95 | |

| Trp | Leu | Leu | Ser | Asp | Asp | Ala | Val | Val | Leu | Arg | Glu | Ser | Asp | Trp | Met |
|---|---|---|---|---|---|---|---|---|---|---|---|---|---|---|---|
| | | | | 100 | | | | | 105 | | | | | 110 | |

| Ala | Asn | Val | Ser | Lys | His | Leu | Ala | Asn | Phe | Glu | Lys | Gln | Ile | Leu | Thr |
|---|---|---|---|---|---|---|---|---|---|---|---|---|---|---|---|
| | | | 115 | | | | | 120 | | | | | 125 | | |

| Ala | Ile | Lys | Ala | Asp | Gly | Trp | Asp | Gly | Asp | Glu | Asp | Leu | Arg | Lys | Ser |
|---|---|---|---|---|---|---|---|---|---|---|---|---|---|---|---|
| | | 130 | | | | | 135 | | | | | 140 | | | |

```
Gln Trp Thr Phe Ala Gly Ser Leu Phe Tyr Ser Ile Ile Val Ile Thr
145                 150                 155                 160

Thr Ile Gly Tyr Gly His Ile Ser Pro Arg Thr Asp Trp Gly Lys Val
                165                 170                 175

Thr Thr Ile Phe Tyr Ala Ile Val Gly Ile Pro Leu Met Leu Ile Cys
            180                 185                 190

Leu Ser Asn Ile Gly Asp Val Met Ala Thr Ser Phe Arg Phe Leu Tyr
        195                 200                 205

Trp Arg Ile Cys Cys Tyr Val Cys Thr Arg Thr Ala Lys Arg Pro Arg
    210                 215                 220

Asn Ala Arg Ser Arg Gln Arg Ser Met Arg Ser Gln Arg His Ala Arg
225                 230                 235                 240

Ser Gln Pro Pro Pro Ser Phe Arg Arg Ser Met Lys Arg Thr Gln Arg
                245                 250                 255

Ser Gly Asn Asp Ser Gly Leu Gly Pro Ser Met Gly His Ala Tyr Ser
            260                 265                 270

Asp Pro Asp Leu Arg Thr Met Gly Arg Gly Tyr Asp Asp Arg Glu Phe
        275                 280                 285

Gly His Arg Ser Ser Gly Gly Arg Asn Arg Arg Gln Gln Gln Gln
    290                 295                 300

Gln Gln His Leu His His Asp Pro Arg Gln Arg His Thr Ile Tyr Gly
305                 310                 315                 320

Asp Gly Tyr Glu Thr Gln Thr Leu Asn Arg Ser Asn Arg Tyr Ser Ser
                325                 330                 335

Arg Gln Arg Gln Arg Asp Arg Met Arg Asp Arg His Thr Val Glu Arg
            340                 345                 350

Glu Arg Tyr Ser Arg Ser His Leu Asp Ala Gly Ser Ile Glu Asp Phe
        355                 360                 365

Gly Asp Met Gln Pro Pro Ala Lys Arg Ala Ala Ser Val Arg Ser Val
    370                 375                 380

Arg Ser Pro His Asn Gln Glu Ser Ser Lys Ala Ser Arg Glu Leu His
385                 390                 395                 400

Arg Leu His Ser Ala Pro Gly Arg Ser Arg Ala Lys Ser Val Asp Pro
                405                 410                 415

Arg His Val Ser Ser His Tyr Glu Asp Val Asp Glu Asp Val Val Arg
            420                 425                 430

Lys Thr Pro Ile Ile Pro Asn Arg Tyr Ala Leu Asp Asp Phe Gly Gly
        435                 440                 445

Asn Arg Arg Gln Ala Ala Pro Arg Ser Gln Ser Met Pro Arg Ser Ala
    450                 455                 460

His Gln Arg Gln Arg Gln Lys Asp Arg Glu Arg Glu Arg Ser Pro Gln
465                 470                 475                 480

Pro Pro Pro Gln Ser Ser Tyr Arg Gln Gln His Asp Arg Arg Ala Gly
                485                 490                 495

Ser Leu Gly Arg Gln Ser Ser Arg Tyr Gly Asn His Leu Glu Leu Pro
            500                 505                 510

Asp Tyr Asp Ala Pro Pro Gly Arg Asp His Arg Arg Asp Arg Arg
        515                 520                 525

Gly His Ser Gln Gly Arg Tyr Glu Asp Tyr Val Glu Glu Ser Phe Asp
    530                 535                 540

Glu Gly Ser Leu Tyr Gly Asp Asn Asn Tyr Glu Asp Tyr Pro Pro Glu
545                 550                 555                 560
```

```
Arg His His Ser Arg Ser Arg Glu Pro Lys Arg Asn Arg Arg Glu
            565                 570                 575

Arg Thr Glu Arg Leu Pro Pro Ser Pro Arg Ile Met Ser Pro Met Gly
        580                 585                 590

Phe Pro Val Gln Arg Gln Ile Arg Arg Pro Ser Tyr Asp Tyr Asp
        595                 600                 605

Asp Asp Asp Ser Met Tyr Gly Asp Glu Tyr Gly Asp Tyr Gly Asp Leu
        610                 615                 620

Leu Pro Lys Asp Arg Pro Val Pro Ile Trp Leu Cys Val Phe Leu Val
625                 630                 635                 640

Val Ser Tyr Ile Leu Gly Gly Ala Val Leu Phe Ala Tyr Trp Glu Asn
                645                 650                 655

Trp Ser Phe Leu Asp Ser Ala Tyr Phe Cys Phe Ile Thr Leu Thr Thr
                660                 665                 670

Ile Gly Phe Gly Asp Phe Val Pro Ala Lys Gly Val Lys Asp Glu Ser
                675                 680                 685

Glu Gln Ser Ile Ala Tyr Cys Ser Leu Tyr Leu Leu Phe Gly Ile Ala
        690                 695                 700

Leu Leu Ala Met Ser Phe Asn Leu Val Gln Glu Glu Phe Ile Ala Asn
705                 710                 715                 720

Val Lys Glu Val Ala Arg Arg Leu Gly Ile Leu Lys Asp Asp Asp Asp
                725                 730                 735

Glu Gln Asp Glu Asp
            740

<210> SEQ ID NO 68
<211> LENGTH: 438
<212> TYPE: DNA
<213> ORGANISM: Drosophila melanogaster

<400> SEQUENCE: 68
gcacatggac gagatgttgc ttccgttcag agattggcca tcgtgtccct cgtagccgct      60
cagaatggat ccgttggatg ttatcacatc gccctccagc ttcacagcca cttgcagcgc     120
ctgcatggcc tgggcctcgt cgcgtcgctc atcctcggta ttcatcgtaa caaacctaag     180
tactaacaag ttcagcgagg cggccacaat ggccaggcca aatagtataa atatcagtgc     240
gaacatcacg tattcgggct tcctgttcag tgcattgtcc cgctgcaggg ctaccatgtc     300
gccaaagcct atagtggtta agtaataaaa acagtaatat actgaatcga gtagctcca     360 gccctcaaat ttggaaaagg ccgcagcacc gccagctatc gtcagcgaac tgagtgtggt     420
cacaacacag atgaggtc                                                    438

<210> SEQ ID NO 69
<211> LENGTH: 146
<212> TYPE: PRT
<213> ORGANISM: Drosophila melanogaster

<400> SEQUENCE: 69

Asp Leu Ile Cys Val Val Thr Thr Leu Ser Ser Leu Thr Ile Ala Gly
  1               5                  10                  15

Gly Ala Ala Ala Phe Ser Lys Phe Glu Gly Trp Ser Tyr Phe Asp Ser
                 20                  25                  30

Val Tyr Tyr Cys Phe Ile Thr Leu Thr Thr Ile Gly Phe Gly Asp Met
             35                  40                  45

Val Ala Leu Gln Arg Asp Asn Ala Leu Asn Arg Lys Pro Glu Tyr Val
         50                  55                  60
```

```
Met Phe Ala Leu Ile Phe Ile Leu Phe Gly Leu Ala Ile Val Ala Ala
 65                  70                  75                  80

Ser Leu Asn Leu Leu Val Leu Arg Phe Val Thr Met Asn Thr Glu Asp
                 85                  90                  95

Glu Arg Arg Asp Glu Ala Gln Ala Met Gln Ala Leu Gln Val Ala Val
                100                 105                 110

Lys Leu Glu Gly Asp Val Ile Thr Ser Asn Gly Ser Ile Leu Ser Gly
            115                 120                 125

Tyr Glu Gly His Asp Gly Gln Ser Leu Asn Gly Ser Asn Ile Ser Ser
        130                 135                 140

Met Cys
145

<210> SEQ ID NO 70
<211> LENGTH: 461
<212> TYPE: DNA
<213> ORGANISM: Drosophila melanogaster

<400> SEQUENCE: 70
gacgcacata cgacaccttc tgccggaggt ggtgcccatg caggatttga actacgacta      60
cgatacgcag agcctgcaca ccctggccga tcgtggaacc atggacagca gctacatggg     120
cgtggacatg gcggacatgg gggatacggg cagcatggag ctgcggccac acacgttgct     180
caagcgcaat gtctcactgc tgtccatacg catctaggcg gcgatgtcgt catctgcgga     240
cggcggtgga ggattggcgg gtaccgggaa caacgaagtg gcccacgacc ttgccaaaaa     300
cgacttacaa atcgaaagtg ataacaaggc tctaatagta cttaaatact tatggtagat     360
tcgcaactga cgattaattg atcgttggat tgattgacct gtgcgatagt ttgtgtaggc     420
tccacccgcg acttggacac gccatgtgtg tgcatttaca a                         461
```